United States Patent
Besenmatter et al.

(10) Patent No.: US 8,709,777 B2
(45) Date of Patent: *Apr. 29, 2014

(54) VARIANTS OF A FAMILY 44 XYLOGLUCANASE

(75) Inventors: Werner Besenmatter, Soeborg (DK); Esben Peter Friis, Herlev (DK); Keith Gibson, Bagsvaerd (DK); Frank Winther Rasmussen, Roskilde (DK); Michael Skjoet, Jyllinge (DK)

(73) Assignee: Novozymes A/S, Bagsvaerd (DK)

(*) Notice: Subject to any disclaimer, the term of this patent is extended or adjusted under 35 U.S.C. 154(b) by 314 days.

This patent is subject to a terminal disclaimer.

(21) Appl. No.: 12/995,706

(22) PCT Filed: Jun. 4, 2009

(86) PCT No.: PCT/EP2009/056875
§ 371 (c)(1),
(2), (4) Date: Dec. 14, 2010

(87) PCT Pub. No.: WO2009/147210
PCT Pub. Date: Dec. 10, 2009

(65) Prior Publication Data
US 2011/0092409 A1 Apr. 21, 2011

Related U.S. Application Data

(60) Provisional application No. 61/059,832, filed on Jun. 9, 2008.

(30) Foreign Application Priority Data

Jun. 6, 2008 (EP) ................................ 08157769

(51) Int. Cl.
*C12N 9/42* (2006.01)
*C12N 15/56* (2006.01)

(52) U.S. Cl.
USPC .......................................... 435/209; 536/23.2

(58) Field of Classification Search
None
See application file for complete search history.

(56) References Cited

U.S. PATENT DOCUMENTS

2003/0032162 A1 2/2003 Schnorr et al.

FOREIGN PATENT DOCUMENTS

| WO | WO 91/10732 A1 | 7/1991 |
| WO | WO 94/14953 A1 | 7/1994 |
| WO | WO 99/02663 A1 | 1/1999 |
| WO | WO 01/62903 A1 | 8/2001 |

OTHER PUBLICATIONS

Alexander et al, Biochemistry, vol. 40, No. 35, pp. 10640-10644 (2001).
Cazy Family GH44, XP-002541180—CAZY—Carbohydrate—Active Enzymes pp. 1-2 (retrieved on Aug. 12, 2009).
Cho et al, Applied Microbiol Biotechnol, vol. 73, No. 3, pp. 618-630 (2006).
Cho et al, Biotechnol Letters, vol. 30, No. 6, pp. 1061-1068 (2008).
Bernard Henrissat, Biochem. Journal, vol. 280, pp. 306-316 (1991).
Henrissat et al, Biochem. Journal, vol. 293, pp. 781-788 (1993).
Kitago et al, The Journal of Biological Chemistry, vol. 282, No. 49, pp. 35703-35711 (2007).
Vincken et al, Carbohydrate Research, vol. 298, pp. 299-310 (1997).

*Primary Examiner* — Rebecca Prouty
(74) *Attorney, Agent, or Firm* — Elias Lambiris

(57) ABSTRACT

The present invention relates to variants of a parent xyloglucanase. The present invention also relates to polynucleotides encoding the variant xyloglucanases and to nucleic acid constructs, vectors, and host cells comprising the polynucleotide.

10 Claims, 9 Drawing Sheets

```
SEQ_ID_NO_3              VVHGQTAKTITIKVDTFKDRKPISPYIYGTMQ----DLAGDENMAARRLGGNRMTGYNWENNMSNA
SEQ_ID_NO_5              VVHGQTAKTVTIKVDTSKDRKPISPYIYGTMQ----ELAGDENLTARRLGGNRMTGYNWENNMSNA
SEQ_ID_NO_7              VVHGQTAKTVTIKVDTSKDRKPISPYIYGTMQ----DLAGDENLAARRLGGNRMTGYNWENNMSNA
SEQ_ID_NO_8    q1a2d0    VVHGQTAKTITIKVDTFKDRKPISPYIYGTMQ----DLAGDENMAARRLGGNRMTGYNWENNMSNA
SEQ_ID_NO_9    p29719    ASVNAAASDVTFTINTQSERAAISPNIYGTNQ----DLSGTENWSSRRLGGNRLTGYNWENNASSA
SEQ_ID_NO_10   p71140    --PTEPAKVVDIRIDTSAERKPISPYIYGSNQ----EL--DATVTAKRFGGNRTTGYNWENNFSNA
SEQ_ID_NO_11   a3dd30    --PTEPAKVVDIRIDTSAERKPISPYIYGSNQ----EL--DATVTAKRFGGNRTTGYNWENNFSNA
SEQ_ID_NO_12   q977y3    ----ADTADVNVNIDTNAEKQAISPYIYGTNQ----DFS-NAKVTARRIGGNRSTGYNWENNDSNA
SEQ_ID_NO_13   a0uzx7    ----SAAASDAINVSIDTTAERAAISPYIYGGNW----EFN-NAKLTAKRFGGNRTTGYNWENNYSNA
SEQ_ID_NO_14   q9agg4    ----PAVTPDVKISIDTSRGRTKISPYIYGANQ----DIQ-GVVHPARRLGGNRLTGYNWENNMSNA
SEQ_ID_NO_15   q2zh58    PTISPSPSVVEITTNTNAGRTOISPYIYGANQ----DIE-GVVHSARRLGGNRLTGYNWENNFSNA
SEQ_ID_NO_16   p22533    PTISPSPSVVEITNTNAGRTQISPYIYGANQ----DIE-GVVHSARRLGGNRLTGYNWENNFSNA
SEQ_ID_NO_17   q52743    KVNAAGGFDMNIKVDLKGERKEISPLIYGVNQYTTDLK-SVKTTAVRQGGNRMTAYNWENNASNA
SEQ_ID_NO_18   q934f9    TVNAAGGYDMNVTVDLKGEKKAISPLIYGVNQYTTDLR-DVKTTAVRQGNRMTAYNWETNASNA
SEQ_ID_NO_19   a1e9a6    ---AQNPSVTISVMANAGRHPINPAVGLAYATTATLADLNVPLHRYGGNNTSRYNWQLNADNR
SEQ_ID_NO_20   Consensus01  VVHGATAKDVTIKIDTSAERKPISPYIYGTNQYTDLAGDVNVTARRLGGNRMTGYNWENNMSNA
SEQ_ID_NO_21   Consensus02  PTPAQSTSVINVTVNLNKGTA-N-LV--AAYA--EISAGEKLSSK-F---NTSA---QT-FDSR
SEQ_ID_NO_22   Consensus03  TSNTPPPPTMEFS--AKGD-AQ---N----V-W---AFE-NAVHALV-Q----L-R-----A---
SEQ_ID_NO_23   Consensus04  K-ISEGGYS-D-R---TS---QK---A--S----TR-TLTTP-H-Y-----S------Y-----
               ruler      1.........10........20........30........40........50........60.....
```

```
SEQ_ID_NO_3              NAKNAPFQLQPDLNDN----------------RVYVDEFVHFLVNKYGTASTKAGVKGYALDNEPALWSHT
SEQ_ID_NO_5              NAKNAPFQLQPDLKDN----------------QVYADEFVNFLVKKYGVASTKTGVKGYSLDNEPALWSHT
SEQ_ID_NO_7              NAKNAPFQLQPDLMDN----------------QVYADEFVNFLVKKYGAASTKAGVKGYALDNEPALWSHT
SEQ_ID_NO_8  q1a2d0      NAKNTPFQLQPDLMDN----------------RVYVDEFVHFLVNKYGTASTKAGVKGYALDNEPALWSET
SEQ_ID_NO_9  p29719      FAKNAPFSLQPHLNDG----------------QVYMDEEVNFLVNRYGNASTSTGIKAYSLDNEPALWSHT
SEQ_ID_NO_10 p71140      FEKGAPFSLTPDTEDD----------------YVYMDEFVNYLVNKYGNASTPTGIKGYSIDNEPALWSHT
SEQ_ID_NO_11 a3dd30      FEKGAPFSLTPDTEDD----------------YVYMDEFVNYLVNKYGNASTPTGIKGYSLDNEPSLWPST
SEQ_ID_NO_12 q977y3      FNKNGPLSLTPDTTDG----------------SVYMDEFVNYLVNKYGSASGSKGIKGYSLDNEPSLWMPST
SEQ_ID_NO_13 a0uzx7      FKKDAPLSLTPDTTDN----------------YVYMDELVNLLIVNKYGSASTATGIKGYAIDNEPALWSGT
SEQ_ID_NO_14 q9agg4      FKKDGALSLQPDVNDN----------------YVYMDEFINYLINKYCRSSSATGIKGYILDNEPDLWFTT
SEQ_ID_NO_15 q2zh58      FKKDAPLSLNPDLNDN----------------FVYMDEFINYLINKYGMASSPTGIKGYILDNEPDLWAST
SEQ_ID_NO_16 p22533      FKKDAPLSLNPDLNDN----------------FVYMDEFINYLINKYGMASSPTGIKGYILDNEPDIWAST
SEQ_ID_NO_17 q52743      FTKGAPFADEPDLTDG----------------VVYMDEYVNYIINKLGDSQSPTGIQYSLDNEPVLWNDT
SEQ_ID_NO_18 q93449      LTKNAPFADTPDLTDG----------------VVYMDEYVNYIINKLGDSQSAEGIQGYSLDNEPVLWNDT
SEQ_ID_NO_19 a1e9a6      DAGNGVLTSGQNVIGNNPNDANTLVDSTFQQGWAQHLVSQWGTAAGG-GLRYVILDNEPSIWFST
SEQ_ID_NO_20 Consensus01 FAKNAPFSLQPDLNDNNPNDANTLVDYVYMDEFVNYLVNKYGTASTPTGIKGYSLDNEPALWSHT
SEQ_ID_NO_21 Consensus02 NKGDGVLQDTQMTTGG----------------QTFVQGYIHFIKRL-NSQSKA-VQY-II----DI-NS-
SEQ_ID_NO_22 Consensus03 L?-GTA-ASN-HVE-D----------------V---A---WAQL--SQW-S-AGAK-LRA-A----V-FD-
SEQ_ID_NO_23 Consensus04 DE------T-G--K------------------S---Q-i--H-------M--SE-----------S--AT-
ruler        ........160.......170.......180.......190.......200.......210.......
```

FIG. 1C

```
HPRIHGEKVGAKELVDRSVSLSKAVKAIDAGAEVFGPVLYGFGAY----KDLQTA----PDWDSV--KGNY-SW-FVDYYLDQMRL 268
HPRIHGEKVGAKELVDRSVSLSKAVKAIDAGAEVFGPVLYGFGAY----KDLQTA----PDWNSV--KGNY-SW-FVDYYLDQMRL 268
HPRIHGEKVGAKELVDRSVSLSKAVKAVDAGAEIFGPVLYGFGAY----TDLQTA----PDWNSV--KGNY-SW-FVDYYLDQMRL 268
HPRIHGEKVGAKELVDRSVSLSKAVKAVDAGAEIFGP2VLYGFGAY----KDLQTA----PDWNSV--KGNY-SW-FVDYYLDQMRL 268
HPRIHPEQLQAAELVAKSIDLSKAVKNVDPHAEIFGPALYGFGAY----LSIQDA----PGWPSL--QGNY-SW-FIDYYLDQMKN 268
HPRIHPDNVTAKELIEKSVALSKAVKKVDPYAEIFGPALYGFAAY----ETLQSA----PDWGTE--GEGY-RW-FIDYYLDKMKK 265
HPRIHPDNVTAKELIEKSVALSKAVKKVDPYAEIFGPALYGFAAY----ETLQSA----PDWGTE--GEGY-RW-FIDYYLDKMKK 265
HPLIHPDKTKCSEVLDKDTQLAQVKKIDPAAETFGPALFGFSAF----NDFNSS----PDWSSV--KGNY-QW-FIDYYLDNMKK 264
HPRMHPNNATCAEVIDKNINLAKTVKGVDPSAETFGLVAYGFAAY----NDFQSA----TDWKDL--KGNY-TW-FLDYYLDSMKK 266
HPRIHPQKVTCSELINKSVELAKVIKTLDPDAEIFGPASYGFVGY----LTLQDA----PDWNQV--KGMH-RW-FLSWYLEQMKK 264
HPRIHPNKVTCKELIEKSVELAKVIKTLDPSAEVFGYASYGFMGY----YSLQDA----PDWNQV--KGEH-RW-FISWYLEQMKK 267
HPRIHPNKVTCKELIEKSVELAKVIKTLDPSAEVFGYASYGFMGY----YSLQDA----PDWNQV--KGEH-RW-FISWYLEQMKK 267
HPRVHPEPVTIEELGNKSIELAKAVKKLDPKAEIFGPALYGYTAF----DHLDDDEQHTESGDVKSKMNY-HW-YLDCYLDQMKK 268
HSRMHPDPVTIEELGSKSVEMAKAVKKLDPKAEVFGPALYGYTAF----DHLDDDDAHTEWEEIKKANNY-HW-YLDCYLDHMHK 268
HRDVHPVGPTMDEIRDKMLDYGAKIKTVDPSALIVGPEEWGWSGYTLSGYDQQYGGL-HGWSFMPDRNNHGGWDYLPWLLDQLRQ 283
HPRIHPEKVTAKELIDKSVELSKAVKKVDPSAEIFGPALYGFGAYTLSGYDLQDAGQHPDWNSVKSKGNYGSWDFIDYYLDQMKK 300
-SLV-GDNTGCS--VVERNISYAQVI-TL-AG-LVV-YVSW-YAGF------KTFDTIDEL-TCSGQLPKGNGH-R--YLSWL-EKLRL 234
-RDM--NPPQIE-IGN-MTDMGATA-AI--Y--T--LEEF-WT------NSQNSSDA-HE-STE-DREE---H----VPC----S--HQ 177
----VQLKMA---RS--DLA---K---N------A---S-------DDM----Q--------T-------N--N 107
...220........230........240........250........260........270........280........290........300
```

FIG. 1D

```
SEQ_ID_NO:3                SSQVEGKRLLDVFDVHWYPEAMGGGIRITN----EVGNDETKKARMQAPRTLWDPTYK--------
SEQ_ID_NO_5                SSQAEGKRLLDVFDVHWYPEAMGGGIRITN----EVGNDETKKARMQAPRTLWDPTYK--------
SEQ_ID_NO_7                NSQAEGKRLLDVFDVHWYPEAMGGGIRITN----EVGNDETKKARMQAPRTLWDPTYK--------
SEQ_ID_NO_8  q1a2d0        SSQAEGKRLLDVFDVHWYPEAQGGGIRITN----EVGNDETKKARMQAPRTLWDPTYK--------
SEQ_ID_NO_9  p29719        AHTQNGKRLLDVLDVHWYPEAQGGQRIVF-G-GAGNIDTQKARVQAPRSLWDPAYQ----------
SEQ_ID_NO_10 p71140        ASDEEGKRLLDVLDVHWYPEARGGGERICF-GADPRNIETNKARLQAPRTLWDPTYI---------
SEQ_ID_NO_11 a3dd30        ASDEEGKRLLDVLDVHWYPEARGGGERICE-GADPRNIETNKARLQAPRTLWDPTYI---------
SEQ_ID_NO_12 q977y3        NSDAAGKRLLDALDLHWYPEAKGGGQRVTT--SDTSNVDCNKARMQAPRSLWDSTYT---------
SEQ_ID_NO_13 a0uzx7        ASTEAGTRLIDALDLHWYPEAKGGGQRICF-GEDPTNILCNKARLQAARTLWDPTYK---------
SEQ_ID_NO_14 q9agg4        ASDSFGKRLLDVLDIHWYPEAQVGGVRICFDGENSTSRDVAIARMQAPRTLWDPTYKTTQKGQIT-
SEQ_ID_NO_15 c2zh58        ASDSFGKRLLDVLDLHWYPEARGGNIRVCFDGENDTSKEVVIARMQAPRTLWDPTYKTSVKGQIT-
SEQ_ID_NO_16 p22533        ASDSFGKRLLDVLDLHWYPEARGGNIRVCFDGENDTSKEVVIARMQAPRTLWDPTYKTSVKGQIT-
SEQ_ID_NO_17 q52743        ASEEEGTRLLDVLDIHYYSESARTG---------------AEDRVQSVRTLYEEGFS---------
SEQ_ID_NO_18 g934f9        ASEENGARLLDVLDIHYYSESARKG---------------IEDRLQSVRTLYEPGFS---------
SEQ_ID_NO_19 a1e9a6        NNLSTGRRLLDVFSVHYYPQGGEFG------NDTSSAMQLRRNRSTRSLWDPNYI----------
SEQ_ID_NO_20 Consensus01   ASDEEGKRLLDVLDVHWYPEARGGGIRICFDGENVTNIETNKARMQAPRTLWDPTYKTSVKGQIT-
SEQ_ID_NO_21 Consensus02   SNQSF-T--I-AFSL-Y-SQSMRTNQ-VTN--AEPGSDDVKID-LRSV-S-YESGFI-TQ------
SEQ_ID_NO_22 Consensus03   NHTAN-R------I------GQVK-E--VT--SDDR-KLCVER-V---T---EN-S---------
SEQ_ID_NO_23 Consensus04   --EVA-A-------KEF-V------GTS-VAMQL--N---A----A-T---
ruler                      .........310.......320.......330.......340.......350.......360...
```

FIG. 1E

```
--EDSWIAQWNSEFLPIIPRLKQSVDKYYPGTKLAMTEYSYGGENDISGGIAMTDVLGILGKNDVYMANYWKLKDGVNNYVSAAY   405
--EDSWIAQWNSEFLPLLPRLKQSVDKYYPGTKLLALTEYSYGGENDISGGIAMADVLGILGKNDVYMANYWKLKDGANNYVSAAY   405
--EDSWIAQWNSAFLPLLPRLKQSVDKYYPGTKLALTEYSYGGENDISGGIAMTDVLGILGKNDVYMANYWKLKDGANNYVSAAY   405
--EDSWIAQWNSEFLPLIPRLKQSVDKYYPGTKLAMTEYSYGGENDISGGIAMTDVLGILGKNDVYMANYWKLKDGVNNYVSPAY   405
--EDSWIGTWFSSYLPLIPKLQSSIQTYPGTKLAITESSYGDNHISGGIATADALGIFGKYGVYAANYW-QTEDNTDYTSAAY     405
--EDSWIGQWKKDFLPLPNLLDSIEKYYPGTKLAITEYDYGGNHTGGIAQADVLGIFGKYGVLATFW---GDASNNYTEAGI      402
--EDSWIGQWKKDFLPILPNLLDSIEKYYPGTKLAITEYDYGGNHITGGIAQADVLGIFGKYGVLATFW---GDASNNYTEAGI    402
--EDSWIGQWKKDFLPILPNLLDSIEKYYPGTKLAITEYDYGGNHITGGIAQADVLGIFGKYGVLATEW---GDASNNYTEAGI    402
--EDSWIGQWKWGLPLIPKVKSSIDKYYPGTKLSFSEYNYGGEDHISGGIAQADALGVFGKYGVFATYWECNSDKNNYVQSAF     402
--EDSWIAQWCSEFGLPLIPKVQESIDKYNPGTKLAFTEYSYGADNHTGGIAEADVLGIAEADVLGVFGKYGVLATVW-----GGGSYTAAGV    401
AGENSWINQWFPEYLPIPLPNIKADIDKYYPGTKLAITEFDYGGKDHISGGIALADVLGIFGKYGVMAARW---GDSGSYAQAAY  411
AGENSWINQWFSDYLPIIPNVKADIEKYYPGTKLAISEFDYGGRNHISGGIALADVLGIFGKYGVNFAARW---GDSGSYAAAAY  414
AGENSWINQWFSDYLPIIPNVKADIEKYYPGTKLAISEFDYGGRNHISGGIALADVLGIFGKYGVNFAARW---GDSGSYAAAAY  414
--ENSWIGQWCMQNVPILPTIKKSIDTYYPGTKLAISEYNFKGGEDTSGTTAQAEKALGCFADQGVYLATLW----GGEPFIISGI 389
--ENSMIGQWCMENVPILPTIQKSIDTYYPGTKLGISEYNFGGGDDASGTTAQAEKALGCYADQGVYFASIM----GGEPFILSGI 389
--DETWIN------DKVQLIPRLKNWVSTYYPGTLTATTEYNWGAESHINGATTQADILGFREGLDMAARW--TTPDTATPTYKAI 410
AGEDSWIGQWNSEFLPILPRLKQSIDKYYPGTKLAITEYSYGGENHISGGIAQADVLGKYGVMATYWKLKDGSNNYVSAAY      450
--DNT--AT-FKDYVQLI-NVQADVET-N----LTSMS-FDFKAGDDTT-TTMTEA--VLADNDLNL-NR-ETTGDGSFTASGI   350
------E----N---CMWN-S--------GL--SNW---RS-AN--A--L---CY--RQ--DF-AL--QGSAVEPPAQP-V     250
--------------KPSG-----T--K--Q----------P------DE----T----E---A-SF--CNP-ATT-IEK-F     152
  ...370.........380.........390.........400.........410.........420.........430.........440.........450
```

FIG. 1F

```
SEQ_ID_NO:3             KLYRNYDGKNSTFGDTSVSAQTSDIVNSSVHASVTNASDKELHLVMNKSMDSAFDAQFDL-SGA
SEQ_ID_NO_5             KLYRNYDCKSSTFGDISVHAQTSDIVNSSVHASVTDASYKELHLVMNKSMDSAFDAQFDL-SGE
SEQ_ID_NO_7             KLYRNYDGKNATFGDISVNAQTSDIVNSSVHASVTDASYKELHLIVMNKSMDSAFDAQFDL-SGE
SEQ_ID_NO_8_q1a2d0      KLYRNYDGKNSTFGDTSVSAQTSDIVNSSVHASVTNASDKELHLVMNKSMDSAFDAQFDL-SGA
SEQ_ID_NO_9_p29719      KLYRNYDGNKSGFGSIKVDAATSDTENSSVYASVTDEENSELHLIVLNKNFDDPINATFQL-SGD
SEQ_ID_NO_10_p71140     NLYTNYDGKGGKFGDTSVKCEFSDIEVSSAYASIVGEDDSKLHIILLNKNYDQPTTFNFSI-DSS
SEQ_ID_NO_11_a3dd30     NLYTNYDGKGGKFGDTSVKCETSDIEVSSAYASIVGEDDSKLHIILLNKNYDQPTTFNFSI-DSS
SEQ_ID_NO_12_q977y3     NLYTNYDGNNSKYGDTDVKCDTSDINNSSTYASVTSNDGNKMDIIVMNKNYTDSINFNFNV-SSN
SEQ_ID_NO_13_a0uzx7     NIYTNYDGNGSKYGDTKVKAETSDVENSSVYASVDSKDDSKLHVILINKNYDSPMTVNFGI-NSD
SEQ_ID_NO_14_q9agg4     NIYLNYDGKGSRYGSTCVSAETTDVENMPVYASIEGEDDSTVHIILINRNYDRKLKAEIKM-NNT
SEQ_ID_NO_15_q2zh58     NIYLNYDGKGSKYGNTNVSANTSDVENMPVYASINGQDDSELHIILINRNYDQKLQVKINI-TST
SEQ_ID_NO_16_p22533     NIYLNYDGKGSKYGNTNVSANTSDVENMPVYASINGQDDSELHIILINRNYDQKLQVKINI-TST
SEQ_ID_NO_17_q52743     NLYTNYDGKGGCFGDTLIPASTEDVSKSSTYAAVNDGDESKVTVMTTNKNMTEAENAVIDLENAS
SEQ_ID_NO_18_q934f9     QLYTNYDGKGGCFGDTLIPASTGDVSKSSTYAAVNAKDDSKVTVMVTMKDLKENENAVIDLRNAD
SEQ_ID_NO_19_a1e9a6     KMYRNYDGNKSAFGDTSVTATAPNPDNVSAFAAVRSSDGA-LTVMVINKYLSGNTPATINL-SNF
SEQ_ID_NO_20_Consensus01 NLYRNYDGKGSKFGDTSVSAQTSDIENSSVYASVTGEDDSELHIIVMNKNYDSAFNAQFDLRSST
SEQ_ID_NO_21_Consensus02 KI-T----NNGTY-SINIKCEATNVVVMPTH-AINDASYKKVTLVLI-RSMTQPTDVNINIENGS
SEQ_ID_NO_22_Consensus03 QM-L----KAC-N-L-P-S-P-TSKV-AF---VSQEGNTMDVMIL--YLSEKLTFV-SV-TND
SEQ_ID_NO_23_Consensus04 ---N----S-R--T--K-T-N-G-PN-----RNK-NA----T--DFKDNIQ-T-QM-DAE
                   ruler .........460.........470.........480.........490.........500......510.....
```

FIG. 1G

```
KTYISGKVWGFDKNSSQIKEAAPITQISGNRFTYTVPPLTAYHIVLTTGNDTSPV-----     524
TTYGSGKVWGFDKNSSQIKEAAPITQISGNRFTYTVPPLTAYHIVLTAGNDT-PV-----    523
TTYSSGKIWGFDKNSSQIKAVAPITQISGNRFTYTVPPLTAYHIVLTADNDT-PVPPV      526
KTYSSGKVWGFDKNSSQIKEAAPITQISGNRFTYTVPPLTAYHIVLTTGNYTSPV-----    524
KTYTSGRVWGFDQTGSDITEQAAITNINNWQFTYTLPPLSAYHIVLKADSTE-------     521
KNYTIGNVWAFDRGSSNITQRTPIVNIKDNTFFTYTVPALTACHIVLEAAEPV-------    518
KNYTIGNVWAFDRGSSNITQRTPIVNIKDNTFFTYTVPALTACHIVLEAAEPV-------    518
KNYTSGQVWGFDSNSSNITKRDDVSSISGNKFTYKIPALTAVHIVLTTAQKS--------    518
KQYTSGRVWSFDRSSANITEKDAIDAISGNKLTYTIPALTVCHIVLDSSAQT--------    517
RVYTGGEIYGFDSTSSQIRKMGVLSNIQNNTITIEVPNLTVYHIVLTYHIVLR-------    525
TKYTKAEIYGFDSNSPDIRKMGNIDNIESNVFTLEVPNLTVYHIVLR-------------   525
PKYTKAEIYGFDSNSPEYKKMGNIDNIESNVFTLEVPKFNGVSHSITLDFNV--------    530
KDYKSAAVYAVYGDNDQVRLLDIVKDNKVNVELPAFSAAMVVSDDAAA------------   506
KSYKSAAVYAVFGDSEEIRLIDIIKDVKDNKVKTELPAFSAAMVVSDQADA---------    506
TAQAQAQVWQLTAANT--INHLSNVS-LSGSSLSLTLPAQSVTLLVIPASTAA-------    523
KTYTSGKVWGFDSNSSQITERAPITNISGNRFTYTVPALTAYHIVLTADNDTSPVPPV     573
TNQSKAEIYAVYKTNPNYKKMDNVSQVKDSKVSLEL-PFSVCMVSVSTSAPV--------   458
RK-KI-R---SLTRGGTEVRQAGILDDLES-TLNVKI-NQMGVSL-IESGEAA-------   339
PV-IQ-Q---Q-FGD-ED-NLLTA-VS-QW-VIKT---K----ALH--RDATYS------   214
..520.......530.......540.......550.......560.......570....
```

FIG. 1H

SEQUENCE LISTING

<160> NUMBER OF SEQ ID NOS: 23

<210> SEQ ID NO 1
<211> LENGTH: 1695
<212> TYPE: DNA
<213> ORGANISM: Paenibacillus polymyxa

<400> SEQUENCE: 1

```
atgaagaaac cgttggggaa aattgtcgca agcaccgcac tactcatttc tgttgctttt      60
agttcatcga tcgcatcggc tgtagttcac ggtcaaacgg caaagactat tactattaaa     120
gtagatacat tcaaggatcg taagcctatt agcccttata tatacggtac aaatcaggat     180
```

| | | |
|---|---|---|
| ttggcaggcg atgaaaatat ggctgccaga cgacttggtg gcaaccgaat gaccggatac | 240 |
| aactgggaaa acaatatgtc caatgcagga agtgactggc agcaatctag cgataactat | 300 |
| ttatgcagta atggtggcct gacacaagcc gaatgtgaaa agccaggagc ggtgacgact | 360 |
| tcgtttcatg accaatcgct gaagcttggc acttattctt tagttacgtt gccgatggcc | 420 |
| ggttatgtgg ctaaggatgg aaacggaagt gtgcaggaaa gcgaaaaggc cccttccgct | 480 |
| cgttggaatc aggtcgtaaa cgccaaaaat gcaccgttcc aactcagcc tgatctgaat | 540 |
| gacaatcggg tctatgtgga tgagttcgtc catttttag tgaacaagta cggcactgct | 600 |
| tcaacaaagg cggggtgaa aggatatgcc ctcgacaatg aacccgctct ctggtcgcat | 660 |
| acgcacccac gcattcatgg tgaaaagtc ggagcgaaag agttggtaga ccggtcagtc | 720 |
| agtttatcca agctgtgaa agcgattgac gcggggcag aggttttgg cccggttctt | 780 |
| tacggatttg gcgcctataa agatcttcaa actgcacctg attgggactc tgtaaaaggc | 840 |
| aattatagct ggttcgtaga ctattacctg gatcaaatgc gccttagctc gcaagtcgaa | 900 |
| ggcaagagat tgctggatgt attcgacgta cactggtatc cgaagcgat gggcggaggc | 960 |
| atacgaatta cgaatgaggt aggcaatgac gaaacgaaga agccagaat gcaggcacct | 1020 |
| cgcaccttgt gggacccgac ctataaggaa gatagttgga tcgctcaatg aacagcgag | 1080 |
| tttttgccca tactacctcg attgaagcag tcggtggata atattatcc gggaaccaag | 1140 |
| ctggcaatga ccgagtatag ctatggcggc gaaaatgata tttccggcgg gattgcgatg | 1200 |
| accgatgtgc tgggtatctt gggcaaaaat gatgtttata tggcaaacta ctggaagcta | 1260 |
| aaggatggtg tcaacaacta cgttagtgcc gcttacaagc tttatcgcaa ttatgacgga | 1320 |
| aaaaactcta ctttcggtga taccagtgtt agtgcgcaaa catcggatat tgtcaatagc | 1380 |
| tcggtccatg cttctgtaac gaatgcatcc gacaaagaac tgcatctcgt tgtcatgaat | 1440 |
| aaaagcatgg acagcgcatt cgacgcccaa tttgatcttt ccggcgcgaa gacttacatt | 1500 |
| tccggtaaag tatggggggtt cgataaaaac agctcgcaaa ttaaagaagc agcgccaatc | 1560 |
| acgcaaattt caggcaaccg ttttacttat accgtaccgc ctttgacggc atatcacatt | 1620 |
| gtgctgacta ctggcaatga cacgtctcca gtgtaaggcg tacttgtttg gggaaccgag | 1680 |
| ccgacagcta attaa | 1695 |

<210> SEQ ID NO 2
<211> LENGTH: 551
<212> TYPE: PRT
<213> ORGANISM: Paenibacillus polymyxa

<400> SEQUENCE: 2

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Val Val His Gly Gln
            20                  25                  30

Thr Ala Lys Thr Ile Thr Ile Lys Val Asp Thr Phe Lys Asp Arg Lys
        35                  40                  45

Pro Ile Ser Pro Tyr Ile Tyr Gly Thr Asn Gln Asp Leu Ala Gly Asp
    50                  55                  60

Glu Asn Met Ala Ala Arg Arg Leu Gly Gly Asn Arg Met Thr Gly Tyr
65                  70                  75                  80

Asn Trp Glu Asn Asn Met Ser Asn Ala Gly Ser Asp Trp Gln Gln Ser
                85                  90                  95

Ser Asp Asn Tyr Leu Cys Ser Asn Gly Gly Leu Thr Gln Ala Glu Cys
            100                 105                 110

```
Glu Lys Pro Gly Ala Val Thr Thr Ser Phe His Asp Gln Ser Leu Lys
            115                 120                 125
Leu Gly Thr Tyr Ser Leu Val Thr Leu Pro Met Ala Gly Tyr Val Ala
        130                 135                 140
Lys Asp Gly Asn Gly Ser Val Gln Glu Ser Lys Ala Pro Ser Ala
145                 150                 155                 160
Arg Trp Asn Gln Val Val Asn Ala Lys Asn Ala Pro Phe Gln Leu Gln
                165                 170                 175
Pro Asp Leu Asn Asp Asn Arg Val Tyr Val Asp Glu Phe Val His Phe
            180                 185                 190
Leu Val Asn Lys Tyr Gly Thr Ala Ser Thr Lys Ala Gly Val Lys Gly
        195                 200                 205
Tyr Ala Leu Asp Asn Glu Pro Ala Leu Trp Ser His Thr His Pro Arg
    210                 215                 220
Ile His Gly Glu Lys Val Gly Ala Lys Glu Leu Val Asp Arg Ser Val
225                 230                 235                 240
Ser Leu Ser Lys Ala Val Lys Ala Ile Asp Ala Gly Ala Glu Val Phe
                245                 250                 255
Gly Pro Val Leu Tyr Gly Phe Gly Ala Tyr Lys Asp Leu Gln Thr Ala
            260                 265                 270
Pro Asp Trp Asp Ser Val Lys Gly Asn Tyr Ser Trp Phe Val Asp Tyr
        275                 280                 285
Tyr Leu Asp Gln Met Arg Leu Ser Ser Gln Val Glu Gly Lys Arg Leu
    290                 295                 300
Leu Asp Val Phe Asp Val His Trp Tyr Pro Glu Ala Met Gly Gly Gly
305                 310                 315                 320
Ile Arg Ile Thr Asn Glu Val Gly Asn Asp Glu Thr Lys Lys Ala Arg
                325                 330                 335
Met Gln Ala Pro Arg Thr Leu Trp Asp Pro Thr Tyr Lys Glu Asp Ser
            340                 345                 350
Trp Ile Ala Gln Trp Asn Ser Glu Phe Leu Pro Ile Leu Pro Arg Leu
        355                 360                 365
Lys Gln Ser Val Asp Lys Tyr Tyr Pro Gly Thr Lys Leu Ala Met Thr
    370                 375                 380
Glu Tyr Ser Tyr Gly Gly Glu Asn Asp Ile Ser Gly Gly Ile Ala Met
385                 390                 395                 400
Thr Asp Val Leu Gly Ile Leu Gly Lys Asn Asp Val Tyr Met Ala Asn
                405                 410                 415
Tyr Trp Lys Leu Lys Asp Gly Val Asn Asn Tyr Val Ser Ala Ala Tyr
            420                 425                 430
Lys Leu Tyr Arg Asn Tyr Asp Gly Lys Asn Ser Thr Phe Gly Asp Thr
        435                 440                 445
Ser Val Ser Ala Gln Thr Ser Asp Ile Val Asn Ser Ser Val His Ala
    450                 455                 460
Ser Val Thr Asn Ala Ser Asp Lys Glu Leu His Leu Val Met Asn
465                 470                 475                 480
Lys Ser Met Asp Ser Ala Phe Asp Ala Gln Phe Asp Leu Ser Gly Ala
                485                 490                 495
Lys Thr Tyr Ile Ser Gly Lys Val Trp Gly Phe Asp Lys Asn Ser Ser
            500                 505                 510
Gln Ile Lys Glu Ala Ala Pro Ile Thr Gln Ile Ser Gly Asn Arg Phe
        515                 520                 525
Thr Tyr Thr Val Pro Pro Leu Thr Ala Tyr His Ile Val Leu Thr Thr
```

```
                    530                 535                 540
Gly Asn Asp Thr Ser Pro Val
545                 550

<210> SEQ ID NO 3
<211> LENGTH: 524
<212> TYPE: PRT
<213> ORGANISM: Paenibacillus polymyxa

<400> SEQUENCE: 3

Val Val His Gly Gln Thr Ala Lys Thr Ile Thr Ile Lys Val Asp Thr
1               5                   10                  15

Phe Lys Asp Arg Lys Pro Ile Ser Pro Tyr Ile Tyr Gly Thr Asn Gln
                20                  25                  30

Asp Leu Ala Gly Asp Glu Asn Met Ala Ala Arg Arg Leu Gly Gly Asn
            35                  40                  45

Arg Met Thr Gly Tyr Asn Trp Glu Asn Asn Met Ser Asn Ala Gly Ser
50                  55                  60

Asp Trp Gln Gln Ser Ser Asp Asn Tyr Leu Cys Ser Asn Gly Gly Leu
65                  70                  75                  80

Thr Gln Ala Glu Cys Glu Lys Pro Gly Ala Val Thr Thr Ser Phe His
                85                  90                  95

Asp Gln Ser Leu Lys Leu Gly Thr Tyr Ser Leu Val Thr Leu Pro Met
            100                 105                 110

Ala Gly Tyr Val Ala Lys Asp Gly Asn Gly Ser Val Gln Glu Ser Glu
        115                 120                 125

Lys Ala Pro Ser Ala Arg Trp Asn Gln Val Val Asn Ala Lys Asn Ala
130                 135                 140

Pro Phe Gln Leu Gln Pro Asp Leu Asn Asp Asn Arg Val Tyr Val Asp
145                 150                 155                 160

Glu Phe Val His Phe Leu Val Asn Lys Tyr Gly Thr Ala Ser Thr Lys
                165                 170                 175

Ala Gly Val Lys Gly Tyr Ala Leu Asp Asn Glu Pro Ala Leu Trp Ser
            180                 185                 190

His Thr His Pro Arg Ile His Gly Glu Lys Val Gly Ala Lys Glu Leu
        195                 200                 205

Val Asp Arg Ser Val Ser Leu Ser Lys Ala Val Lys Ala Ile Asp Ala
210                 215                 220

Gly Ala Glu Val Phe Gly Pro Val Leu Tyr Gly Phe Gly Ala Tyr Lys
225                 230                 235                 240

Asp Leu Gln Thr Ala Pro Asp Trp Asp Ser Val Lys Gly Asn Tyr Ser
                245                 250                 255

Trp Phe Val Asp Tyr Tyr Leu Asp Gln Met Arg Leu Ser Gln Val
            260                 265                 270

Glu Gly Lys Arg Leu Leu Asp Val Phe Asp Val His Trp Tyr Pro Glu
        275                 280                 285

Ala Met Gly Gly Gly Ile Arg Ile Thr Asn Glu Val Gly Asn Asp Glu
290                 295                 300

Thr Lys Lys Ala Arg Met Gln Ala Pro Arg Thr Leu Trp Asp Pro Thr
305                 310                 315                 320

Tyr Lys Glu Asp Ser Trp Ile Ala Gln Trp Asn Ser Glu Phe Leu Pro
                325                 330                 335

Ile Leu Pro Arg Leu Lys Gln Ser Val Asp Lys Tyr Tyr Pro Gly Thr
            340                 345                 350

Lys Leu Ala Met Thr Glu Tyr Ser Tyr Gly Gly Glu Asn Asp Ile Ser
```

```
                355                 360                 365
Gly Gly Ile Ala Met Thr Asp Val Leu Gly Ile Leu Gly Lys Asn Asp
    370                 375                 380
Val Tyr Met Ala Asn Tyr Trp Lys Leu Lys Asp Gly Val Asn Asn Tyr
385                 390                 395                 400
Val Ser Ala Ala Tyr Lys Leu Tyr Arg Asn Tyr Asp Gly Lys Asn Ser
                405                 410                 415
Thr Phe Gly Asp Thr Ser Val Ser Ala Gln Thr Ser Asp Ile Val Asn
            420                 425                 430
Ser Ser Val His Ala Ser Val Thr Asn Ala Ser Asp Lys Glu Leu His
            435                 440                 445
Leu Val Val Met Asn Lys Ser Met Asp Ser Ala Phe Asp Ala Gln Phe
        450                 455                 460
Asp Leu Ser Gly Ala Lys Thr Tyr Ile Ser Gly Lys Val Trp Gly Phe
465                 470                 475                 480
Asp Lys Asn Ser Ser Gln Ile Lys Glu Ala Ala Pro Ile Thr Gln Ile
                485                 490                 495
Ser Gly Asn Arg Phe Thr Tyr Thr Val Pro Pro Leu Thr Ala Tyr His
            500                 505                 510
Ile Val Leu Thr Thr Gly Asn Asp Thr Ser Pro Val
            515                 520
```

<210> SEQ ID NO 4
<211> LENGTH: 1590
<212> TYPE: DNA
<213> ORGANISM: Paenibacillus polymyxa

<400> SEQUENCE: 4

```
gtagttcacg gtcaaacggc aaagactgtt accattaaag tcgatacatc caaggatcgt      60
aagcctatta gcccttatat ttacggtacg aatcaggagt tggcaggcga tgagaatctg     120
actgccagac gacttggtgg caatcgaatg accggatata actgggaaaa caatatgtcc     180
aatgcaggaa gcgactggat gcagtccagc gatagctatt tatgcgacaa cgccggattg     240
acaaaagccg aatgtgaaaa gccaggtgcg gtggcaacct cgtttcacga tcaatcgctg     300
aagcagggca catattcttt agtcacactg ccgatggccg ttatgtggc caaggatgga     360
aacggaagtg tgcaggaaag cgaaaaggct ccttccgctc ggtggaatga ggtcgtaaac     420
gctaaaaatg cgccgtttca attgcagcct gatctgaaag acaatcaggt ttatgcggat     480
gaattcgtca acttttttagt gaaaaagtac ggcgttgctt caacaaaaac gggcgtgaaa     540
ggatactcgc tcgacaatga acccgctctc tggtcgcata cgcatccgcg cattcatggt     600
gaaaaggtcg gagcgaaaga gttggtagac cggtcggtaa gtttatccaa gccgctaag      660
gcggttgacg cgggtgcgga aattttttggg cccgttcttt acggttttgg cgcctataaa     720
gatcttcaaa ctgcacctga ttggaactct gtaaaaggca actacagctg gttcgtggac     780
tattacctcg atcaaatgcg cctcagctcg caagccgaag caagagatt gctggatgtc     840
ttcgatgtac actggtatcc tgaagcgatg gcgggaggca tacgaattac aaatgaggta     900
ggcaacgacg aaacgaagaa agccagaatg caagcgcctc gtactttgtg ggatccgacc     960
tacaaggaag atagctggat cgctcaatgg aacagtgaat tcttgccttt actgcctcga    1020
ttaaagcagt cggtggataa gtattacccg ggaaccaagc tggctttgac tgagtatagc    1080
tatggtggcg aaaatgatat ttccggcggt atcgctatgg ccgatgtgct ggcatcttg    1140
ggcaaaaacg acgtttatat ggcaaactac tggaagttaa aggatggtgc caacaactac    1200
```

```
gttagtgccg cttacaagct ttaccgcaat tatgacggaa aaagctctac tttcggtgat    1260
atcagcgttc atgcgcaaac gtcggatatt gttaatagct cggtgcatgc ttccgtaacg    1320
gatgcatcct acaaagaact gcacctcgtt gtcatgaata aaagcatgga cagtgcattc    1380
gacgcccaat ttgatctttc cggcgagacg acttacggtt ccgtaaagt atggggtttc     1440 gacaaaaata gctcgcaaat taaggaagca gcgccaatca cscaaatttc aggcaaccgy    1500
tttacctata cagtaccgcc tttgacggct tatcacatcg tgttgactgc cggcaatgat    1560
acacctgtag aaaatcctga aagctttgcg                                     1590
```

<210> SEQ ID NO 5
<211> LENGTH: 530
<212> TYPE: PRT
<213> ORGANISM: Paenibacillus polymyxa

<400> SEQUENCE: 5

```
Val Val His Gly Gln Thr Ala Lys Thr Val Thr Ile Lys Val Asp Thr
1               5                   10                  15

Ser Lys Asp Arg Lys Pro Ile Ser Pro Tyr Ile Tyr Gly Thr Asn Gln
            20                  25                  30

Glu Leu Ala Gly Asp Glu Asn Leu Thr Ala Arg Arg Leu Gly Gly Asn
        35                  40                  45

Arg Met Thr Gly Tyr Asn Trp Glu Asn Asn Met Ser Asn Ala Gly Ser
    50                  55                  60

Asp Trp Met Gln Ser Ser Asp Ser Tyr Leu Cys Asp Asn Ala Gly Leu
65                  70                  75                  80

Thr Lys Ala Glu Cys Glu Lys Pro Gly Ala Val Ala Thr Ser Phe His
                85                  90                  95

Asp Gln Ser Leu Lys Gln Gly Thr Tyr Ser Leu Val Thr Leu Pro Met
            100                 105                 110

Ala Gly Tyr Val Ala Lys Asp Gly Asn Gly Ser Val Gln Glu Ser Glu
        115                 120                 125

Lys Ala Pro Ser Ala Arg Trp Asn Glu Val Val Asn Ala Lys Asn Ala
    130                 135                 140

Pro Phe Gln Leu Gln Pro Asp Leu Lys Asp Asn Gln Val Tyr Ala Asp
145                 150                 155                 160

Glu Phe Val Asn Phe Leu Val Lys Lys Tyr Gly Val Ala Ser Thr Lys
                165                 170                 175

Thr Gly Val Lys Gly Tyr Ser Leu Asp Asn Glu Pro Ala Leu Trp Ser
            180                 185                 190

His Thr His Pro Arg Ile His Gly Glu Lys Val Gly Ala Lys Glu Leu
        195                 200                 205

Val Asp Arg Ser Val Ser Leu Ser Lys Ala Ala Lys Ala Val Asp Ala
    210                 215                 220

Gly Ala Glu Ile Phe Gly Pro Val Leu Tyr Gly Phe Gly Ala Tyr Lys
225                 230                 235                 240

Asp Leu Gln Thr Ala Pro Asp Trp Asn Ser Val Lys Gly Asn Tyr Ser
                245                 250                 255

Trp Phe Val Asp Tyr Tyr Leu Asp Gln Met Arg Leu Ser Ser Gln Ala
            260                 265                 270

Glu Gly Lys Arg Leu Leu Asp Val Phe Asp Val His Trp Tyr Pro Glu
        275                 280                 285

Ala Met Gly Gly Gly Ile Arg Ile Thr Asn Glu Val Gly Asn Asp Glu
    290                 295                 300

Thr Lys Lys Ala Arg Met Gln Ala Pro Arg Thr Leu Trp Asp Pro Thr
```

```
                    305                 310                 315                 320
Tyr Lys Glu Asp Ser Trp Ile Ala Gln Trp Asn Ser Glu Phe Leu Pro
                325                 330                 335

Leu Leu Pro Arg Leu Lys Gln Ser Val Asp Lys Tyr Tyr Pro Gly Thr
            340                 345                 350

Lys Leu Ala Leu Thr Glu Tyr Ser Tyr Gly Gly Glu Asn Asp Ile Ser
        355                 360                 365

Gly Gly Ile Ala Met Ala Asp Val Leu Gly Ile Leu Gly Lys Asn Asp
    370                 375                 380

Val Tyr Met Ala Asn Tyr Trp Lys Leu Lys Asp Gly Ala Asn Asn Tyr
385                 390                 395                 400

Val Ser Ala Ala Tyr Lys Leu Tyr Arg Asn Tyr Asp Gly Lys Ser Ser
                405                 410                 415

Thr Phe Gly Asp Ile Ser Val His Ala Gln Thr Ser Asp Ile Val Asn
            420                 425                 430

Ser Ser Val His Ala Ser Val Thr Asp Ala Ser Tyr Lys Glu Leu His
        435                 440                 445

Leu Val Val Met Asn Lys Ser Met Asp Ser Ala Phe Asp Ala Gln Phe
    450                 455                 460

Asp Leu Ser Gly Glu Thr Thr Tyr Gly Ser Gly Lys Val Trp Gly Phe
465                 470                 475                 480

Asp Lys Asn Ser Ser Gln Ile Lys Glu Ala Ala Pro Ile Thr Gln Ile
                485                 490                 495

Ser Gly Asn Arg Phe Thr Tyr Thr Val Pro Pro Leu Thr Ala Tyr His
            500                 505                 510

Ile Val Leu Thr Ala Gly Asn Asp Thr Pro Val Glu Asn Pro Glu Ser
        515                 520                 525

Phe Ala
    530

<210> SEQ ID NO 6
<211> LENGTH: 1575
<212> TYPE: DNA
<213> ORGANISM: Paenibacillus polymyxa

<400> SEQUENCE: 6
gtggttcacg gtcaaacggc aaagaccgtt accattaaag tcgatacatc caaggatcgt      60
aagcctatta gtccttatat atacggtacg aatcaggatt tggcaggcga tgaaaatctg     120
gctgccagac gacttggtgg caatcgaatg accggataca actgggaaaa taatatgtcc     180
aatgcgggaa gcgattggca gcaatccagc gataactttt tatgcaacaa tggtggcctg     240
acaaaagccg aatgtgaaaa gccgggagca gtgacgactc gtttcatga tcaatcgctg      300 aagctgggcg cttattcttt agtcacgctg ccgatggccg ttatgtggc caaggatgga      360 aacggaagtg tgcaggaaag cgaacaggct ccttccgctc gttggaatca ggtcgtaaat     420
gccaaaaatg cgccgttcca actacagcct gatctgaatg acaatcaggt atatgcggat     480
gaattcgtca attttttagt gaaaaagtac ggcgctgctt caacaaaggc gggtgtgaaa     540
ggatatgcgc tcgacaatga acccgctctc tggtcgcata cgcatccgcg cattcatggt     600
gaaaaggtcg gagcgaaaga gttggtagac cggtcggtaa gttatccaa agctgttaaa     660 gcggttgacg cgggtgcaga aatttttggg ccggttcttt acggttttgg cgcctataca     720
gatcttcaaa ctgcacctga ttggaactct gtaaaaggca actatagctg gttcgtggac     780
tattacctgg atcaaatgcg cctcaactcg caagccgarg gcaagagatt gctggaygta     840
```

```
ttcgatgtgc actggtatcc cgaagcgatg ggcggaggca tacgaattac aaatgaggta      900
ggcaatgacg aaacgaagaa agccagaatg caggcgcctc gtactttgtg ggaccccgacc     960 tacaaggaag atagctggat cgctcaatgg aacagcgcat tcttgccttt actgcctcga    1020
ttgaagcagt cggtgacaa gtattacccg ggaaccaagc tggctttgac cgagtatagc     1080
tacggcggcg aaaatgatat tccggcggt attgctatga ccgatgtgct gggcatcttg     1140
ggcaaaaacg acgtttatat ggcgaactat tggaagttaa aggatggtgc caacaactac    1200
gttagcgccg cttacaagct ttaccgcaat tatgacggaa aaaacgctac tttcggcgat    1260
atcagcgtta atgcgcaaac gtcggatatt gttaatagct cggtgcatgc ttccgtaacg    1320
gatgcatcct acaaagaact gcacctcatt gtcatgaata aaagcatgga cagcgcattc    1380
gacgcccaat tcgatctttc cggcgagacg acttacagtt ccggtaaaat atggggcttc    1440
gataaaaata gctcgcaaat taaggcagta gcgccaatca cgcaaatttc aggcaaccgc    1500
tttacctata cagtaccacc tttgacggct tatcacatcg tgttgactgc cgacaatgat    1560
acacctgtgc cataa                                                     1575
```

<210> SEQ ID NO 7
<211> LENGTH: 524
<212> TYPE: PRT
<213> ORGANISM: Paenibacillus polymyxa

<400> SEQUENCE: 7

```
Val Val His Gly Gln Thr Ala Lys Thr Val Thr Ile Lys Val Asp Thr
1               5                   10                  15

Ser Lys Asp Arg Lys Pro Ile Ser Pro Tyr Ile Tyr Gly Thr Asn Gln
            20                  25                  30

Asp Leu Ala Gly Asp Glu Asn Leu Ala Ala Arg Arg Leu Gly Gly Asn
        35                  40                  45

Arg Met Thr Gly Tyr Asn Trp Glu Asn Asn Met Ser Asn Ala Gly Ser
50                  55                  60

Asp Trp Gln Gln Ser Ser Asp Asn Phe Leu Cys Asn Asn Gly Gly Leu
65                  70                  75                  80

Thr Lys Ala Glu Cys Glu Lys Pro Gly Ala Val Thr Thr Ser Phe His
                85                  90                  95

Asp Gln Ser Leu Lys Leu Gly Ala Tyr Ser Leu Val Thr Leu Pro Met
            100                 105                 110

Ala Gly Tyr Val Ala Lys Asp Gly Asn Gly Ser Val Gln Glu Ser Glu
        115                 120                 125

Gln Ala Pro Ser Ala Arg Trp Asn Gln Val Val Asn Ala Lys Asn Ala
130                 135                 140

Pro Phe Gln Leu Gln Pro Asp Leu Asn Asp Asn Gln Val Tyr Ala Asp
145                 150                 155                 160

Glu Phe Val Asn Phe Leu Val Lys Lys Tyr Gly Ala Ala Ser Thr Lys
                165                 170                 175

Ala Gly Val Lys Gly Tyr Ala Leu Asp Asn Glu Pro Ala Leu Trp Ser
            180                 185                 190

His Thr His Pro Arg Ile His Gly Glu Lys Val Gly Ala Lys Glu Leu
        195                 200                 205

Val Asp Arg Ser Val Ser Leu Ser Lys Ala Val Lys Ala Val Asp Ala
210                 215                 220

Gly Ala Glu Ile Phe Gly Pro Val Leu Tyr Gly Phe Gly Ala Tyr Thr
225                 230                 235                 240

Asp Leu Gln Thr Ala Pro Asp Trp Asn Ser Val Lys Gly Asn Tyr Ser
```

```
            245                 250                 255
Trp Phe Val Asp Tyr Tyr Leu Asp Gln Met Arg Leu Asn Ser Gln Ala
            260                 265                 270

Glu Gly Lys Arg Leu Leu Asp Val Phe Asp Val His Trp Tyr Pro Glu
            275                 280                 285

Ala Met Gly Gly Gly Ile Arg Ile Thr Asn Glu Val Gly Asn Asp Glu
            290                 295                 300

Thr Lys Lys Ala Arg Met Gln Ala Pro Arg Thr Leu Trp Asp Pro Thr
305                 310                 315                 320

Tyr Lys Glu Asp Ser Trp Ile Ala Gln Trp Asn Ser Ala Phe Leu Pro
                325                 330                 335

Leu Leu Pro Arg Leu Lys Gln Ser Val Asp Lys Tyr Tyr Pro Gly Thr
                340                 345                 350

Lys Leu Ala Leu Thr Glu Tyr Ser Tyr Gly Gly Glu Asn Asp Ile Ser
                355                 360                 365

Gly Gly Ile Ala Met Thr Asp Val Leu Gly Ile Leu Gly Lys Asn Asp
            370                 375                 380

Val Tyr Met Ala Asn Tyr Trp Lys Leu Lys Asp Gly Ala Asn Asn Tyr
385                 390                 395                 400

Val Ser Ala Ala Tyr Lys Leu Tyr Arg Asn Tyr Asp Gly Lys Asn Ala
                405                 410                 415

Thr Phe Gly Asp Ile Ser Val Asn Ala Gln Thr Ser Asp Ile Val Asn
                420                 425                 430

Ser Ser Val His Ala Ser Val Thr Asp Ala Ser Tyr Lys Glu Leu His
                435                 440                 445

Leu Ile Val Met Asn Lys Ser Met Asp Ser Ala Phe Asp Ala Gln Phe
450                 455                 460

Asp Leu Ser Gly Glu Thr Thr Tyr Ser Ser Gly Lys Ile Trp Gly Phe
465                 470                 475                 480

Asp Lys Asn Ser Ser Gln Ile Lys Ala Val Ala Pro Ile Thr Gln Ile
                485                 490                 495

Ser Gly Asn Arg Phe Thr Tyr Thr Val Pro Pro Leu Thr Ala Tyr His
                500                 505                 510

Ile Val Leu Thr Ala Asp Asn Asp Thr Pro Val Pro
            515                 520

<210> SEQ ID NO 8
<211> LENGTH: 524
<212> TYPE: PRT
<213> ORGANISM: Artificial sequence
<220> FEATURE:
<223> OTHER INFORMATION: Synthetic construct

<400> SEQUENCE: 8

Val Val His Gly Gln Thr Ala Lys Thr Ile Thr Ile Lys Val Asp Thr
1               5                   10                  15

Ser Lys Glu Arg Lys Pro Ile Ser Pro Tyr Ile Tyr Gly Thr Asn Gln
                20                  25                  30

Asp Leu Ala Gly Asp Glu Asn Met Ala Ala Arg Arg Leu Gly Gly Asn
            35                  40                  45

Arg Met Thr Gly Tyr Asn Trp Glu Asn Asn Met Ser Asn Ala Gly Ser
50                  55                  60

Asp Trp Gln Gln Ser Ser Asp Asn Tyr Leu Cys Ser Asn Gly Gly Leu
65                  70                  75                  80

Thr Gln Ala Glu Cys Glu Lys Pro Gly Ala Val Thr Thr Ser Phe His
                85                  90                  95
```

-continued

Asp Gln Ser Leu Lys Leu Gly Thr Tyr Ser Leu Val Thr Leu Pro Met
            100                 105                 110

Ala Gly Tyr Val Ala Lys Asp Gly Asn Gly Ser Val Gln Glu Ser Glu
            115                 120                 125

Lys Ala Pro Ser Ala Arg Trp Asn Gln Val Val Asn Ala Lys Asn Thr
130                 135                 140

Pro Phe Gln Leu Gln Pro Asp Leu Asn Asp Asn Arg Val Tyr Val Asp
145                 150                 155                 160

Glu Phe Val His Phe Leu Val Asn Lys Tyr Gly Thr Ala Ser Thr Lys
                165                 170                 175

Ala Gly Val Lys Gly Tyr Ala Leu Asp Asn Glu Pro Ala Leu Trp Ser
            180                 185                 190

His Thr His Pro Arg Ile His Gly Glu Lys Val Gly Ala Lys Glu Leu
            195                 200                 205

Val Asp Arg Ser Val Ser Leu Ser Lys Ala Val Lys Ala Ile Asp Ala
            210                 215                 220

Gly Ala Glu Ile Phe Gly Pro Val Leu Tyr Gly Phe Gly Ala Tyr Lys
225                 230                 235                 240

Asp Leu Gln Thr Ala Pro Asp Trp Asp Ser Val Lys Gly Asn Tyr Ser
                245                 250                 255

Trp Phe Val Asp Tyr Tyr Leu Asp Gln Met Arg Leu Ser Ser Gln Ala
            260                 265                 270

Glu Gly Lys Arg Leu Leu Asp Val Phe Asp Val His Trp Tyr Pro Glu
            275                 280                 285

Ala Met Gly Gly Gly Ile Arg Ile Thr Asn Glu Val Gly Asn Asp Glu
            290                 295                 300

Thr Lys Lys Ala Arg Met Gln Ala Pro Arg Thr Leu Trp Asp Pro Thr
305                 310                 315                 320

Tyr Lys Glu Asp Ser Trp Ile Ala Gln Trp Asn Ser Glu Phe Leu Pro
                325                 330                 335

Ile Leu Pro Arg Leu Lys Gln Ser Val Asp Lys Tyr Tyr Pro Gly Thr
            340                 345                 350

Lys Leu Ala Met Thr Glu Tyr Ser Tyr Gly Gly Glu Asn Asp Ile Ser
            355                 360                 365

Gly Gly Ile Ala Met Thr Asp Val Leu Gly Ile Leu Gly Lys Asn Asp
            370                 375                 380

Val Tyr Met Ala Asn Tyr Trp Lys Leu Lys Asp Gly Val Asn Asn Tyr
385                 390                 395                 400

Val Ser Pro Ala Tyr Lys Leu Tyr Arg Asn Tyr Asp Gly Lys Asn Ser
                405                 410                 415

Thr Phe Gly Asp Thr Ser Val Ser Ala Gln Thr Ser Asp Ile Val Asn
            420                 425                 430

Ser Ser Val His Ala Ser Val Thr Asn Ala Ser Asp Lys Glu Leu His
            435                 440                 445

Leu Val Val Met Asn Lys Ser Met Asp Ser Ala Phe Asp Ala Gln Phe
            450                 455                 460

Asp Leu Ser Gly Ala Lys Thr Tyr Ser Ser Gly Lys Val Trp Gly Phe
465                 470                 475                 480

Asp Lys Asn Ser Ser Gln Ile Lys Glu Ala Ala Pro Ile Thr Gln Ile
                485                 490                 495

Ser Gly Asn Arg Phe Thr Tyr Thr Val Pro Pro Leu Thr Ala Tyr His
            500                 505                 510

Ile Val Leu Thr Thr Gly Asn Tyr Thr Ser Pro Val

<210> SEQ ID NO 9
<211> LENGTH: 521
<212> TYPE: PRT
<213> ORGANISM: Artificial sequence
<220> FEATURE:
<223> OTHER INFORMATION: Synthetic construct

<400> SEQUENCE: 9

```
Ala Ser Val Asn Ala Ala Ser Asp Val Thr Phe Thr Ile Asn Thr
1               5                   10                  15

Gln Ser Glu Arg Ala Ala Ile Ser Pro Asn Ile Tyr Gly Thr Asn Gln
            20                  25                  30

Asp Leu Ser Gly Thr Glu Asn Trp Ser Ser Arg Arg Leu Gly Gly Asn
        35                  40                  45

Arg Leu Thr Gly Tyr Asn Trp Glu Asn Asn Ala Ser Ser Ala Gly Arg
    50                  55                  60

Asp Trp Leu His Tyr Ser Asp Asp Phe Leu Cys Gly Asn Gly Gly Val
65                  70                  75                  80

Pro Asp Thr Asp Cys Asp Lys Pro Gly Ala Val Val Thr Ala Phe His
                85                  90                  95

Asp Lys Ser Leu Glu Asn Gly Ala Tyr Ser Ile Val Thr Leu Gln Met
            100                 105                 110

Ala Gly Tyr Val Ser Arg Asp Lys Asn Gly Pro Val Asp Glu Ser Glu
        115                 120                 125

Thr Ala Pro Ser Pro Arg Trp Asp Lys Val Glu Phe Ala Lys Asn Ala
    130                 135                 140

Pro Phe Ser Leu Gln Pro His Leu Asn Asp Gly Gln Val Tyr Met Asp
145                 150                 155                 160

Glu Glu Val Asn Phe Leu Val Asn Arg Tyr Gly Asn Ala Ser Thr Ser
                165                 170                 175

Thr Gly Ile Lys Ala Tyr Ser Leu Asp Asn Glu Pro Ala Leu Trp Ser
            180                 185                 190

Glu Thr His Pro Arg Ile His Pro Glu Gln Leu Gln Ala Ala Glu Leu
        195                 200                 205

Val Ala Lys Ser Ile Asp Leu Ser Lys Ala Val Lys Asn Val Asp Pro
    210                 215                 220

His Ala Glu Ile Phe Gly Pro Ala Leu Tyr Gly Phe Gly Ala Tyr Leu
225                 230                 235                 240

Ser Leu Gln Asp Ala Pro Gly Trp Pro Ser Leu Gln Gly Asn Tyr Ser
                245                 250                 255

Trp Phe Ile Asp Tyr Tyr Leu Asp Gln Met Lys Asn Ala His Thr Gln
            260                 265                 270

Asn Gly Lys Arg Leu Leu Asp Val Leu Asp Val His Trp Tyr Pro Glu
        275                 280                 285

Ala Gln Gly Gly Gly Gln Arg Ile Val Phe Gly Gly Ala Gly Asn Ile
    290                 295                 300

Asp Thr Gln Lys Ala Arg Val Gln Ala Pro Arg Ser Leu Trp Asp Pro
305                 310                 315                 320

Ala Tyr Gln Glu Asp Ser Trp Ile Gly Thr Trp Phe Ser Ser Tyr Leu
                325                 330                 335

Pro Leu Ile Pro Lys Leu Gln Ser Ser Ile Gln Thr Tyr Tyr Pro Gly
            340                 345                 350

Thr Lys Leu Ala Ile Thr Glu Ser Ser Tyr Gly Gly Asp Asn His Ile
        355                 360                 365
```

```
Ser Gly Gly Ile Ala Thr Ala Asp Ala Leu Gly Ile Phe Lys Tyr
    370                 375                 380

Gly Val Tyr Ala Ala Asn Tyr Trp Gln Thr Glu Asp Asn Thr Asp Tyr
385                 390                 395                 400

Thr Ser Ala Ala Tyr Lys Leu Tyr Arg Asn Tyr Asp Gly Asn Lys Ser
                405                 410                 415

Gly Phe Gly Ser Ile Lys Val Asp Ala Ala Thr Ser Asp Thr Glu Asn
                420                 425                 430

Ser Ser Val Tyr Ala Ser Val Thr Asp Glu Glu Asn Ser Glu Leu His
            435                 440                 445

Leu Ile Val Leu Asn Lys Asn Phe Asp Asp Pro Ile Asn Ala Thr Phe
            450                 455                 460

Gln Leu Ser Gly Asp Lys Thr Tyr Thr Ser Gly Arg Val Trp Gly Phe
465                 470                 475                 480

Asp Gln Thr Gly Ser Asp Ile Thr Glu Gln Ala Ala Ile Thr Asn Ile
                485                 490                 495

Asn Asn Asn Gln Phe Thr Tyr Thr Leu Pro Pro Leu Ser Ala Tyr His
                500                 505                 510

Ile Val Leu Lys Ala Asp Ser Thr Glu
            515                 520

<210> SEQ ID NO 10
<211> LENGTH: 518
<212> TYPE: PRT
<213> ORGANISM: Artificial sequence
<220> FEATURE:
<223> OTHER INFORMATION: Synthetic construct

<400> SEQUENCE: 10

Pro Thr Glu Pro Ala Lys Val Val Asp Ile Arg Ile Asp Thr Ser Ala
1               5                   10                  15

Glu Arg Lys Pro Ile Ser Pro Tyr Ile Tyr Gly Ser Asn Gln Glu Leu
                20                  25                  30

Asp Ala Thr Val Thr Ala Lys Arg Phe Gly Gly Asn Arg Thr Thr Gly
            35                  40                  45

Tyr Asn Trp Glu Asn Asn Phe Ser Asn Ala Gly Ser Asp Trp Leu His
    50                  55                  60

Tyr Ser Asp Thr Tyr Leu Leu Glu Asp Gly Val Pro Lys Gly Glu
65                  70                  75                  80

Trp Ser Thr Pro Ala Ser Val Val Thr Thr Phe His Asp Lys Ala Leu
                85                  90                  95

Ser Lys Asn Val Pro Tyr Thr Leu Ile Thr Leu Gln Ala Ala Gly Tyr
            100                 105                 110

Val Ser Ala Asp Gly Asn Gly Pro Val Ser Gln Glu Glu Thr Ala Pro
        115                 120                 125

Ser Ser Arg Trp Lys Glu Val Lys Phe Glu Lys Gly Ala Pro Phe Ser
    130                 135                 140

Leu Thr Pro Asp Thr Glu Asp Asp Tyr Val Tyr Met Asp Glu Phe Val
145                 150                 155                 160

Asn Tyr Leu Val Asn Lys Tyr Gly Asn Ala Ser Thr Pro Thr Gly Ile
                165                 170                 175

Lys Gly Tyr Ser Ile Asp Asn Glu Pro Ala Leu Trp Ser His Thr His
            180                 185                 190

Pro Arg Ile His Pro Asp Asn Val Thr Ala Lys Glu Leu Ile Glu Lys
        195                 200                 205
```

Ser Val Ala Leu Ser Lys Ala Val Lys Lys Val Asp Pro Tyr Ala Glu
    210                 215                 220

Ile Phe Gly Pro Ala Leu Tyr Gly Phe Ala Ala Tyr Glu Thr Leu Gln
225                 230                 235                 240

Ser Ala Pro Asp Trp Gly Thr Glu Gly Glu Gly Tyr Arg Trp Phe Ile
                    245                 250                 255

Asp Tyr Tyr Leu Asp Lys Met Lys Lys Ala Ser Asp Glu Glu Gly Lys
                260                 265                 270

Arg Leu Leu Asp Val Leu Asp Val His Trp Tyr Pro Glu Ala Arg Gly
            275                 280                 285

Gly Gly Glu Arg Ile Cys Phe Gly Ala Asp Pro Arg Asn Ile Glu Thr
        290                 295                 300

Asn Lys Ala Arg Leu Gln Ala Pro Arg Thr Leu Trp Asp Pro Thr Tyr
305                 310                 315                 320

Ile Glu Asp Ser Trp Ile Gly Gln Trp Lys Lys Asp Phe Leu Pro Ile
                325                 330                 335

Leu Pro Asn Leu Leu Asp Ser Ile Glu Lys Tyr Tyr Pro Gly Thr Lys
                340                 345                 350

Leu Ala Ile Thr Glu Tyr Asp Tyr Gly Gly Gly Asn His Ile Thr Gly
            355                 360                 365

Gly Ile Ala Gln Ala Asp Val Leu Gly Ile Phe Gly Lys Tyr Gly Val
        370                 375                 380

Tyr Leu Ala Thr Phe Trp Gly Asp Ala Ser Asn Asn Tyr Thr Glu Ala
385                 390                 395                 400

Gly Ile Asn Leu Tyr Thr Asn Tyr Asp Gly Lys Gly Gly Lys Phe Gly
                405                 410                 415

Asp Thr Ser Val Lys Cys Glu Thr Ser Asp Ile Glu Val Ser Ser Ala
                420                 425                 430

Tyr Ala Ser Ile Val Gly Glu Asp Asp Ser Lys Leu His Ile Ile Leu
            435                 440                 445

Leu Asn Lys Asn Tyr Asp Gln Pro Thr Thr Phe Asn Phe Ser Ile Asp
        450                 455                 460

Ser Ser Lys Asn Tyr Thr Ile Gly Asn Val Trp Ala Phe Asp Arg Gly
465                 470                 475                 480

Ser Ser Asn Ile Thr Gln Arg Thr Pro Ile Val Asn Ile Lys Asp Asn
                485                 490                 495

Thr Phe Thr Tyr Thr Val Pro Ala Leu Thr Ala Cys His Ile Val Leu
                500                 505                 510

Glu Ala Ala Glu Pro Val
            515

<210> SEQ ID NO 11
<211> LENGTH: 518
<212> TYPE: PRT
<213> ORGANISM: Artificial sequence
<220> FEATURE:
<223> OTHER INFORMATION: Synthetic construct

<400> SEQUENCE: 11

Pro Thr Glu Pro Ala Lys Val Val Asp Ile Arg Ile Asp Thr Ser Ala
1               5                   10                  15

Glu Arg Lys Pro Ile Ser Pro Tyr Ile Tyr Gly Ser Asn Gln Glu Leu
                20                  25                  30

Asp Ala Thr Val Thr Ala Lys Arg Phe Gly Gly Asn Arg Thr Thr Gly
            35                  40                  45

Tyr Asn Trp Glu Asn Asn Phe Ser Asn Ala Gly Ser Asp Trp Leu His

-continued

```
                50                  55                  60
Tyr Ser Asp Thr Tyr Leu Leu Glu Asp Gly Gly Val Pro Lys Gly Glu
65                  70                  75                  80

Trp Ser Thr Pro Ala Ser Val Val Thr Thr Phe His Asp Lys Ala Leu
                85                  90                  95

Ser Lys Asn Val Pro Tyr Thr Leu Ile Thr Leu Gln Ala Ala Gly Tyr
                100                 105                 110

Val Ser Ala Asp Gly Asn Gly Pro Val Ser Gln Glu Thr Ala Pro
                115                 120                 125

Ser Ser Arg Trp Lys Glu Val Lys Phe Glu Lys Gly Ala Pro Phe Ser
                130                 135                 140

Leu Thr Pro Asp Thr Glu Asp Asp Tyr Val Tyr Met Asp Glu Phe Val
145                 150                 155                 160

Asn Tyr Leu Val Asn Lys Tyr Gly Asn Ala Ser Thr Pro Thr Gly Ile
                165                 170                 175

Lys Gly Tyr Ser Ile Asp Asn Glu Pro Ala Leu Trp Ser His Thr His
                180                 185                 190

Pro Arg Ile His Pro Asp Asn Val Thr Ala Lys Glu Leu Ile Glu Lys
                195                 200                 205

Ser Val Ala Leu Ser Lys Ala Val Lys Val Asp Pro Tyr Ala Glu
210                 215                 220

Ile Phe Gly Pro Ala Leu Tyr Gly Phe Ala Ala Tyr Glu Thr Leu Gln
225                 230                 235                 240

Ser Ala Pro Asp Trp Gly Thr Glu Gly Glu Gly Tyr Arg Trp Phe Ile
                245                 250                 255

Asp Tyr Tyr Leu Asp Lys Met Lys Lys Ala Ser Asp Glu Glu Gly Lys
                260                 265                 270

Arg Leu Leu Asp Val Leu Asp Val His Trp Tyr Pro Glu Ala Arg Gly
                275                 280                 285

Gly Gly Glu Arg Ile Cys Phe Gly Ala Asp Pro Arg Asn Ile Glu Thr
                290                 295                 300

Asn Lys Ala Arg Leu Gln Ala Pro Arg Thr Leu Trp Asp Pro Thr Tyr
305                 310                 315                 320

Ile Glu Asp Ser Trp Ile Gly Gln Trp Lys Lys Asp Phe Leu Pro Ile
                325                 330                 335

Leu Pro Asn Leu Leu Asp Ser Ile Glu Lys Tyr Tyr Pro Gly Thr Lys
                340                 345                 350

Leu Ala Ile Thr Glu Tyr Asp Tyr Gly Gly Gly Asn His Ile Thr Gly
                355                 360                 365

Gly Ile Ala Gln Ala Asp Val Leu Gly Ile Phe Gly Lys Tyr Gly Val
370                 375                 380

Tyr Leu Ala Thr Phe Trp Gly Asp Ala Ser Asn Asn Tyr Thr Glu Ala
385                 390                 395                 400

Gly Ile Asn Leu Tyr Thr Asn Tyr Asp Gly Lys Gly Lys Phe Gly
                405                 410                 415

Asp Thr Ser Val Lys Cys Glu Thr Ser Asp Ile Glu Val Ser Ser Ala
                420                 425                 430

Tyr Ala Ser Ile Val Gly Glu Asp Asp Ser Lys Leu His Ile Ile Leu
                435                 440                 445

Leu Asn Lys Asn Tyr Asp Gln Pro Thr Thr Phe Asn Phe Ser Ile Asp
                450                 455                 460

Ser Ser Lys Asn Tyr Thr Ile Gly Asn Val Trp Ala Phe Asp Arg Gly
465                 470                 475                 480
```

-continued

Ser Ser Asn Ile Thr Gln Arg Thr Pro Ile Val Asn Ile Lys Asp Asn
            485                 490                 495

Thr Phe Thr Tyr Thr Val Pro Ala Leu Thr Ala Cys His Ile Val Leu
            500                 505                 510

Glu Ala Ala Glu Pro Val
            515

<210> SEQ ID NO 12
<211> LENGTH: 518
<212> TYPE: PRT
<213> ORGANISM: Artificial sequence
<220> FEATURE:
<223> OTHER INFORMATION: Synthetic construct

<400> SEQUENCE: 12

Ala Asp Thr Ala Asp Val Asn Val Asn Ile Asp Thr Asn Ala Glu Lys
1               5                   10                  15

Gln Ala Ile Ser Pro Tyr Ile Tyr Gly Thr Asn Gln Asp Phe Ser Asn
            20                  25                  30

Ala Lys Val Thr Ala Arg Arg Ile Gly Gly Asn Arg Ser Thr Gly Tyr
            35                  40                  45

Asn Trp Glu Asn Asn Asp Ser Asn Ala Gly Thr Asp Trp Lys Asn Glu
50                  55                  60

Ser Asp Asn Tyr Trp Leu Thr Leu Tyr Asp Val Pro Lys Glu Lys Tyr
65                  70                  75                  80

Asn Glu Pro Ala Ser Val Tyr Thr Ala Phe His Asp Lys Ser Leu Ala
            85                  90                  95

Met Gly Val Pro Tyr Ser Leu Val Thr Leu Gln Ala Gly Gly Tyr Val
            100                 105                 110

Ala Ala Asp Gln Ser Gly Pro Leu Ala Asn Thr Asp Val Ala Pro Ser
            115                 120                 125

Ser Lys Trp Lys Lys Val Glu Phe Asn Lys Asn Gly Pro Leu Ser Leu
            130                 135                 140

Thr Pro Asp Thr Thr Asp Gly Ser Val Tyr Met Asp Glu Phe Val Asn
145                 150                 155                 160

Tyr Leu Val Asn Lys Tyr Gly Ser Ala Ser Gly Ser Lys Gly Ile Lys
            165                 170                 175

Gly Tyr Ser Leu Asp Asn Glu Pro Ser Leu Trp Pro Ser Thr His Pro
            180                 185                 190

Leu Ile His Pro Asp Lys Thr Lys Cys Ser Glu Val Leu Asp Lys Asp
            195                 200                 205

Thr Gln Leu Ala Gln Val Val Lys Lys Ile Asp Pro Ala Ala Glu Thr
            210                 215                 220

Phe Gly Pro Ala Leu Phe Gly Phe Ser Ala Phe Asn Asp Phe Asn Ser
225                 230                 235                 240

Ser Pro Asp Trp Ser Ser Val Lys Gly Asn Tyr Gln Trp Phe Ile Asp
            245                 250                 255

Tyr Tyr Leu Asp Asn Met Lys Lys Asn Ser Asp Ala Ala Gly Lys Arg
            260                 265                 270

Leu Leu Asp Ala Leu Asp Leu His Trp Tyr Pro Glu Ala Lys Gly Gly
            275                 280                 285

Gly Gln Arg Val Thr Thr Ser Asp Thr Ser Asn Val Asp Cys Asn Lys
            290                 295                 300

Ala Arg Met Gln Ala Pro Arg Ser Leu Trp Asp Ser Thr Tyr Thr Glu
305                 310                 315                 320

Asp Ser Trp Ile Gly Gln Trp Cys Lys Trp Gly Leu Pro Leu Ile Pro

```
                325                 330                 335
Lys Val Lys Ser Ser Ile Asp Lys Tyr Tyr Pro Gly Thr Lys Leu Ser
            340                 345                 350

Phe Ser Glu Tyr Asn Tyr Gly Gly Glu Asp His Ile Ser Gly Gly Ile
            355                 360                 365

Ala Gln Ala Asp Ala Leu Gly Val Phe Gly Lys Tyr Gly Val Tyr Phe
            370                 375                 380

Ala Thr Tyr Trp Glu Cys Asn Ser Asp Lys Asn Asn Tyr Val Gln Ser
385                 390                 395                 400

Ala Phe Asn Leu Tyr Asn Asn Tyr Asp Gly Asn Asn Ser Lys Tyr Gly
            405                 410                 415

Asp Thr Asp Val Lys Cys Asp Thr Ser Asp Ile Asn Asn Ser Ser Thr
            420                 425                 430

Tyr Ala Ser Val Thr Ser Asn Asp Gly Asn Lys Met Asp Ile Ile Val
            435                 440                 445

Met Asn Lys Asn Tyr Thr Asp Ser Ile Asn Phe Asn Phe Asn Val Ser
            450                 455                 460

Ser Asn Lys Asn Tyr Thr Ser Gly Gln Val Trp Gly Phe Asp Ser Asn
465                 470                 475                 480

Ser Ser Asn Ile Thr Lys Arg Asp Asp Val Ser Ser Ile Ser Gly Asn
            485                 490                 495

Lys Phe Thr Tyr Lys Ile Pro Ala Leu Thr Ala Val His Ile Val Leu
            500                 505                 510

Thr Thr Ala Gln Lys Ser
            515

<210> SEQ ID NO 13
<211> LENGTH: 502
<212> TYPE: PRT
<213> ORGANISM: Artificial sequence
<220> FEATURE:
<223> OTHER INFORMATION: Synthetic construct

<400> SEQUENCE: 13

Ser Ala Ala Ser Asp Ala Ile Asn Val Ser Ile Asp Thr Thr Ala
1               5                   10                  15

Glu Arg Ala Ala Ile Ser Pro Tyr Ile Tyr Gly Gly Asn Trp Glu Phe
            20                  25                  30

Asn Asn Ala Lys Leu Thr Ala Lys Arg Phe Gly Gly Asn Arg Thr Thr
            35                  40                  45

Gly Tyr Asn Trp Glu Asn Asn Tyr Ser Asn Ala Gly Ser Asp Trp Gln
50                  55                  60

Gln Ser Ser Asp Thr Tyr Met Leu Thr Ser Asn Lys Ile Pro Glu Asp
65                  70                  75                  80

Lys Trp Ser Glu Pro Gly Val Val Ile Thr Asp Phe His Asp Lys Asn
            85                  90                  95

Leu Ala Ala Gly Glu Pro Tyr Ser Leu Val Thr Leu Gln Ala Ala Gly
            100                 105                 110

Tyr Val Ser Ala Asp Ala Asn Gly Thr Val Ala Glu Asp Glu Val Ala
            115                 120                 125

Pro Ser Glu Arg Trp Lys Glu Val Lys Phe Lys Lys Asp Ala Pro Leu
            130                 135                 140

Ser Leu Thr Pro Asp Thr Thr Asp Asn Tyr Val Tyr Met Asp Glu Leu
145                 150                 155                 160

Val Asn Leu Leu Val Asn Lys Tyr Gly Ser Ala Ser Thr Ala Thr Gly
            165                 170                 175
```

```
Ile Lys Gly Tyr Ala Ile Asp Asn Glu Pro Ala Leu Trp Ser Gly Thr
            180                 185                 190

His Pro Arg Met His Pro Asn Asn Ala Thr Cys Ala Glu Val Ile Asp
        195                 200                 205

Lys Asn Ile Asn Leu Ala Lys Thr Val Lys Gly Val Asp Pro Ser Ala
210                 215                 220

Glu Thr Phe Gly Leu Val Ala Tyr Gly Phe Ala Ala Tyr Asn Asp Phe
225                 230                 235                 240

Gln Ser Ala Thr Asp Trp Lys Asp Leu Lys Gly Asn Tyr Thr Trp Phe
            245                 250                 255

Leu Asp Tyr Tyr Leu Asp Ser Met Lys Lys Ala Ser Thr Glu Ala Gly
        260                 265                 270

Thr Arg Leu Ile Asp Ala Leu Asp Leu His Trp Tyr Pro Glu Ala Lys
        275                 280                 285

Gly Gly Gly Gln Arg Ile Cys Phe Gly Glu Asp Pro Thr Asn Ile Leu
290                 295                 300

Cys Asn Lys Ala Arg Leu Gln Ala Ala Arg Thr Leu Trp Asp Pro Thr
305                 310                 315                 320

Tyr Lys Glu Asp Ser Trp Ile Ala Gln Trp Cys Ser Phe Gly Leu Pro
                325                 330                 335

Leu Ile Pro Lys Val Gln Glu Ser Ile Asp Lys Tyr Asn Pro Gly Thr
            340                 345                 350

Lys Leu Ala Phe Thr Glu Tyr Ser Tyr Gly Ala Asp Asn His Ile Thr
        355                 360                 365

Gly Gly Ile Ala Glu Ala Asp Val Leu Gly Val Phe Gly Lys Tyr Gly
        370                 375                 380

Val Tyr Leu Ala Thr Val Trp Gly Gly Ser Tyr Thr Ala Ala Gly
385                 390                 395                 400

Val Asn Ile Tyr Thr Asn Tyr Asp Gly Asn Gly Ser Lys Tyr Gly Asp
                405                 410                 415

Thr Lys Val Lys Ala Glu Thr Ser Asp Val Glu Asn Ser Ser Val Tyr
            420                 425                 430

Ala Ser Val Asp Ser Lys Asp Ser Lys Leu His Val Ile Leu Ile
        435                 440                 445

Asn Lys Asn Tyr Asp Ser Pro Met Thr Val Asn Phe Gly Ile Asn Ser
450                 455                 460

Asp Lys Gln Tyr Thr Ser Gly Arg Val Trp Ser Phe Asp Arg Ser Ser
465                 470                 475                 480

Ala Asn Ile Thr Glu Lys Asp Ala Ile Asp Ala Ile Ser Gly Asn Lys
                485                 490                 495

Leu Thr Tyr Thr Ile Pro
            500

<210> SEQ ID NO 14
<211> LENGTH: 525
<212> TYPE: PRT
<213> ORGANISM: Artificial sequence
<220> FEATURE:
<223> OTHER INFORMATION: Synthetic construct

<400> SEQUENCE: 14

Pro Ala Val Thr Pro Asp Val Lys Ile Ser Ile Asp Thr Ser Arg Gly
1               5                   10                  15

Arg Thr Lys Ile Ser Pro Tyr Ile Tyr Gly Ala Asn Gln Asp Ile Gln
            20                  25                  30
```

-continued

Gly Val Val His Pro Ala Arg Arg Leu Gly Gly Asn Arg Leu Thr Gly
         35                  40                  45

Tyr Asn Trp Glu Asn Asn Met Ser Asn Ala Gly Ser Asp Trp Tyr His
 50                  55                  60

Ser Ser Asp Asp Tyr Met Cys Tyr Ile Met Gly Ile Thr Gly Asn Asp
 65                  70                  75                  80

Lys Asn Val Pro Ala Ala Val Val Ser Lys Phe His Glu Gln Ser Ile
                 85                  90                  95

Lys Gln Asn Ala Tyr Ser Ala Ile Thr Leu Gln Met Val Gly Tyr Val
            100                 105                 110

Ala Lys Asp Gly Asn Gly Thr Val Ser Glu Ser Glu Ala Pro Ser
        115                 120                 125

Pro Arg Trp Ala Glu Val Lys Phe Lys Lys Asp Gly Ala Leu Ser Leu
        130                 135                 140

Gln Pro Asp Val Asn Asp Asn Tyr Val Tyr Met Asp Glu Phe Ile Asn
145                 150                 155                 160

Tyr Leu Ile Asn Lys Tyr Gly Arg Ser Ser Ala Thr Gly Ile Lys
                165                 170                 175

Gly Tyr Ile Leu Asp Asn Glu Pro Asp Leu Trp Phe Thr Thr His Pro
                180                 185                 190

Arg Ile His Pro Gln Lys Val Thr Cys Ser Glu Leu Ile Asn Lys Ser
                195                 200                 205

Val Glu Leu Ala Lys Val Ile Lys Thr Leu Asp Pro Asp Ala Glu Ile
        210                 215                 220

Phe Gly Pro Ala Ser Tyr Gly Phe Val Gly Tyr Leu Thr Leu Gln Asp
225                 230                 235                 240

Ala Pro Asp Trp Asn Gln Val Lys Gly Asn His Arg Trp Phe Leu Ser
                245                 250                 255

Trp Tyr Leu Glu Gln Met Lys Lys Ala Ser Asp Ser Phe Gly Lys Arg
                260                 265                 270

Leu Leu Asp Val Leu Asp Ile His Trp Tyr Pro Glu Ala Gln Val Gly
        275                 280                 285

Gly Val Arg Ile Cys Phe Asp Gly Glu Asn Ser Thr Ser Arg Asp Val
        290                 295                 300

Ala Ile Ala Arg Met Gln Ala Pro Arg Thr Leu Trp Asp Pro Thr Tyr
305                 310                 315                 320

Lys Thr Thr Gln Lys Gly Gln Ile Thr Ala Gly Glu Asn Ser Trp Ile
                325                 330                 335

Asn Gln Trp Phe Pro Glu Tyr Leu Pro Leu Leu Pro Asn Ile Lys Ala
                340                 345                 350

Asp Ile Asp Lys Tyr Tyr Pro Gly Thr Lys Leu Ala Ile Thr Glu Phe
            355                 360                 365

Asp Tyr Gly Gly Lys Asp His Ile Ser Gly Gly Ile Ala Leu Ala Asp
        370                 375                 380

Val Leu Gly Ile Phe Gly Lys Tyr Gly Val Tyr Met Ala Ala Arg Trp
385                 390                 395                 400

Gly Asp Ser Gly Ser Tyr Ala Gln Ala Ala Tyr Asn Ile Tyr Leu Asn
                405                 410                 415

Tyr Asp Gly Lys Gly Ser Arg Tyr Gly Ser Thr Cys Val Ser Ala Glu
            420                 425                 430

Thr Thr Asp Val Glu Asn Met Pro Val Tyr Ala Ser Ile Glu Gly Glu
        435                 440                 445

Asp Asp Ser Thr Val His Ile Ile Leu Ile Asn Arg Asn Tyr Asp Arg
        450                 455                 460

```
Lys Leu Lys Ala Glu Ile Lys Met Asn Asn Thr Arg Val Tyr Thr Gly
465                 470                 475                 480

Gly Glu Ile Tyr Gly Phe Asp Ser Thr Ser Ser Gln Ile Arg Lys Met
                485                 490                 495

Gly Val Leu Ser Asn Ile Gln Asn Asn Thr Ile Thr Ile Glu Val Pro
                500                 505                 510

Asn Leu Thr Val Tyr His Ile Val Leu Thr Ser Ser Lys
            515                 520                 525

<210> SEQ ID NO 15
<211> LENGTH: 525
<212> TYPE: PRT
<213> ORGANISM: Artificial sequence
<220> FEATURE:
<223> OTHER INFORMATION: Synthetic construct

<400> SEQUENCE: 15

Pro Thr Ile Ser Pro Ser Pro Ser Val Val Glu Ile Thr Ile Asn Thr
1               5                   10                  15

Asn Ala Gly Arg Thr Gln Ile Ser Pro Tyr Ile Tyr Gly Ala Asn Gln
                20                  25                  30

Asp Ile Glu Gly Val Val His Ser Ala Arg Arg Leu Gly Gly Asn Arg
            35                  40                  45

Leu Thr Gly Tyr Asn Trp Glu Asn Asn Phe Ser Asn Ala Gly Asn Asp
50                  55                  60

Trp Tyr His Ser Asp Asp Tyr Leu Cys Trp Ser Met Gly Ile Ser
65                  70                  75                  80

Gly Glu Asp Ala Lys Val Pro Ala Ala Val Ser Lys Phe His Glu
                85                  90                  95

Tyr Ser Leu Lys Asn Asn Ala Tyr Ser Ala Val Thr Leu Gln Met Ala
                100                 105                 110

Gly Tyr Val Ser Lys Asp Asn Tyr Gly Thr Val Ser Glu Asn Glu Thr
            115                 120                 125

Ala Pro Ser Asn Arg Trp Ala Glu Val Lys Phe Lys Lys Asp Ala Pro
130                 135                 140

Leu Ser Leu Asn Pro Asp Leu Asn Asp Asn Phe Val Tyr Met Asp Glu
145                 150                 155                 160

Phe Ile Asn Tyr Leu Ile Asn Lys Tyr Gly Met Ala Ser Ser Pro Thr
                165                 170                 175

Gly Ile Lys Gly Tyr Ile Leu Asp Asn Glu Pro Asp Leu Trp Ala Ser
            180                 185                 190

Thr His Pro Arg Ile His Pro Asn Lys Val Thr Cys Lys Glu Leu Ile
        195                 200                 205

Glu Lys Ser Val Glu Leu Ala Lys Val Ile Lys Thr Leu Asp Pro Ser
210                 215                 220

Ala Glu Val Phe Gly Tyr Ala Ser Tyr Gly Phe Met Gly Tyr Tyr Ser
225                 230                 235                 240

Leu Gln Asp Ala Pro Asp Trp Asn Gln Val Lys Gly Glu His Arg Trp
                245                 250                 255

Phe Ile Ser Trp Tyr Leu Glu Gln Met Lys Lys Ala Ser Asp Ser Phe
            260                 265                 270

Gly Lys Arg Leu Leu Asp Val Leu Asp Leu His Trp Tyr Pro Glu Ala
        275                 280                 285

Arg Gly Gly Asn Ile Arg Val Cys Phe Asp Gly Glu Asn Asp Thr Ser
290                 295                 300
```

```
Lys Glu Val Val Ile Ala Arg Met Gln Ala Pro Arg Thr Leu Trp Asp
305                 310                 315                 320

Pro Thr Tyr Lys Thr Ser Val Lys Gly Gln Ile Thr Ala Gly Glu Asn
            325                 330                 335

Ser Trp Ile Asn Gln Trp Phe Ser Asp Tyr Leu Pro Ile Ile Pro Asn
        340                 345                 350

Val Lys Ala Asp Ile Glu Lys Tyr Tyr Pro Gly Thr Lys Leu Ala Ile
    355                 360                 365

Ser Glu Phe Asp Tyr Gly Gly Arg Asn His Ile Ser Gly Gly Ile Ala
370                 375                 380

Leu Ala Asp Val Leu Gly Ile Phe Gly Lys Tyr Gly Val Asn Phe Ala
385                 390                 395                 400

Ala Arg Trp Gly Asp Ser Gly Ser Tyr Ala Ala Ala Tyr Asn Ile
            405                 410                 415

Tyr Leu Asn Tyr Asp Gly Lys Gly Ser Lys Tyr Gly Asn Thr Asn Val
        420                 425                 430

Ser Ala Asn Thr Ser Asp Val Glu Asn Met Pro Val Tyr Ala Ser Ile
    435                 440                 445

Asn Gly Gln Asp Asp Ser Glu Leu His Ile Ile Leu Ile Asn Arg Asn
450                 455                 460

Tyr Asp Gln Lys Leu Gln Val Lys Ile Asn Ile Thr Ser Thr Lys
465                 470                 475                 480

Tyr Thr Lys Ala Glu Ile Tyr Gly Phe Asp Ser Asn Ser Pro Asp Ile
            485                 490                 495

Arg Lys Met Gly Asn Ile Asp Asn Ile Glu Ser Asn Val Phe Thr Leu
        500                 505                 510

Glu Val Pro Asn Leu Thr Val Tyr His Ile Val Leu Arg
            515                 520                 525

<210> SEQ ID NO 16
<211> LENGTH: 530
<212> TYPE: PRT
<213> ORGANISM: Artificial sequence
<220> FEATURE:
<223> OTHER INFORMATION: Synthetic construct

<400> SEQUENCE: 16

Pro Thr Ile Ser Pro Ser Pro Ser Val Val Glu Ile Thr Ile Asn Thr
1               5                   10                  15

Asn Ala Gly Arg Thr Gln Ile Ser Pro Tyr Ile Tyr Gly Ala Asn Gln
            20                  25                  30

Asp Ile Glu Gly Val Val His Ser Ala Arg Arg Leu Gly Gly Asn Arg
        35                  40                  45

Leu Thr Gly Tyr Asn Trp Glu Asn Asn Phe Ser Asn Ala Gly Asn Asp
    50                  55                  60

Trp Tyr His Ser Ser Asp Asp Tyr Leu Cys Trp Ser Met Gly Ile Ser
65                  70                  75                  80

Gly Glu Asp Ala Lys Val Pro Ala Ala Val Ser Lys Phe His Glu
                85                  90                  95

Tyr Ser Leu Lys Asn Asn Ala Tyr Ser Ala Val Thr Leu Gln Met Ala
            100                 105                 110

Gly Tyr Val Ser Lys Asp Asn Tyr Gly Thr Val Ser Glu Asn Glu Thr
        115                 120                 125

Ala Pro Ser Asn Arg Trp Ala Glu Val Lys Phe Lys Lys Asp Ala Pro
    130                 135                 140

Leu Ser Leu Asn Pro Asp Leu Asn Asp Asn Phe Val Tyr Met Asp Glu
```

```
            145                 150                 155                 160
Phe Ile Asn Tyr Leu Ile Asn Lys Tyr Gly Met Ala Ser Ser Pro Thr
                165                 170                 175
Gly Ile Lys Gly Tyr Ile Leu Asp Asn Glu Pro Asp Leu Trp Ala Ser
            180                 185                 190
Thr His Pro Arg Ile His Pro Asn Lys Val Thr Cys Lys Glu Leu Ile
        195                 200                 205
Glu Lys Ser Val Glu Leu Ala Lys Val Ile Lys Thr Leu Asp Pro Ser
    210                 215                 220
Ala Glu Val Phe Gly Tyr Ala Ser Tyr Gly Phe Met Gly Tyr Tyr Ser
225                 230                 235                 240
Leu Gln Asp Ala Pro Asp Trp Asn Gln Val Lys Gly Glu His Arg Trp
                245                 250                 255
Phe Ile Ser Trp Tyr Leu Glu Gln Met Lys Lys Ala Ser Asp Ser Phe
            260                 265                 270
Gly Lys Arg Leu Leu Asp Val Leu Asp Leu His Trp Tyr Pro Glu Ala
        275                 280                 285
Arg Gly Gly Asn Ile Arg Val Cys Phe Asp Gly Glu Asn Asp Thr Ser
    290                 295                 300
Lys Glu Val Val Ile Ala Arg Met Gln Ala Pro Arg Thr Leu Trp Asp
305                 310                 315                 320
Pro Thr Tyr Lys Thr Ser Val Lys Gly Gln Ile Thr Ala Gly Glu Asn
                325                 330                 335
Ser Trp Ile Asn Gln Trp Phe Ser Asp Tyr Leu Pro Ile Pro Asn
            340                 345                 350
Val Lys Ala Asp Ile Glu Lys Tyr Tyr Pro Gly Thr Lys Leu Ala Ile
        355                 360                 365
Ser Glu Phe Asp Tyr Gly Gly Arg Asn His Ile Ser Gly Gly Ile Ala
    370                 375                 380
Leu Ala Asp Val Leu Gly Ile Phe Gly Lys Tyr Gly Val Asn Phe Ala
385                 390                 395                 400
Ala Arg Trp Gly Asp Ser Gly Ser Tyr Ala Ala Ala Tyr Asn Ile
                405                 410                 415
Tyr Leu Asn Tyr Asp Gly Lys Gly Ser Lys Tyr Gly Asn Thr Asn Val
            420                 425                 430
Ser Ala Asn Thr Ser Asp Val Glu Asn Met Pro Val Tyr Ala Ser Ile
        435                 440                 445
Asn Gly Gln Asp Asp Ser Glu Leu His Ile Ile Leu Ile Asn Arg Asn
    450                 455                 460
Tyr Asp Gln Lys Leu Gln Val Lys Ile Asn Ile Thr Ser Thr Pro Lys
465                 470                 475                 480
Tyr Thr Lys Ala Glu Ile Tyr Gly Phe Asp Ser Asn Ser Pro Glu Tyr
                485                 490                 495
Lys Lys Met Gly Asn Ile Asp Asn Ile Glu Ser Asn Val Phe Thr Leu
            500                 505                 510
Glu Val Pro Lys Phe Asn Gly Val Ser His Ser Ile Thr Leu Asp Phe
        515                 520                 525
Asn Val
    530

<210> SEQ ID NO 17
<211> LENGTH: 506
<212> TYPE: PRT
<213> ORGANISM: Artificial sequence
<220> FEATURE:
```

<223> OTHER INFORMATION: Synthetic construct

<400> SEQUENCE: 17

```
Lys Val Asn Ala Ala Gly Gly Phe Asp Met Asn Ile Lys Val Asp Leu
1               5                   10                  15

Lys Gly Glu Arg Lys Glu Ile Ser Pro Leu Ile Tyr Gly Val Asn Gln
            20                  25                  30

Tyr Thr Thr Asp Leu Lys Ser Val Lys Thr Thr Ala Val Arg Gln Gly
        35                  40                  45

Gly Asn Arg Met Thr Ala Tyr Asn Trp Glu Asn Asn Ala Ser Asn Ala
50                  55                  60

Gly Ser Asp Trp Lys His Ser Ser Asp Asn Asn Leu Ser Asp Ser Asn
65                  70                  75                  80

Pro Pro Ala Glu Val Val Gln Arg Leu Ser Lys Glu Ala Ala Lys Tyr
                85                  90                  95

Gly Val Asp Tyr Lys Met Thr Thr Leu Gln Met Ala Gly Tyr Val Ser
            100                 105                 110

Ala Asp Lys Asp Gly Thr Val Lys Glu Asp Glu Val Ala Pro Ser Lys
        115                 120                 125

Arg Trp Asn Glu Val Lys Phe Thr Lys Gly Ala Pro Phe Ala Asp Glu
130                 135                 140

Pro Asp Leu Thr Asp Gly Val Val Tyr Met Asp Glu Tyr Val Asn Tyr
145                 150                 155                 160

Ile Ile Asn Lys Leu Gly Asp Ser Gln Ser Pro Thr Gly Ile Gln Gly
                165                 170                 175

Tyr Ser Leu Asp Asn Glu Pro Val Leu Trp Asn Asp Thr His Pro Arg
            180                 185                 190

Val His Pro Glu Pro Val Thr Ile Glu Glu Leu Gly Asn Lys Ser Ile
        195                 200                 205

Glu Leu Ala Lys Ala Val Lys Lys Leu Asp Pro Lys Ala Glu Ile Phe
210                 215                 220

Gly Pro Ala Leu Tyr Gly Tyr Thr Ala Phe Asp His Leu Asp Asp Asp
225                 230                 235                 240

Glu Gln His Thr Glu Ser Gly Asp Val Lys Ser Lys Asn Asn Tyr His
                245                 250                 255

Trp Tyr Leu Asp Cys Tyr Leu Asp Gln Met Lys Lys Ala Ser Glu Glu
            260                 265                 270

Glu Gly Thr Arg Leu Leu Asp Val Leu Asp Ile His Tyr Tyr Ser Glu
        275                 280                 285

Ser Ala Arg Thr Gly Ala Glu Asp Arg Val Gln Ser Val Arg Thr Leu
290                 295                 300

Tyr Glu Glu Gly Phe Ser Glu Asn Ser Trp Ile Gly Gln Trp Cys Met
305                 310                 315                 320

Gln Asn Val Pro Ile Leu Pro Thr Ile Lys Lys Ser Ile Asp Thr Tyr
                325                 330                 335

Tyr Pro Gly Thr Lys Leu Ala Ile Ser Glu Tyr Asn Phe Lys Gly Gly
            340                 345                 350

Glu Asp Thr Ser Gly Thr Ile Ala Gln Ala Glu Ala Leu Gly Cys Phe
        355                 360                 365

Ala Asp Gln Gly Val Tyr Leu Ala Thr Leu Trp Gly Gly Glu Pro Phe
370                 375                 380

Ile Ile Ser Gly Ile Asn Leu Tyr Thr Asn Tyr Asp Gly Lys Gly Gly
385                 390                 395                 400

Cys Phe Gly Asp Thr Leu Ile Pro Ala Ser Thr Glu Asp Val Ser Lys
```

```
              405                 410                 415
Ser Ser Thr Tyr Ala Ala Val Asn Asp Gly Asp Glu Ser Lys Val Thr
                420                 425                 430

Val Met Ile Thr Asn Lys Asn Met Thr Glu Ala Glu Asn Ala Val Ile
                435                 440                 445

Asp Leu Glu Asn Ala Ser Lys Asp Tyr Lys Ser Ala Ala Val Tyr Ala
            450                 455                 460

Val Tyr Gly Asp Asn Asp Gln Val Arg Leu Leu Asp Ile Val Lys Asp
465                 470                 475                 480

Val Lys Asp Asn Lys Val Asn Val Glu Leu Pro Ala Phe Ser Ala Ala
                485                 490                 495

Met Val Val Ser Asp Asp Ala Ala Ala
                500             505

<210> SEQ ID NO 18
<211> LENGTH: 506
<212> TYPE: PRT
<213> ORGANISM: Artificial sequence
<220> FEATURE:
<223> OTHER INFORMATION: Synthetic construct

<400> SEQUENCE: 18

Thr Val Asn Ala Ala Gly Gly Tyr Asp Met Asn Val Thr Val Asp Leu
1               5                   10                  15

Lys Gly Glu Lys Lys Ala Ile Ser Pro Leu Ile Tyr Gly Val Asn Gln
                20                  25                  30

Tyr Thr Thr Asp Leu Arg Asp Val Lys Thr Thr Ala Val Arg Gln Gly
            35                  40                  45

Gly Asn Arg Met Thr Ala Tyr Asn Trp Glu Thr Asn Ala Ser Asn Ala
    50                  55                  60

Gly Ser Asp Trp Lys His Ser Ser Asp Asn Asn Leu Ser Asp Ser Asp
65                  70                  75                  80

Asp Pro Ala Asp Cys Val Gln Val Leu Ser Lys Gln Ala Ala Lys Tyr
                85                  90                  95

Asn Val Asn Tyr Lys Leu Thr Thr Leu Gln Leu Ala Gly Tyr Val Ser
                100                 105                 110

Ala Asp Lys Asn Gly Pro Val Ser Glu Ala Glu Lys Ala Pro Ser Asp
            115                 120                 125

Arg Trp Asn Lys Val Val Leu Thr Lys Asn Ala Pro Phe Ala Asp Thr
        130                 135                 140

Pro Asp Leu Thr Asp Gly Val Val Tyr Met Asp Glu Tyr Val Asn Tyr
145                 150                 155                 160

Ile Ile Asn Lys Leu Gly Asp Ser Gln Ser Ala Glu Gly Ile Gln Gly
                165                 170                 175

Tyr Ser Leu Asp Asn Glu Pro Val Leu Trp Asn Asp Thr His Ser Arg
            180                 185                 190

Met His Pro Asp Pro Val Thr Ile Glu Glu Leu Gly Ser Lys Ser Val
        195                 200                 205

Glu Met Ala Lys Ala Val Lys Lys Leu Asp Pro Lys Ala Glu Val Phe
    210                 215                 220

Gly Pro Ala Leu Tyr Gly Tyr Thr Ala Phe Asp His Leu Asp Asp Asp
225                 230                 235                 240

Asp Ala His Thr Glu Trp Glu Glu Ile Lys Lys Ala Asn Asn Tyr His
                245                 250                 255

Trp Tyr Leu Asp Cys Tyr Leu Asp His Met His Lys Ala Ser Glu Glu
            260                 265                 270
```

```
Asn Gly Ala Arg Leu Leu Asp Val Leu Asp Ile His Tyr Tyr Ser Glu
            275                 280                 285

Ser Ala Arg Lys Gly Ile Glu Asp Arg Leu Gln Ser Val Arg Thr Leu
            290                 295                 300

Tyr Glu Pro Gly Phe Ser Glu Asn Ser Trp Ile Gly Gln Trp Cys Met
305                 310                 315                 320

Glu Asn Val Pro Ile Leu Pro Thr Ile Gln Lys Ser Ile Asp Thr Tyr
                325                 330                 335

Tyr Pro Gly Thr Lys Leu Gly Ile Ser Glu Tyr Asn Phe Gly Gly Gly
            340                 345                 350

Asp Asp Ala Ser Gly Thr Ile Ala Gln Ala Glu Ala Leu Gly Cys Tyr
            355                 360                 365

Ala Asp Gln Gly Val Tyr Phe Ala Ser Leu Trp Gly Gly Glu Pro Phe
            370                 375                 380

Ile Leu Ser Gly Ile Gln Leu Tyr Thr Asn Tyr Asp Gly Lys Gly Gly
385                 390                 395                 400

Cys Phe Gly Asp Thr Leu Ile Pro Ala Ser Thr Gly Asp Val Ser Lys
                405                 410                 415

Ser Ser Thr Tyr Ala Ala Val Asn Ala Lys Asp Asp Ser Lys Val Thr
            420                 425                 430

Val Met Val Thr Asn Lys Asp Leu Lys Glu Asn Glu Asn Ala Val Ile
            435                 440                 445

Asp Leu Arg Asn Ala Asp Lys Ser Tyr Lys Ser Ala Ala Val Tyr Ala
            450                 455                 460

Val Phe Gly Asp Ser Glu Glu Ile Arg Leu Ile Asp Ile Ile Lys Asp
465                 470                 475                 480

Val Lys Asp Asn Lys Val Lys Thr Glu Leu Pro Ala Phe Ser Ala Ala
                485                 490                 495

Met Val Val Val Ser Asp Gln Ala Asp Ala
            500                 505

<210> SEQ ID NO 19
<211> LENGTH: 523
<212> TYPE: PRT
<213> ORGANISM: Artificial sequence
<220> FEATURE:
<223> OTHER INFORMATION: Synthetic construct

<400> SEQUENCE: 19

Ala Gln Asn Pro Ser Val Thr Ile Ser Val Asn Ala Asn Ala Gly Arg
1               5                   10                  15

His Pro Ile Asn Pro Ala Val Tyr Gly Leu Ala Tyr Ala Thr Thr Ala
            20                  25                  30

Thr Leu Ala Asp Leu Asn Val Pro Leu His Arg Tyr Gly Gly Asn Asn
        35                  40                  45

Thr Ser Arg Tyr Asn Trp Gln Leu Asn Ala Asp Asn Arg Gly Ala Asp
        50                  55                  60

Trp Tyr Phe Glu Ser Ile Gly Glu Ala Ser Ser Val Ala Gly Glu Arg
65                  70                  75                  80

Gly Asp Thr Phe Ile Ala Asn Ser Gln Ala Ala Gly Ala Gln Ala Met
            85                  90                  95

Ile Thr Ile Pro Thr Ile Gly Trp Val Ala Arg Leu Gly Ala Asn Arg
            100                 105                 110

Ser Lys Leu Ala Ser Phe Ser Ile Ala Lys Tyr Gly Ala Gln Ser Gly
        115                 120                 125
```

```
Asn Asp Trp Gln Trp Phe Pro Asp Ala Gly Asn Gly Val Leu Thr Ser
    130             135                 140

Gly Gln Asn Val Thr Gly Asn Asn Pro Asn Asp Ala Asn Thr Leu Val
145                 150                 155                 160

Asp Ser Thr Phe Gln Gln Gly Trp Ala Gln His Leu Val Ser Gln Trp
            165                 170                 175

Gly Thr Ala Ala Gly Gly Leu Arg Tyr Tyr Ile Leu Asp Asn Glu
            180                 185                 190

Pro Ser Ile Trp Phe Ser Thr His Arg Asp Val His Pro Val Gly Pro
        195                 200                 205

Thr Met Asp Glu Ile Arg Asp Lys Met Leu Asp Tyr Gly Ala Lys Ile
210                 215                 220

Lys Thr Val Asp Pro Ser Ala Leu Ile Val Gly Pro Glu Glu Trp Gly
225                 230                 235                 240

Trp Ser Gly Tyr Thr Leu Ser Gly Tyr Asp Gln Gln Tyr Gly Gly Leu
                245                 250                 255

His Gly Trp Ser Phe Met Pro Asp Arg Asn Asn His Gly Gly Trp Asp
            260                 265                 270

Tyr Leu Pro Trp Leu Leu Asp Gln Leu Arg Gln Asn Asn Leu Ser Thr
        275                 280                 285

Gly Arg Arg Leu Leu Asp Val Phe Ser Val His Tyr Tyr Pro Gln Gly
290                 295                 300

Gly Glu Phe Gly Asn Asp Thr Ser Ser Ala Met Gln Leu Arg Arg Asn
305                 310                 315                 320

Arg Ser Thr Arg Ser Leu Trp Asp Pro Asn Tyr Ile Asp Glu Thr Trp
                325                 330                 335

Ile Asn Asp Lys Val Gln Leu Ile Pro Arg Leu Lys Asn Trp Val Ser
            340                 345                 350

Thr Tyr Tyr Pro Gly Thr Leu Thr Ala Ile Thr Glu Tyr Asn Trp Gly
            355                 360                 365

Ala Glu Ser His Ile Asn Gly Ala Thr Thr Gln Ala Asp Ile Leu Gly
        370                 375                 380

Ile Phe Gly Arg Glu Gly Leu Asp Met Ala Ala Arg Trp Thr Thr Pro
385                 390                 395                 400

Asp Thr Ala Thr Pro Thr Tyr Lys Ala Ile Lys Met Tyr Arg Asn Tyr
            405                 410                 415

Asp Gly Asn Lys Ser Ala Phe Gly Asp Thr Ser Val Thr Ala Thr Ala
            420                 425                 430

Pro Asn Pro Asp Asn Val Ser Ala Phe Ala Ala Val Arg Ser Ser Asp
        435                 440                 445

Gly Ala Leu Thr Val Met Val Ile Asn Lys Tyr Leu Ser Gly Asn Thr
450                 455                 460

Pro Ala Thr Ile Asn Leu Ser Asn Phe Thr Gln Ala Gln Ala Gln
465                 470                 475                 480

Val Trp Gln Leu Thr Ala Ala Asn Thr Ile Asn His Leu Ser Asn Val
            485                 490                 495

Ser Leu Ser Gly Ser Ser Leu Ser Leu Thr Leu Pro Ala Gln Ser Val
            500                 505                 510

Thr Leu Leu Val Ile Pro Ala Ser Thr Ala Ala
            515                 520
```

<210> SEQ ID NO 20
<211> LENGTH: 573
<212> TYPE: PRT
<213> ORGANISM: Artificial sequence
<220> FEATURE:
<223> OTHER INFORMATION: Synthetic construct

<400> SEQUENCE: 20

```
Val Val His Gly Ala Thr Ala Lys Asp Val Thr Ile Lys Ile Asp Thr
1               5                   10                  15

Ser Ala Glu Arg Lys Pro Ile Ser Pro Tyr Ile Tyr Gly Thr Asn Gln
            20                  25                  30

Tyr Thr Thr Asp Leu Ala Gly Asp Val Asn Val Thr Ala Arg Arg Leu
        35                  40                  45

Gly Gly Asn Arg Met Thr Gly Tyr Asn Trp Glu Asn Asn Met Ser Asn
    50                  55                  60

Ala Gly Ser Asp Trp Tyr His Ser Ser Asp Asn Tyr Leu Cys Trp Asn
65                  70                  75                  80

Gly Val Thr Lys Glu Glu Cys Ser Lys Pro Ala Ala Val Val Thr
                85                  90                  95

Ser Phe His Asp Gln Ser Leu Lys Asn Gly Ala Pro Tyr Ser Leu Val
                100                 105                 110

Thr Leu Gln Met Ala Gly Tyr Val Ser Lys Asp Gly Asn Gly Arg Ser
            115                 120                 125

Lys Leu Ala Ser Phe Thr Val Ser Glu Ser Glu Thr Ala Pro Ser Ala
130                 135                 140

Arg Trp Asn Glu Val Lys Phe Ala Lys Asn Ala Pro Phe Ser Leu Gln
145                 150                 155                 160

Pro Asp Leu Asn Asp Asn Asn Pro Asn Asp Ala Asn Thr Leu Val Asp
                165                 170                 175

Tyr Val Tyr Met Asp Glu Phe Val Asn Tyr Leu Val Asn Lys Tyr Gly
            180                 185                 190

Thr Ala Ser Thr Pro Thr Gly Ile Lys Gly Tyr Ser Leu Asp Asn Glu
        195                 200                 205

Pro Ala Leu Trp Ser His Thr His Pro Arg Ile His Pro Glu Lys Val
    210                 215                 220

Thr Ala Lys Glu Leu Ile Asp Lys Ser Val Glu Leu Ser Lys Ala Val
225                 230                 235                 240

Lys Lys Val Asp Pro Ser Ala Glu Ile Phe Gly Pro Ala Leu Tyr Gly
                245                 250                 255

Phe Gly Ala Tyr Thr Leu Ser Gly Tyr Asp Leu Gln Asp Ala Gly Gln
            260                 265                 270

His Pro Asp Trp Asn Ser Val Lys Ser Lys Gly Asn Tyr Gly Ser Trp
        275                 280                 285

Asp Phe Ile Asp Tyr Tyr Leu Asp Gln Met Lys Lys Ala Ser Asp Glu
    290                 295                 300

Glu Gly Lys Arg Leu Leu Asp Val Leu Asp Val His Trp Tyr Pro Glu
305                 310                 315                 320

Ala Arg Gly Gly Gly Ile Arg Ile Cys Phe Asp Gly Glu Asn Val Thr
                325                 330                 335

Asn Ile Glu Thr Asn Lys Ala Arg Met Gln Ala Pro Arg Thr Leu Trp
            340                 345                 350

Asp Pro Thr Tyr Lys Thr Ser Val Lys Gly Gln Ile Thr Ala Gly Glu
        355                 360                 365

Asp Ser Trp Ile Gly Gln Trp Asn Ser Glu Phe Leu Pro Ile Leu Pro
    370                 375                 380

Arg Leu Lys Gln Ser Ile Asp Lys Tyr Tyr Pro Gly Thr Lys Leu Ala
385                 390                 395                 400
```

```
Ile Thr Glu Tyr Ser Tyr Gly Gly Glu Asn His Ile Ser Gly Gly Ile
                405                 410                 415

Ala Gln Ala Asp Val Leu Gly Ile Phe Gly Lys Tyr Gly Val Tyr Met
            420                 425                 430

Ala Thr Tyr Trp Lys Leu Lys Asp Gly Ser Asn Asn Tyr Val Ser Ala
        435                 440                 445

Ala Tyr Asn Leu Tyr Arg Asn Tyr Asp Gly Lys Gly Ser Lys Phe Gly
    450                 455                 460

Asp Thr Ser Val Ser Ala Gln Thr Ser Asp Ile Glu Asn Ser Ser Val
465                 470                 475                 480

Tyr Ala Ser Val Thr Gly Glu Asp Ser Glu Leu His Ile Ile Val
                485                 490                 495

Met Asn Lys Asn Tyr Asp Ser Ala Phe Asn Ala Gln Phe Asp Leu Arg
            500                 505                 510

Ser Ser Thr Lys Thr Tyr Thr Ser Gly Lys Val Trp Gly Phe Asp Ser
        515                 520                 525

Asn Ser Ser Gln Ile Thr Glu Arg Ala Pro Ile Thr Asn Ile Ser Gly
    530                 535                 540

Asn Arg Phe Thr Tyr Thr Val Pro Ala Leu Thr Ala Tyr His Ile Val
545                 550                 555                 560

Leu Thr Ala Asp Asn Asp Thr Ser Pro Val Pro Pro Val
                565                 570

<210> SEQ ID NO 21
<211> LENGTH: 458
<212> TYPE: PRT
<213> ORGANISM: Artificial sequence
<220> FEATURE:
<223> OTHER INFORMATION: Synthetic construct

<400> SEQUENCE: 21

Pro Thr Pro Ala Gln Ser Thr Ser Val Ile Asn Val Thr Val Asn Leu
1               5                   10                  15

Asn Lys Gly Lys Thr Ala Asn Leu Val Ala Ala Tyr Ala Glu Ile Ser
            20                  25                  30

Ala Gly Glu Lys Leu Ser Ser Lys Phe Asn Thr Ser Ala Gln Thr Phe
        35                  40                  45

Asp Ser Arg Asn Gln Gln Tyr Asp Asn Met Leu Thr Ser Met Lys Leu
    50                  55                  60

Pro Gly Ala Asp Trp Glu Val Ala Gly Ser Arg Thr Ser Thr Leu Ser
65              70                  75                  80

Glu Lys Ala Ala Ala Leu Asn Val Asn Gln Thr Ala Ile Ile Pro Ala
            85                  90                  95

Val Trp Ala Ala Leu Lys Tyr Asn Ser Leu Gln Gln Asn Gly Lys Gln
        100                 105                 110

Ser Gly Ser Lys Lys Gln Phe Val Asn Lys Gly Asp Gly Val Leu Gln
    115                 120                 125

Asp Thr Gln Asn Thr Thr Gly Gly Gln Thr Phe Val Gln Gly Tyr Ile
130                 135                 140

His Phe Ile Ile Lys Arg Leu Asn Ser Gln Ser Lys Ala Val Gln Tyr
145                 150                 155                 160

Ile Ile Asp Ile Asn Ser Ser Leu Val Gly Asp Asn Thr Gly Cys Ser
                165                 170                 175

Val Val Glu Arg Asn Ile Ser Tyr Ala Gln Val Ile Thr Leu Ala Gly
            180                 185                 190

Leu Val Val Tyr Val Ser Trp Tyr Ala Gly Phe Lys Thr Phe Asp Thr
```

```
                195                 200                 205
Asp Glu Leu Thr Gly Ser Gly Gln Leu Pro Lys Gly Asn Gly His Arg
210                 215                 220

Tyr Leu Ser Trp Leu Glu Lys Leu Arg Leu Ser Asn Gln Ser Phe Thr
225                 230                 235                 240

Ile Ala Phe Ser Leu Tyr Ser Gln Ser Met Arg Thr Asn Gln Val Thr
                245                 250                 255

Asn Ala Glu Pro Gly Ser Asp Asp Val Lys Ile Asp Leu Arg Ser Val
                260                 265                 270

Ser Tyr Glu Ser Gly Phe Ile Thr Gln Asp Asn Thr Ala Thr Phe Lys
                275                 280                 285

Asp Tyr Val Gln Leu Ile Asn Val Gln Ala Asp Val Glu Thr Asn Leu
                290                 295                 300

Thr Ser Met Ser Phe Asp Phe Lys Ala Gly Asp Thr Thr Thr Thr
305                 310                 315                 320

Thr Met Thr Glu Ala Val Leu Ala Asp Asn Asp Leu Asn Leu Asn Arg
                325                 330                 335

Glu Thr Thr Gly Asp Gly Gly Ser Phe Thr Ala Ser Gly Ile Lys Ile
                340                 345                 350

Thr Asn Asn Gly Thr Tyr Ser Ile Asn Ile Lys Cys Glu Ala Thr Asn
                355                 360                 365

Val Val Val Met Pro Thr His Ala Ile Asn Asp Ala Ser Tyr Lys Lys
                370                 375                 380

Val Thr Leu Val Leu Ile Arg Ser Met Thr Gln Pro Thr Asp Val Asn
385                 390                 395                 400

Ile Asn Ile Glu Asn Gly Ser Thr Asn Gln Ser Lys Ala Glu Ile Tyr
                405                 410                 415

Ala Val Tyr Lys Thr Asn Pro Asn Tyr Lys Lys Met Asp Asn Val Ser
                420                 425                 430

Gln Val Lys Asp Ser Lys Val Ser Leu Glu Leu Pro Phe Ser Val Cys
                435                 440                 445

Met Val Ser Val Ser Thr Ser Ala Pro Val
    450                 455

<210> SEQ ID NO 22
<211> LENGTH: 339
<212> TYPE: PRT
<213> ORGANISM: Artificial sequence
<220> FEATURE:
<223> OTHER INFORMATION: Synthetic construct

<400> SEQUENCE: 22

Thr Ser Asn Thr Pro Pro Pro Thr Met Glu Phe Ser Ala Lys Gly
1               5                   10                  15

Asp Ala Gln Asn Val Trp Ala Phe Glu Asn Ala Val His Ala Leu Val
                20                  25                  30

Gln Leu Arg Leu Ala Thr Leu Asn Glu Thr Phe Trp Ser Asp Tyr Asp
                35                  40                  45

Ile Ser Gln Ser Lys Ser Asn Thr Glu Cys Tyr Gln Lys Ile Lys Tyr
            50                  55                  60

Asn Gln Ser Tyr Thr Asp Lys Met Thr Thr Ile Arg Asn Ser Pro Ile
65                  70                  75                  80

Ala Asn Glu Asp Val Asn Asp Ala Lys Glu Leu Thr Gly Thr Ala Ala
                85                  90                  95

Ser Asn His Val Glu Asp Val Ala Trp Ala Gln Leu Ser Gln Trp Ser
                100                 105                 110
```

```
Ala Gly Ala Lys Leu Arg Ala Ala Val Phe Asp Arg Asp Met Asn Pro
            115                 120                 125

Pro Gln Ile Glu Ile Gly Asn Met Thr Asp Met Gly Ala Thr Ala Ala
130                 135                 140

Ile Tyr Thr Leu Glu Glu Phe Trp Thr Asn Ser Gln Asn Ser Ser Asp
145                 150                 155                 160

Ala His Glu Ser Thr Glu Asp Arg Glu His Val Pro Cys Ser His
                165                 170                 175

Gln Asn His Thr Ala Asn Arg Ile Gly Gln Val Lys Glu Val Thr Ser
                180                 185                 190

Asp Asp Arg Lys Leu Cys Val Glu Arg Val Thr Glu Asn Ser Glu Asn
            195                 200                 205

Cys Met Trp Asn Lys Ile Leu Ser Trp Ser Gly Leu Ser Asn Trp Arg
210                 215                 220

Ser Ala Asn Ala Leu Ile Cys Tyr Arg Gln Asp Phe Ala Leu Gln Gly
225                 230                 235                 240

Ser Ala Val Glu Pro Pro Ala Gln Pro Val Gln Met Leu Lys Ala Cys
                245                 250                 255

Asn Leu Pro Ser Pro Thr Ser Lys Val Ala Phe Val Ser Gln Glu Gly
                260                 265                 270

Asn Thr Met Asp Val Met Ile Leu Tyr Leu Ser Glu Lys Leu Thr Phe
            275                 280                 285

Val Ser Val Thr Asn Asp Arg Lys Lys Ile Arg Ser Leu Thr Arg Gly
            290                 295                 300

Gly Thr Glu Val Arg Gln Ala Gly Ile Leu Asp Asp Leu Glu Ser Thr
305                 310                 315                 320

Leu Asn Val Lys Ile Asn Gln Asn Gly Val Ser Leu Ile Glu Ser Gly
                325                 330                 335

Glu Ala Ala

<210> SEQ ID NO 23
<211> LENGTH: 214
<212> TYPE: PRT
<213> ORGANISM: Artificial sequence
<220> FEATURE:
<223> OTHER INFORMATION: Synthetic construct

<400> SEQUENCE: 23

Lys Ile Ser Glu Gly Gly Tyr Ser Asp Arg Thr Ser Gln Lys Ala Ser
1               5                   10                  15

Thr Arg Thr Leu Thr Thr Pro His Tyr Ser Tyr Arg Lys Phe Ser Glu
                20                  25                  30

Leu Asn Ile Glu Gly Ala Ala Lys Glu Val Ile Asp Ala Ala Asn Ile
            35                  40                  45

Glu Gln Glu Ala Ile Leu Gly Gln Asp Lys Lys Asp Gln Pro Gln Trp
        50                  55                  60

Pro Asp Glu Thr Gly Lys Ser Gln Leu His Met Ser Glu Ser Ala Thr
65                  70                  75                  80

Val Gln Leu Lys Met Ala Arg Ser Asp Leu Ala Lys Asn Lys Ala Ser
                85                  90                  95

Leu His Tyr Gly Asp Asp Met Gln Thr Asn Asn Glu Val Ala Ala Lys
            100                 105                 110

Glu Phe Val Gly Thr Ser Val Ala Met Gln Leu Asn Ala Ala Thr Lys
        115                 120                 125

Pro Ser Gly Thr Lys Gln Phe Asp Glu Thr Glu Ala Ser Phe Cys Asn
```

```
               130                 135                 140
Pro Ala Thr Thr Ile Glu Lys Phe Asn Ser Arg Lys Thr Asn Gly Pro
145                 150                 155                 160

Asn Arg Asn Lys Asn Ala Thr Asp Phe Lys Asp Asn Ile Gln Thr Gln
            165                 170                 175

Met Asp Ala Glu Pro Val Ile Gln Gln Gln Phe Gly Asp Glu Asp Asn
            180                 185                 190

Leu Leu Thr Ala Val Ser Gln Asn Val Ile Lys Thr Lys Ala Leu His
        195                 200                 205

Arg Asp Ala Thr Tyr Ser
    210
```

VARIANTS OF A FAMILY 44 XYLOGLUCANASE

CROSS-REFERENCE TO RELATED APPLICATIONS

This application is a 35 U.S.C. 371 national application of PCT/EP2009/056875 filed Jun. 4, 2009, which claims priority or the benefit under 35 U.S.C. 119 of European application no. EP 08157769.4 filed Jun. 6, 2008 and U.S. provisional application No. 61/059,832 filed Jun. 9, 2008, the contents of which are fully incorporated herein by reference.

REFERENCE TO A SEQUENCE LISTING

This application contains a Sequence Listing in computer readable form. The computer readable form is incorporated herein by reference.

FIELD OF THE INVENTION

The present invention relates to variants of a xyloglucanase belonging to family 44 of glycosyl hydrolases, polynucleotides encoding the variants and methods of producing the variants.

BACKGROUND OF THE INVENTION

Xyloglucan is a major structural polysaccharide in the primary (growing) cell wall of plants. Structurally, xyloglucans consists of a cellulose-like beta-1,4-linked glucose backbone which is frequently substituted with various side chains. Xyloglucan is believed to function in the primary wall of plants by cross-linking cellulose micro fibrils, forming a cellulose-xyloglucan network.

Xyloglucanses are capable of catalyzing the solubilization of xyloglucan to xyloglucan oligosaccharides. Some xyloglucanases only exhibit xyloglucanase activity, whereas others exhibit both xyloglucanase and cellulase activity. Xyloglucanses may be classified in EC 3.2.1.4 or EC. 3.2.1.151. Enzymes with xyloglucanase activity are for example described in Vincken et al. (1997) *Carbohydrate Research* 298(4):299-310, wherein three different endoglucanases EndoI, EndoV and EndoVI from *Trichoderma viride* (similar to *T. reesei*) are characterized. EndoI, EndoV and EndoVI belongs to family 5, 7 and 12 of glycosyl hydrolases, respectively, see Henrissat, B. (1991) Biochem. J. 280: 309-316, and Henrissat, B. and Bairoch, A. (1993) Biochem. J. 293: 781-788. WO 94/14953 discloses a family 12 xyloglucanase (EG II) cloned from the fungus *Aspergillus aculeatus*. WO 99/02663 discloses family 12 and family 5 xyloglucanases cloned from *Bacillus licheniformis* and *Bacillus agaradhaerens*, respectively. WO 01/062903 discloses family 44 xyloglucanases.

In particular WO 99/02663 and WO 01/062903 suggest that xyloglucanases may be used in detergents.

It is an object of the present invention to provide variants of xyloglucanases belonging to family 44 of glycosyl hydrolases with improved properties compared to its parent enzyme.

SUMMARY OF THE INVENTION

The present invention relates to isolated variants of a parent xyloglucanase, comprising an alteration at one or more (several) positions selected from the group consisting of position number 68, 123, 156, 118, 200, 129, 137, 193, 92, 83, 149, 34, 340, 332, 9, 76, 331, 310, 324, 498, 395, 366, 1, 374, 7, 140, 8, 14, 21, 211, 37, 45, 13, 78, 87, 436, 101, 104, 111, 306, 117, 119, 414, 139, 268, 142, 159, 164, 102, 168, 176, 180, 482, 183, 202, 206, 217, 4, 222, 19, 224, 228, 232, 2, 240, 244, 5, 247, 249, 328, 252, 259, 406, 267, 269, 275, 179, 166, 278, 281, 288, 298, 301, 18, 302, 165, 80, 303, 316, 169, 322, 120, 146, 342, 348, 147, 353, 380, 468, 382, 383, 38, 384, 389, 391, 10, 392, 396, 177, 397, 399, 409, 237, 413, 253, 415, 418, 40, 443, 445, 148, 449, 225, 450, 454, 3, 455, 456, 299, 461, 470, 204, 476, 488, 347, and 507, which position corresponds to a position in amino acid sequence SEQ ID NO:3 and wherein the alteration(s) are independently i) an insertion of an amino acid downstream of the amino acid which occupies the position,
ii) deletion of the amino acid which occupies the position, or
iii) a substitution of the amino acid which occupies the position with a different amino acid; and
the parent xyloglucanase is a family 44 xyloglucanase; and the variant has xyloglucanase activity.

The present invention also relates to isolated polynucleotides encoding the variant xyloglucanases or polypeptides having xyloglucanases activity, nucleic acid constructs, vectors, and host cells comprising the polynucleotides, and methods of producing a variant of a parent xyloglucanase or a polypeptide having xyloglucanases activity.

DETAILED DESCRIPTION OF THE INVENTION

The present invention relates to variants of parent family 44 xyloglucanases, comprising an alteration, preferably in the form of a substitution and/or an insertion and/or a deletion at one or more (several) positions, where the numbering of the positions corresponds to the numbering of the positions of SEQ ID NO:3. The variants of the present invention have xyloglucanase activity and potentially also cellulolytic activity. The variants of the present invention have improved properties compared to the parental xyloglucanase. In one aspect, the variants have improved stability in liquid detergents, especially liquid laundry detergent compositions.

DEFINITIONS

Figure 1:
FIG. 1 shows consensus sequences performed by aligning SEQ ID NO: 3, with SEQ ID NO: 5 and SEQ ID NO: 7 as well as with other sequences (SEQ ID NO: 8 to SEQ ID NO: 19) from the uniprot database which are 30% identical to the family 44 glycosyl hydrolase region of SEQ ID NO: 3. SEQ ID NO: 20 to SEQ ID NO: 23 represent consensus sequences as described herein.

Xyloglucanase Activity:
The term "xyloglucanase activity" is defined herein as an enzyme catalyzed hydrolysis of xyloglucan. The reaction involves endo hydrolysis of 1,4-beta-D-glucosidic linkages in xyloglucan. For purposes of the present invention, xyloglucanase activity is determined using AZCL-xyloglucan (from Megazyme) as the reaction substrate. The assay can be performed in several ways, e.g. as described in Example 2 of the present application or as described in WO 01/62903. One unit of xyloglucanase activity (XyloU) is defined by reference to the assay method described in WO 01/62903, page 60, lines 3-17.

Cellulase Activity:
The term "cellulase activity" is defined herein as an enzyme catalyzed hydrolysis of 1,4-beta-D-glucosidic linkages in beta-1,4-glucan (cellulose). For purposes of the present invention, cellulase activity is determined using AZCL-HE-cellulose (from Megazyme) as the reaction substrate.

Variant:

The term "variant" is defined herein as a polypeptide having xyloglucanase activity comprising an alteration, such as a substitution, insertion, and/or deletion, of one or more (several) amino acid residues at one or more (several) specific positions which positions correspond to the amino acid positions in SEQ ID NO: 3. The variants of the invention may also have cellulase activity. The altered polypeptide (variant) is obtained through human intervention by modification of the polynucleotide sequence encoding the parental enzyme. The parental enzyme may be encoded by SEQ ID NO: 1, SEQ ID NO: 4 or SEQ ID NO: 6 or a sequence which is at least 65%, more preferably at least 70%, more preferably at least 75%, more preferably at least 80%, more preferably at least 85%, even more preferably at least 90%, most preferably at least 95% identical to one of these sequences and which encode an active polypeptide. The variant polypeptide sequence is preferably one which is not found in nature.

Wild-Type Enzyme:

The term "wild-type" xyloglucanase denotes a xyloglucanase expressed by a naturally occurring microorganism, such as bacteria, yeast, or filamentous fungus found in nature. The term wild-type may be used interchangeably with the term "naturally occurring".

Parent Enzyme:

The term "parent" xyloglucanase or "parental" xyloglucanase as used herein means a xyloglucanase to which a modification, e.g., substitution(s), insertion(s), deletion(s), and/or truncation(s), is made to produce the enzyme variants of the present invention. This term also refers to the polypeptide with which a variant is compared and aligned. The parent may be a naturally occurring (wild-type) polypeptide such as the enzyme of SEQ ID NO:2 or SEQ ID NO:3 or SEQ ID NO: 5 or SEQ ID NO: 7 or a polypeptide which is at least 65%, more preferably at least 70%, more preferably at least 75%, more preferably at least 80%, more preferably at least 85%, even more preferably at least 90%, most preferably at least 95% identical to one of these sequences. The parent polypeptide may also be a variant of a naturally occurring polypeptide which has been modified or altered in the amino acid sequence. A parent may also be an allelic variant, which is a polypeptide encoded by any of two or more alternative forms of a gene occupying the same chromosomal locus.

Isolated Variant or Polypeptide:

The term "isolated variant" or "isolated polypeptide" as used herein refers to a variant or a polypeptide that is isolated from a source, e.g. the host cell from which it is expressed or the enzyme complex it is normally present in. Preferably, the polypeptide is at least 40% pure, more preferably at least 60% pure, even more preferably at least 80% pure, most preferably at least 90% pure, and even most preferably at least 95% pure, as determined by SDS-PAGE.

Substantially Pure Variant or Polypeptide:

The term "substantially pure variant" or "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure variant or polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The variants and polypeptides of the present invention are preferably in a substantially pure form. This can be accomplished, for example, by preparing the variant or polypeptide by well-known recombinant methods or by classical purification methods.

Mature Polypeptide:

The term "mature polypeptide" is defined herein as a polypeptide having xyloglucanase activity that is in its final form following translation and any post-translational modifications, such as N-terminal processing, C-terminal truncation, glycosylation, phosphorylation, etc. For the polypeptide defined by SEQ ID NO: 2, the mature xyloglucanase sequence may in theory start at position 28 of SEQ ID NO: 2. The mature sequence ends at position 551 of SEQ ID NO: 2. The theoretical mature xyloglucanase sequence is show in SEQ ID NO: 3. Depending on expression system the length of the actual mature polypeptide may vary 1 to 10 amino acids in length based on the theoretical mature polypeptide. The mature polypeptide may for example start at position 33 of SEQ ID NO: 2 and ends at position 551 of SEQ ID NO: 2.

Mature Polypeptide Coding Sequence:

The term "mature polypeptide coding sequence" is defined herein as a nucleotide sequence that encodes a mature polypeptide having xyloglucanase activity. In one aspect, the mature polypeptide coding sequence is nucleotides 82 to 1653 of SEQ ID NO: 1. The mature polypeptide coding sequence may vary 3 to 30 nucleotides in length depending on the expression system. The mature polypeptide coding sequence can for example correspond to nucleotides 97 to 1653 of SEQ ID NO: 1.

Identity:

The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277; http://emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra; http://emboss.org), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment−Total Number of Gaps in Alignment)

Functional Fragment:

The term "functional fragment of a polypeptide" is used to describe a polypeptide which is derived from a longer polypeptide, e.g., a mature polypeptide, and which has been truncated either in the N-terminal region or the C-terminal region or in both regions to generate a fragment of the parent polypeptide. To be a functional polypeptide the fragment must maintain at least 20%, preferably at least 40%, more preferably at least 50%, more preferably at least 60%, more preferably at least 70%, more preferably at least 80%, even more preferably at least 90%, most preferably at least 95%, and even most preferably at least 100% of the xyloglucanase activity of the full-length/mature polypeptide.

Allelic Variant:

The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated Polynucleotide:

The term "isolated polynucleotide" as used herein refers to a polynucleotide that is isolated from a source. In one aspect, the isolated polynucleotide is at least 40% pure, more preferably at least 60% pure, even more preferably at least 80% pure, and most preferably at least 90% pure, and even most preferably at least 95% pure, as determined by agarose electrophoresis.

Substantially Pure Polynucleotide:

The term "substantially pure polynucleotide" as used herein refers to a polynucleotide preparation free of other extraneous or unwanted nucleotides and in a form suitable for use within genetically engineered polypeptide production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding Sequence:

When used herein the term "coding sequence" means a polynucleotide, which directly specifies the amino acid sequence of its polypeptide product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Operably Linked:

The term "operably linked" denotes herein a configuration in which a control sequence is placed at an appropriate position relative to the coding sequence of the polynucleotide sequence such that the control sequence directs the expression of the coding sequence of a polypeptide.

Host Cell:

The term "host cell", as used herein, includes any cell type that is susceptible to transformation, transfection, transduction, and the like with a nucleic acid construct or a vector comprising a polynucleotide of the present invention. The term "host cell" encompasses any progeny of a parent cell that is not identical to the parent cell due to mutations that occur during replication.

Improved Chemical Stability:

The term "improved chemical stability" is defined herein as a variant enzyme displaying retention of enzymatic activity after a period of incubation in the presence of a chemical or chemicals, either naturally occurring or synthetic, which reduces the enzymatic activity of the parent enzyme. Improved chemical stability may also result in variants better able to catalyze a reaction in the presence of such chemicals. In a particular aspect of the invention the improved chemical stability is an improved stability in a detergent, in particular in a liquid detergent. The improved detergent stability is in particular an improved stability of the xyloglucanase activity when a xyloglucanase variant of the present invention is mixed into a liquid detergent formulation and then stored at temperatures between 15 and 50° C.

In the present invention liquid detergents are particular useful as liquid laundry detergents.

Conventions for Designation of Variants

For purposes of the present invention, the amino acid sequence of the xyloglucanase disclosed in SEQ ID NO: 3 is used to determine the corresponding amino acid residue in another xyloglucanase. The amino acid sequence of another xyloglucanase is aligned with the amino acid sequence of the xyloglucanase disclosed in SEQ ID NO: 3, and based on the alignment the amino acid position number corresponding to any amino acid residue in the amino acid sequence of the xyloglucanase disclosed in SEQ ID NO: 3 can be determined.

An alignment of polypeptide sequences may be made, for example, using "ClustalW" (Thompson, J. D., Higgins, D. G. and Gibson, T. J., 1994, CLUSTAL W: Improving the sensitivity of progressive multiple sequence alignment through sequence weighting, positions-specific gap penalties and weight matrix choice, *Nucleic Acids Research* 22: 4673-4680). An alignment of DNA sequences may be done using the polypeptide alignment as a template, replacing the amino acids with the corresponding codon from the DNA sequence.

In describing the various xyloglucanase variants of the present invention, the nomenclature described below is adapted for ease of reference. In all cases, the accepted IUPAC single letter or triple letter amino acid abbreviation is employed.

Substitutions.

For an amino acid substitution, the following nomenclature is used: original amino acid/position/substituted amino acid. Accordingly, the substitution of threonine with alanine at position 226 is designated as "Thr226Ala" or "T226A". Multiple mutations are separated by addition marks ("+"), e.g., "G205R+S411F", representing mutations at positions 205 and 411 substituting glycine (G) with arginine (R), and serine (S) with phenylalanine (F), respectively. Where an original amino acid may be substituted by an amino acid selected from a group it is designated as "K129R,S,A,I,F,Q" representing the substitution of a lysine (K) at position 129 with an amino acid selected from the group consisting of: arginine (R), serine (S), alanine (A), isoleucine (I), phenylalanine (F) and glutamine (Q). Alternatively, "K129R,S,A,I,F,Q" could be written as K129R or K129S, or K129A, or K129I or K129F or K129Q Deletions.

For an amino acid deletion, the following nomenclature is used: Original amino acid/position/asterisk (*). Accordingly, the deletion of glycine at position 195 is designated as "Gly195*" or "G195*". Multiple deletions are separated by addition marks ("+"), e.g. G195*+S411*".

Insertions.

For an amino acid insertion, the following nomenclature is used: Asterisk (*)/position/lower case letter/inserted amino acid, where the lower case letter indicates the addition of an amino acid down stream of the position number. Accordingly, the insertion of a glutamic acid (E) down stream of position 10 is designated "*10aE". If a second amino acid, e.g. a valine (V), is to be inserted down stream of position 10 after the glutamic acid (E) it is designated "*10aE+*10bV". Additions to the N-terminal of the polypeptide are designated with a 0 (zero). The addition of a glutamic acid (E) and a valine (V) added to the N-terminal amino acid of a polypeptide is designated as *0aE+*0bV. A "downstream" insertion can also be described as the addition of one or more amino acids between the named position and the position immediately following the named position, e.g. an insertion downstream of position 195 results in the addition of one or more amino acids between position 195 and 196, thereby generating new positions *195a, *195b and so forth.

Parent Xyloglucanases

In the present invention, the parent xyloglucanase is either (a) a xyloglucanase belonging to family 44 of glycosyl hydrolases also termed family 44 xyloglucanases; or (b) a polypeptide selected from the group consisting of SEQ ID NO:3, SEQ ID NO: 5 and SEQ ID NO: 7; or (c) a polypeptide comprising an amino acid sequence having at least 75% identity with the mature polypeptide of SEQ ID NO: 3; or (d) a polypeptide encoded by a polynucleotide that hybridizes under at least medium stringency conditions with (i) the mature polypeptide coding sequence of SEQ ID NO: 1 or SEQ ID NO: 4 or SEQ ID NO: 6, (ii) the genomic DNA sequence comprising the mature polypeptide coding sequence of SEQ ID NO: 1 or SEQ ID NO: 4 or SEQ ID NO: 6 or (iii) a full-length complementary strand of (i) or (ii); or (e) a polypeptide encoded by a polynucleotide comprising a nucleotide sequence having at least 70% identity with the mature polypeptide coding sequence of SEQ ID NO: 1.

In a first aspect, the parent xyloglucanase comprise an amino acid sequence having a degree of identity to the mature polypeptide of SEQ ID NO: 3 of preferably at least at least 70%, more preferably at least 75%, more preferably at least 80%, more preferably at least 85%, more preferably at least 90%, more preferably at least 95%, more preferably at least 96%, even more preferably at least 97%, most preferably at least 98%, or even most preferably at least 99%, which have xyloglucanase activity (hereinafter "homologous polypeptides"). In one aspect, the homologous polypeptides have an amino acid sequence that differs by ten amino acids, preferably by nine, more preferably by eight, more preferably by seven, more preferably by six, more preferably by five amino acids, more preferably by four amino acids, even more preferably by three amino acids, most preferably by two amino acids, and even most preferably by one amino acid from the mature polypeptide of SEQ ID NO: 3.

Substantially homologous parent xyloglucanases may have one or more (several) amino acid alterations such as substitutions, deletions and/or insertions. These changes are preferably of a minor nature, that is conservative amino acid substitutions and other substitutions that do not significantly affect the three-dimensional folding or activity of the protein or polypeptide; small deletions, typically of one to about 9 amino acids, preferably from one to about 15 amino acids and most preferably from one to about 30 amino acids; and small amino- or carboxyl-terminal extensions, such as an amino-terminal methionine residue, a small linker peptide of up to about five to ten residues, preferably from 10 to 15 residues and most preferably from 20 to 25 residues, or a small extension that facilitates purification (an affinity tag), such as a poly-histidine tag, or protein A (Nilsson et al., 1985, *EMBO J.* 4: 1075; Nilsson et al., 1991, *Methods Enzymol.* 198: 3. See, also, in general, Ford et al., 1991, *Protein Expression and Purification* 2: 95-107.

Although the changes described above preferably are of a minor nature, such changes may also be of a substantive nature such as fusion of larger polypeptides of up to 300 amino acids or more both as amino- or carboxyl-terminal extensions.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by Neurath and Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in the xyloglucanase polypeptides of the present invention can be identified according to procedures known in the art, such as site-directed mutagenesis or alanine-scanning mutagenesis (Cunningham and Wells, Science 244: 1081-1085, 1989). In the latter technique, single alanine mutations are introduced at every residue in the molecule, and the resultant mutant molecules are tested for biological activity (i.e. xyloglucanase activity) to identify amino acid residues that are critical to the activity of the molecule. See also, Hilton et al., J. Biol. Chem. 271:4699-4708, 1996. The active site of the enzyme or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-312, 1992; Smith et al., J. Mol. Biol. 224:899-904, 1992; Wlodaver et al., FEBS Lett. 309:59-64, 1992. The identities of essential amino acids can also be inferred from analysis of homologies with polypeptides which are related to a polypeptide according to the invention. The crystal structure of an enzyme belonging to the family 44 glycosyl hydrolases has been published by Kitago et. al, J. Biol. Chem. Vol. 282: 35703-35711, 2007. Based on this structure it is possible to generate a three dimensional structure of the parent xyloglucanase (SEQ ID NO: 3) in silico. Based on comparison with the published structure the following residues in SEQ ID NO: 3 have been identified as critical for the enzymatic function E187 (Catalytic—Acid/Base), E358 (Catalytic—Nucleophile), E56 (Carboxylate group coordinating Ca2+) and D154 (Carboxylate group coordinating Ca2+). These positions should, therefore, preferably not be mutated in the parent enzyme.

The parent xyloglucanase preferably comprises the amino acid sequence of SEQ ID NO: 3 or an allelic variant thereof; or a fragment thereof having xyloglucanases activity. In one aspect, the parent xyloglucanase comprises the amino acid sequence of SEQ ID NO: 2. In another aspect, the parent xyloglucanase comprises the mature polypeptide of SEQ ID NO: 2. In another aspect, the parent xyloglucanase consists of the amino acid sequence of SEQ ID NO: 3 or an allelic variant thereof; or a fragment thereof having xyloglucanase activity. In another aspect, the parent xyloglucanase comprises the amino acid sequence of SEQ ID NO: 5, or an allelic variant thereof; or a fragment thereof having xyloglucanase activity. In another aspect, the parent xyloglucanase comprises the amino acid sequence of SEQ ID NO: 7, or an allelic variant thereof; or a fragment thereof having xyloglucanase activity. In another aspect the parent xyloglucanase comprises an amino acid sequence which is at least 65%, more preferably at least 70%, more preferably at least 75%, more preferably at least 80%, more preferably at least 85%, even more preferably at least 90%, most preferably at least 95% identical SEQ ID NO: 2, or SEQ ID NO: 3 or SEQ ID NO: 5. A fragment of the mature polypeptide of SEQ ID NO: 3 is a polypeptide having one or more (several) amino acids deleted from the amino- and/or carboxyl-terminus of this amino acid sequence and still maintaining xyloglucanase activity.

In a second aspect, the parent xyloglucanases are encoded by polynucleotides that hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1 or SEQ ID NO: 4 or SEQ ID NO: 6, (ii) the genomic DNA sequence comprising the mature polypeptide coding sequence of SEQ ID NO: 1 or SEQ ID NO: 4 or SEQ ID NO: 6, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). The subsequence may encode a polypeptide fragment having xyloglucanase activity. In one aspect, the complementary strand is the full-length complementary strand of the mature polypeptide coding sequence of SEQ ID NO: 1 or SEQ ID NO: 4 or SEQ ID NO: 6.

A subsequence of the mature polypeptide coding sequence of SEQ ID NO: 1 or SEQ ID NO: 4 or SEQ ID NO: 6, or a homolog thereof, is a nucleotide sequence where one or more (several) nucleotides have been deleted from the 5'- and/or 3'-end, where the polypeptide encoded by the subsequence possess xyloglucanase activity.

The parent enzymes may also be allelic variants of the polypeptides that have xyloglucanase activity.

The polynucleotide of SEQ ID NO: 1 or SEQ ID NO: 4 or SEQ ID NO: 6; or a subsequence thereof; as well as the amino acid sequence of SEQ ID NO: 3 or SEQ ID NO: 5 or SEQ ID NO: 7; or a fragment thereof; may be used to design nucleic acid probes to identify and clone DNA encoding parent xyloglucanases from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, preferably at least 900 nucleotides in length, preferably at least 1000 nucleotides in length, preferably at least 1100 nucleotides in length, preferably at least 1200 nucleotides in length, preferably at least 1300 nucleotides in length, preferably at least 1400 nucleotides in length, preferably at least 1500 nucleotides in length or most preferably at least 1600 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA library prepared from other organisms may be screened for DNA that hybridizes with the probes described above and encodes a parent xyloglucanase. Genomic or other DNA from other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, or a subsequence thereof, the carrier material is used in a Southern blot. For purposes of the present invention, hybridization indicates that the polynucleotide hybridizes to a labeled nucleotide probe corresponding to the polynucleotide shown in SEQ ID NO: 1, its complementary strand, or a subsequence thereof, under low to very high stringency conditions. Molecules to which the probe hybridizes can be detected using, for example, X-ray film or any other detection means known in the art.

In one aspect, the nucleic acid probe is the mature polypeptide coding sequence of SEQ ID NO: 1. In another aspect, the nucleic acid probe is nucleotides 82 to 1653 of SEQ ID NO: 1, or nucleotides 97 to 1653 of SEQ ID NO: 1. In another aspect, the nucleic acid probe is a polynucleotide sequence that encodes the polypeptide of SEQ ID NO: 2, or a subsequence thereof. In another aspect, the nucleic acid probe is SEQ ID NO: 1.

For long probes of at least 100 nucleotides in length, very low to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes that are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the parent xyloglucanase is encoded by a polynucleotide comprising or consisting of a nucleotide sequence having a degree of identity to the mature polypeptide coding sequence of SEQ ID NO: 1 of preferably at least 65%, more preferably at least 70%, more preferably at least 75%, more preferably at least 80%, more preferably at least 85%, even more preferably at least 90%, most preferably at least 95%, and even most preferably 96%, 97%, 98%, or 99%, which encode an active polypeptide. In one aspect, the mature polypeptide coding sequence is nucleotides 82 to 1653 of SEQ ID NO: 1, or nucleotides 97 to 1653 of SEQ ID NO: 1.

The parent xyloglucanase may be obtained from microorganisms of any genus. In one aspect, the parent xyloglucanase is secreted extracellularly.

In a further aspect the parent xyloglucanase may be a bacterial xyloglucanase. For example, the xyloglucanase may be a Gram positive bacterial polypeptide such as a *Bacillus*, preferably from the *Bacillus/Lactobacillus* subdivision, preferably a species from the genus *Paenibacillus*, especially *Paenibacillus polymyxa*, e.g. *Paenibacillus polymyxa*, ATCC 832, preferably the xyloglucanase is a family 44 xyloglucanase, e.g. as described in WO 01/62903, more preferably the xyloglucanase of SEQ ID NO: 5, more preferably the xyloglucanase of SEQ ID NO: 7, and most preferably the xyloglucanase of SEQ ID NO: 2 or the mature polypeptide thereof.

Generation of Variants

Variants of a parent xyloglucanase can be prepared according to any mutagenesis procedure known in the art, such as random and/or site-directed mutagenesis, synthetic gene construction, semi-synthetic gene construction, random mutagenesis, shuffling, etc.

Synthetic gene construction entails in vitro synthesis of a designed polynucleotide molecule to encode a polypeptide molecule of interest. Gene synthesis can be performed utilizing a number of techniques, such as the multiplex microchip-based technology described by Tian, et. al., (Tian, et. al., *Nature* 432:1050-1054) and similar technologies wherein oligonucleotides are synthesized and assembled upon photo-programmable microfluidic chips.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide fragments may then be shuffled.

Site-directed mutagenesis is a technique in which one or several mutations are created at a defined site in a polynucleotide molecule encoding the parent xyloglucanase. The technique can be performed in vitro or in vivo.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent xyloglucanase and subsequent ligation of an oligonucleotide containing the mutation in the polynucleotide. Usually the restriction enzyme that digests at the plasmid and the oligonucleotide is the same, permitting sticky ends of the plasmid and insert to ligate to one another. For further description of suitable techniques reference is made to Sambrook et al. (1989), Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for *Bacillus*". John Wiley and Sons, 1990), and WO 96/34946; Scherer and Davis, 1979, *Proc. Natl. Acad. Sci. USA* 76: 4949-4955; and Barton et al., 1990, *Nucleic Acids Research* 18: 7349-4966.

After the ligase reaction the ligation mixture may be used to transform a host cell, for cloning purposes *E. coli* cells are often used as described in Ausubel, F. M. et al. The transformed *E. coli* cells can be propagated in liquid media or on solid agar plates, plasmids can be rescued from the transformed cells and used to transform *B. subtilis* cells. Suitable competent *Bacillus* cells, such as MB1510, an 168-derivative (e.g. available from BGSC with accession no. 1A1 168 trpC2), may be transformed as described in WO 03/095658. An *E. coli* plasmid-borne integration cassette for library construction may be used for *Bacillus* transformation. The method is described in detail in WO 03/095658. Alternatively, an in vitro amplified PCR-SOE-product (Melnikov and Youngman, Nucleic Acid Research 27, 1056) may be used.

Site-directed mutagenesis can be accomplished in vivo by methods known in the art. See, for example, U.S. Patent Application Publication 2004/0171154; Storici et al., 2001, *Nature Biotechnology* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants of a parent xyloglucanases.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223, 409; WO 92/06204) and region-directed mutagenesis (Derbyshire et al., 1986, *Gene* 46:145; Ner et al., 1988, *DNA* 7:127).

Mutagenesis/shuffling methods as described above can be combined with high-throughput, automated screening methods to detect the activity of cloned, mutagenized polypeptides expressed by host cells, e.g. *Bacillus* as described above.

Mutagenized DNA molecules that encode polypeptides with xyloglucanase activity can be recovered from the host cells and rapidly sequenced using standard methods in the art.

Variants

In the present invention, the isolated variants of a parent xyloglucanase comprise an alteration at one or more (several) positions selected from the group consisting of positions number 68, 123, 156, 118, 200, 129, 137, 193, 92, 83, 149, 34, 340, 332, 9, 76, 331, 310, 324, 498, 395, 366, 1, 374, 7, 140, 8, 14, 21, 211, 37, 45, 13, 78, 87, 436, 101, 104, 111, 306, 117, 119, 414, 139, 268, 142, 159, 164, 102, 168, 176, 180, 482, 183, 202, 206, 217, 4, 222, 19, 224, 228, 232, 2, 240, 244, 5, 247, 249, 328, 252, 259, 406, 267, 269, 275, 179, 166, 278, 281, 288, 298, 301, 18, 302, 165, 80, 303, 316, 169, 322, 120, 146, 342, 348, 147, 353, 380, 468, 382, 383, 38, 384, 389, 391, 10, 392, 396, 177, 397, 399, 409, 237, 413, 253, 415, 418, 40, 443, 445, 148, 449, 225, 450, 454, 3, 455, 456, 299, 461, 470, 204, 476, 488, 347, and 507, wherein the variant having xyloglucanase activity comprises an amino acid sequence having a degree of identity of at least 70%, more preferably at least 75%, more preferably at least 80%, more preferably at least 85%, even more preferably at least 90%, more preferably at least 95%, more preferably at least about 97%, most preferably at least 98% and even more preferably 99% to the amino acid sequence of the parent xyloglucanase. The numbering of the positions are relative to the amino acid sequence of SEQ ID NO: 3. Preferably, the variants comprising alterations at one or more of the above identified positions have an increased stability in detergent, preferably in liquid detergent as compared to the parent xyloglucanase.

In a preferred embodiment the variant comprises one or more (several) of the following combinations of alterations:
V1*+V2*+H3*;
V1Q+*1aE+*1bV;
H3A;
H3A+H436A;
K8A,Q,S;
T9D;
T9D+L34F+A83E+Q149E+H193T+S332P+R340T;
I10V+D33E+M40L+A41T+Q67M+Y73F+S76D+G78A+ Q82K+T92A+L102Q+Q137E+I222V+V228I+D249N+ S269N+V272A+E333A+I337L+M356L+T374A+S416A+ D444Y+A469E+K470T+I473G+T517A+S522*;
I10V+F17S+D33E+M40L+A41T+Q67M+N72S+S76D+ G78A+Q82K+Q137E+V219A+D249N+V272A+I337L+ M356L+V397A+S416A+T421I+S424N+N441D+D444Y+ V450I+K470T+I473S+V477I;
I10V+F17S+D33E+M40L+Q67M+N72S+S76D+G78A+ Q82K+T92A+L102Q+Q137E+H164N+N168K+T172A+ V219A+I222V+V228I+D249N+S269N+V272A+E333A+ I337L+M356L+N415S+T421I+S424H+N441D+D444Y+ S522P+P523V+V524E;
I10V+F17S+D33E+M40L+Q67M+N72S+S76D+G78A+ Q82K+T92A+L102Q+Q137E+I222V+V228I+D249N+ V272A+I337L+M356L+T374A+V397A+S416A+T421I+ S424N+N441D+D444Y+V450I+A469E+K470T+I473G+ T517A+S522P+P523V+V524E;
I10V+F17S+D33E+Q67M+N72S+S76D+G78A+Q82K+ T92A+L102Q+Q137E+N168K+T172A+I222V+V228I+ D249N+V272A+E333A+I337L+M356L+V397A+S416A+ T421I+S424H+N441D+D444Y+A469E+K470T+I473S+ V477I+E489A+A490V+T517A+S522*;
I10V+F17S+M40L+Q67M+N72S+S76D+G78A+Q82K+ T92A+L102Q+Q137E+I222V+V228I+D249N+S269N+ V272A+T320A+I337L+M356L+T374A+V397A+N415S+ T421I+S424H+N441D+D444Y+A469E+K470T+I473S+ V477I+T517A+S522P+P523V+V524E;
I10V+F17S+Q67M+N72S+S76D+G78A+Q82K+T104A+ Q137E+N153K+R156Q+V219A+I222V+V228I+D249N+ S269N+V272A+E333A+I337L+M356L+V397A+N415S+ D420G+T421I+S424H+N441D+D444Y+V450I+A469E+ K470T+I473G+T517A+S522*;
I10V+F17S+Q67M+N72S+S76D+G78A+Q82K+T92A+ T104A+Q137E+R156Q+V159A+H164N+N168K+I172A+ I222V+V228I+D249N+V272A;
I10V+F17S+Y53H+Q67M+N72S+S76D+G78A+Q82K+ T92A+L102Q+Q137E+T172V+A177T+I222V+V228I+ D249N+S269N+I337L+M356L+V397A+S416A+T421I+ S424H+N441D+D444Y+A469E+K470T+I473G+T517A+ S522*;
K13A+K129A;
K13A+Q68H+T92V+K118A+Q137E+R156Y+G200P;
K13A,R;
K18R;
R20A;
K21Q+K129A;
K21Q,R,T;
Q32H+M40L+R49G+D65E+Q67M+N72S+S76D+G78A+ Q82K+T92A+L102Q+T104A+Q137E+H164N+K202E+ I222V+V228I+D249N+M356L+T374A;
D33V+Q68H+N168H+V450I;
L34F,I,M,V;
L34I+K129A;
D37G,N+K129A+R156Y;
E38I,V;
M40L+A41T+Q67M+N72S+S76D+G78A+Q82K+ Q137E+N153K+H164N+D249N+V272A+I337L+M356L+ V397A+N415S+T421I+S424N+N441D+V450I+E489A+ A490V+T517A+S522*;
M40V;
L45I;
Q68H,M,N;
Q68H+G200P+N331F;
Q68H+K118A+K129A+R156Y+G200P+N331F;
Q68H+K118A+R156V+G200P+N331F;
Q68H+K118A+R156Y+H193T+D366H;
Q68H+K118R+R156F,Y;
Q68H+K118R+R156Y+G200P;
Q68H+K118S+R156F+G200P+G274D+N331F;
Q68H+K129A,T+R156K+G200P+N331F;
Q68H+R156F,V,Y+G200P+N331F;
Q68H+R156Y;
Q68H+R156Y+H193T;
Q68H+R156Y+H193T+D366H;
Q68H+R156Y+H193T+G200P+M310V;
Q68H+S76W+T92V+K118A+Q137E+R156Y+G200P+ N331F;
Q68H+T92A,D,I,S,V,Y+K118A+K129A+R156Y+G200P+ N331F;
Q68H+T92N+D97N+K118A+K129A+R156Y+G200P+ N331F;
Q68H+T92S+K118A+K129A+R156Y+G200P+G274D+ N331F;
Q68H+T92V+G200P+M310V;
Q68H+T92V+G200P+M310V+N331F;
Q68H+T92V+K118A+K129A+Q137E+R156Y+G200P+ A224P+N331F;
Q68H+T92V+K118A+K129A+Q137E+R156Y+G200P+ N331F;
Q68H+T92V+K118A+K129A+Q137E+R156Y+H193T;
Q68H+T92V+K118A+K129A+Q137E+R156Y+H193T+ D366H;
Q68H+T92V+K118A+K129A+Q137E+R156Y+H193T+ G200P+M310V+E446K;

Q68H+T92V+K118A+K129A+Q137E+R156Y+H193T+
N331H,K,Q;
Q68H+T92V+K118A+K129A+R156Y+H193T;
Q68H+T92V+K118A+K129A+R156Y+H193T+D366H;
Q68H+T92V+K118A+K129A+R156Y+H193T+G200P+
M310V;
Q68H+T92V+K118A+Q137E+N140F+R156Y+G200P+
K470T;
Q68H+T92V+K118A+Q137E+R156Y+G200P+D324N;
Q68H+T92V+K118A+Q137E+R156Y+G200P+K470T;
Q68H+T92V+K118A+Q137E+R156Y+G200P+M310L;
Q68H+T92V+K118A+Q137E+R156Y+G200P+N331F;
Q68H+T92V+K118A,R+R156Y,F;
Q68H+T92V+K118A+S123P,T+K129A+Q137E+R156Y+
G200P+N331F;
Q68H+T92V+K118R+R156Y+H193T+D366H;
Q68H+T92V+R156F+G200P+M310V+S484C;
Q68H+T92V+R156F,V,Y+G200P+M310V;
Q68H+T92V+R156F,V,Y+G200P+M310V+N331F;
Q68H+T92V+R156F,Y+H193T;
Q68H+T92V+R156F,Y+H193T+D366H;
Q68H+T92V+R156F,Y+H193T+G200P+M310V;
Q68H+T92V+R156Y;
S76E,I,K,M,R,T,V,W;
S76W+G200P;
S76W+G200P+A224P;
G78A+K118A++K129A+R156Y;
G78A+K118A+K129A+R156Y;
G78A+K118A+K129A+R156Y+G200P+N331F;
G78A+K118A+K129A+R156Y+K169A;
G78A,N,S;
G78A+T92V+K118A+K129A+R156Y;
G78A+T92V+K118A+K129A+R156Y+G200P+N331F;
G78A+T92V+K118A+K129A+R156Y+K169A;
L80V;
A83D,E,H,I,L,N,R,S,T,Y;
K87Q;
K87V+K129A+K169A;
T92I,V;
T92V+K118A+K129A+Q137E+R156Y+G200P+N331F;
T92V+K118A+K129A+R156Y;
T92V+K118A+K129A+R156Y+G200P+N331F;
T92V+K118A+K129A+R156Y+H164N+G200P+N331F;
T92V+K129A+R156Y;
K101A+K129A;
K101R;
K101R+L102I;
T104A+P111Q+A117S+K129A+R156Y;
P111Q;
K118A+K129A;
K118A+K129A+F146L+R156Y+G200P+N331F;
K118A+K129A+Q137E+R156Y+G200P+N331F;
K118A+K129A+R156Y;
K118A+K129A+R156Y+A224P;
K118A+K129A+R156Y+G200P;
K118A+K129A+R156Y+G200P+M310V+N331F;
K118A+K129A+R156Y+G200P+N331F;
K118A+K129A+R156Y+G200P+N331F+N399I;
K118A+K129A+R156Y+K169A+G200P+N331F;
K118A+K129A+R156Y+K470T;
K118A,R;
K118A+R156Y;
K118A+R156Y+G200P;
D119L;
G120A;
S123P,T;
S123T+K129A+R156Y;

K129A,F,I,K,R,S,T;
K129A+K169A;
K129A+K176P;
K129A+K275Q;
K129A+K445S;
K129A+K470T;
K129A+Q137E+R156Y;
K129A+Q137E+R156Y+G200P;
K129A+Q137E+R156Y+K470T;
K129A+Q137E+V139K+N140F+Q147S+R156Y;
K129A+R156Y;
K129A+R156Y+A177T+V179I+A183S;
K129A+R156Y+A328G;
K129A+R156Y+D247G;
K129A+R156Y+D249G,N,S;
K129A+R156Y+D303I,K,S,V;
K129A+R156Y+D324N;
K129A+R156Y+D366H+374A;
K129A+R156Y+D461N,Q,T;
K129A+R156Y+E288Q;
K129A+R156Y+G200P;
K129A+R156Y+G200P+G204T+R211K;
K129A+R156Y+H164N;
K129A+R156Y+H436Y;
K129A+R156Y+I10V+V14I+D19E;
K129A+R156Y+I222V+A224P+V228I+V232A;
K129A+R156Y+K176P,S;
K129A+R156Y+K275T;
K129A+R156Y+K322I+K454Q;
K129A+R156Y+K406N+N415G;
K129A+R156Y+K454Q;
K129A+R156Y+L380F+N383Y+D384G+N389T;
K129A+R156Y+N298F+E299N+G301T;
K129A+R156Y+N302K+D303L,S;
K129A+R156Y+N331F;
K129A+R156Y+P507A;
K129A+R156Y+R267H;
K129A+R156Y+R409L,T;
K129A+R156Y+S443D+K445S+L449I+V450I+S455N+
M456Y;
K129A+R156Y+T244D;
K129A+R156Y+V159M+H164N+F165Y;
K129A+R156Y+V259I+R267K+L268K+S269A;
Q137D,E;
N140F;
K142A,Q,R;
F146C+H164C;
F146K,L;
F146L+K322I;
L148K+N168D;
Q149E;
R156A,D,E,F,I,K,L,M,N,P,Q,R,S,T,V,W,Y;
R156Y+N331F;
V159M;
H164A,N;
L166I;
N168D;
K169A,Q,R;
K176P;
A177E,T;
K180R;
H193A,D,S,T;
R197A,L;
H199A;
G200A,C,D,E,F,H,I,K,L,M,N,P,Q,R,S,T,V,W,Y;
G200P+A224P;
K202N,Q,R;

S214E;
K217A;
A221K;
G225S;
V232A;
G237A,S,V;
K240A,Q,R;
K252A,Q,R;
G253A;
R267A;
L268I;
K275A,Q,R;
L278I;
F281L;
M290R;
R295A;
K306A,R;
K307Q;
M310I,L,V;
M310V+N399I;
R314A;
G316I;
K322A,R;
D324N;
N331A,C,D,E,F,G,H,I,K,L,M,P,Q,R,S,T,V,W,Y;
S332M,P;
S332P+V397I;
R340A,N,T;
K342A;
V345I;
K347A,Q,R;
D348G;
K353Q,R;
D366H;
M373Q;
T374A;
L380F;
K382A;
N383Y;
N389A,F,N,V;
W391V;
K392G,Q;
D395G;
G396P;
V397S;
N399I;
K406N;
G413A,S;
K414A;
N415S;
T417K;
F418I;
V431E;
H436A;
N441G+A442E+S443D;
S443E,K,Q;
K445A,R,S;
K445C+K470C;
H448A;
K454R;
S467R+G468S+A469T;
G468S,Y;
K470P,R,T;
I473T;
K476Q;
K482A,Q,R;
K488A,Q,R,T;
A490R;
G498A,D,S;
R500A,T,V;
H512A;
T517A+G518D; or
G518D;

In one aspect, the number of amino acid alterations in the variants of the present invention comprise preferably the total number of 55, preferably 52, more preferably 50, more preferably 40, more preferably 30, more preferably 20, more preferably 15, more preferably ten, more preferably nine, more preferably eight, even more preferably seven, even more preferably six, even more preferably five, even more preferably four, even more preferably three, and most preferably two alterations, and most preferably one alteration. In another aspect the total number of alterations is one, preferably two, more preferably three, even more preferably four, even more preferably five, even more preferably six, even more preferably seven, even more preferably eight, even more preferably nine, most preferably ten. The alteration may be in the form of i) an insertion of an amino acid downstream of the amino acid which occupies the position; ii) deletion of the amino acid which occupies the position, or iii) a substitution of the amino acid which occupies the position with a different amino acid. The alterations may be made independently of each other, for example in one position there may be an insertion while there is a substitution at a second position and a deletion at a third position as compared to the parental xyloglucanase. In a preferred embodiment the variant only comprises substitutions.

In one aspect of the invention positions to be mutated are identified based on consensus sequence analysis. The analysis is performed by aligning SEQ ID NO: 3, with SEQ ID NO: 5 and SEQ ID NO: 7 as well as with other sequences from the uniprot database which are 30% identical to the family 44 glycosyl hydrolase region of SEQ ID NO: 3. The resulting consensus sequences are shown in FIG. 1. Consensus sequence 1 is the sequence comprising the most abundant amino acid at a given position from the alignment, consensus sequence 2 is the sequence with the $2^{nd}$ most abundant amino acid at a given position and so forth. In one aspect of the invention, one or more (several) residues of SEQ ID NO: 3 are replaced by the corresponding residue from Consensus sequence 1 or Consensus sequence 2 or Consensus sequence 3 or Consensus sequence 4. In one aspect of the present invention the variants comprise an alteration at one or more (several) of the positions selected from the group of 52 positions identified by the consensus sequence analysis consisting of position number 10, 19, 68, 80, 89, 104, 111, 117, 123, 129, 137, 139, 140, 147, 156, 159, 164, 165, 177, 179, 183, 200, 204, 211, 222, 224, 225, 228, 232, 259, 267, 268, 269, 281, 328, 345, 366, 374, 380, 383, 384, 406, 415, 436, 443, 445, 449, 450, 455, 456, 488 and 507. In a preferred embodiment the alteration is a substitution, or several substitutions, selected from the group consisting of: I10V, D19E, Q68H, L80V, G89A, T104A, P111Q, A117S, S123P, K129T, Q137E, V139K, N140F, Q147S, R156Y, V159M, H164N, F165Y, A177T, V179I, A183S, G200P, G204T, R211K, I222V, A224P, G225S, V228I, V232A, V259I, R267K, L268K, S269A, F281L, A328G, V345I, D366H, T374A, L380F, N383Y, D384G, K406N, N415G, H436Y, S443D, K445S, L449I, V450I, S455N, M456Y, K488T and P507A.

In another aspect of the invention the variant is generated by changing those amino acids in the parental peptide which have a positive charges and are situated within 20 Å of the calcium ion to neutral or negative charged amino acids. Preferred variants of the present invention comprise variants in which the overall charge within 20 Å from the calcium ion has been made more negative. In such variants positively charged amino acids may have been replaced with amino acids that are neutral or negatively charged under the application conditions. In accordance herewith, preferred variants may have an amino acid residue which is partly or fully positively charged under the "chemical stability" or application conditions, i.e. a Lys, Arg or His replaced by a negative or neutral amino acid. Preferred replacement amino acids may be negatively charged amino acids as Asp and Glu or neutral amino acids as Ala, Asn, Gln, Tyr, Trp and Phe. A preferred variant of the present invention comprises an alteration at one or more of the positions selected form the group consisting of position number 49, 87, 118, 129, 134, 142, 156, 169 and 197. In a preferred embodiment the alterations are substitutions at one or more of the positions selected form the group consisting of position number 87, 118, 129, 134, 142, 156, and 169. In a preferred embodiment the substitution is selected from the group consisting of: K87A; K129A,S,F,I; K118A; K142A,Q, R156Y,F,V,I,K,W,L,M and K169Q,A.

In one aspect, a variant of a parent xyloglucanase comprises an alteration at one or more (several) positions corresponding to positions 68 or 123 or 156 or 118 or 200 or 129 or 137 or 193 or 92 or 76 or 331. Preferably, the variant comprises substitution at position 68 and one or more substitutions at one or more additional positions, selected from the group consisting of position number 123, 156, 118, 200, 129, 137, 193, 92, 83, 149, 34, 340, 332, 9, 76, 331, 310, 324, 498, 395 and 366.

In another aspect, a variant comprises a substitution at position 156 and one or more substitutions at one or more additional positions selected from the group consisting of position number 10, 13, 14, 19, 37, 68, 78, 92, 118, 123, 129, 137, 139, 140, 147, 159, 164, 165, 169, 176, 177, 179, 183, 200, 204, 211, 222, 224, 244, 247, 249, 259, 267, 268, 269, 275, 288, 299, 301, 302, 303, 310, 324, 328, 331, 366, 380, 383, 384, 389, 406, 409, 415, 436, 443, 445, 449, 450, 454, 455, 456, 461, 470 and 507.

In another aspect, a variant of a parent xyloglucanase comprises alterations at two or more (several) positions corresponding to positions 68 or 123 or 156 or 118 or 200 or 129 or 137 or 193 or 92 or 76 or 331. Preferably, the variant comprises a substitution at position 68 or 123 or 156 or 118 or 200 or 129. Even more preferably the variant comprises a substitution at position 129 and position 156.

In another aspect, a variant of a parent xyloglucanase comprises alterations at three or more (several) positions corresponding to positions 68 or 123 or 156 or 118 or 200 or 129 or 137 or 193 or 92 or 76 or 331.

In another aspect, a variant of a parent xyloglucanase comprises alterations at four or more (several) positions corresponding to positions 68 or 123 or 156 or 118 or 200 or 129 or 137 or 193 or 92 or 76 or 331.

In another aspect, a variant of a parent xyloglucanase comprises alterations at five or more (several) positions corresponding to positions 68 or 123 or 156 or 118 or 200 or 129 or 137 or 193 or 92 or 76 or 331.

In another aspect, a variant of a parent xyloglucanase comprises alterations at six or more (several) positions corresponding to positions 68 or 123 or 156 or 118 or 200 or 129 or 137 or 193 or 92 or 76 or 331.

In another aspect, a variant of a parent xyloglucanase comprises alterations at seven or more (several) positions corresponding to positions 68 or 123 or 156 or 118 or 200 or 129 or 137 or 193 or 92 or 76 or 331.

In another aspect, a variant of a parent xyloglucanase comprises alterations at the positions corresponding to positions 129 and 156 and 331 and 200 and 118.

In another aspect, a variant of a parent xyloglucanase comprises alterations at the positions corresponding to positions 68 and 129 and 156 and 331 and 200 and 118.

In another aspect, a variant of a parent xyloglucanase comprises alterations at the positions corresponding to positions 68 and 92 and 129 and 156 and 331 and 200 and 118.

In another aspect the variant comprises one or more (several) substitutions selected from the group consisting of: Q68H,N,L; S123P,T; R156Y,F,V,I,K,W,L,M; K118A,R; G200P,E,S,D; K129T,A,S; Q137E; H193T,S,D; T92V,I,A,S; A83E; Q149E; L34F,I,V; R340T,N; S332P; T9D; S76W,V,I, K,R,T; N331F,C; M3101,V,L; D324N; G498A,D; D395G and D366H. Preferably, the substitutions are selected from the group consisting of Q68H; S123P; R156Y,F; K118A; G200P,E; K129T,A; Q137E; H193T; T92V and N331F. More preferably, the substitutions are selected from the group consisting of Q68H; S123P; R156Y,F; K118A; G200P,E; K129T, A; Q137E; T92V and N331F. More preferably, the variant contains a substitution in nine or eight, seven or six or five or four or three or two or one position(s), where the substitutions are selected from the group consisting of Q68H; S123P; R156Y,F; K118A; G200P,E; K129T,A; Q137E; T92V and N331F.

In a further aspect the variant comprises one or more (several) of the following combinations of substitutions:
Q68H;
S123P;
R156Y;
Q68H+R156Y;
K129A+R156Y;
S123T+K129A+R156Y;
K129A+R156Y+G200P;
Q68H+K118R+R156F;
Q68H+R156Y+H193T;
Q68H+R156F+G200P+N331F;
Q68H+T92V+K118A+R156Y;
K118A+K129A+R156Y+G200P+N331F;
G78A+T92V+K118A+K129A+R156Y;
Q68H+K129T+R156K+G200P+N331F;
K118A+K129A+R156Y+K169A+G200P+N331F;
T92V+K118A+K129A+R156Y+G200P+N331F;
G78A+K118A+K129A+R156Y+G200P+N331F;
G78A+T92V+K118A+K129A+R156Y+K169A;
Q68H+T92V+Q137E+R156Y+G200P+N331F;
Q68H+T92V+K118A+Q137E+R156Y+N331F;
Q68H+T92V+R156Y+G200P+M310V+N331F;
Q68H+K118A+K129A+R156Y+G200P+N331F;
Q68H+T92V+K118A+K129A+R156Y+G200P+N331F;
Q68H+T92V+K118A+Q137E+R156Y+G200P+N331F;
Q68H+T92V+K118A+K129A+R156Y+H193T+D366H;
Q68H+T92V+K118A+K129A+Q137E+R156Y+H193T+D366H;
Q68H+T92V+K118A+K129A+Q137E+R156Y+G200P+N331F;
Q68H+T92V+K118A+S123P,T+K129A+Q137E+R156Y+G200P+N331F; or
Q68H+T92V+K118A+K129A+Q137E+R156Y+G200P+A224P+N331F;

In a preferred embodiment all the variants described in the above are variants of a parent xyloglucanase which belong to family 44 of glycosyl hydrolases, more preferred the parent xyloglucanase is selected from a xyloglucanase having at least 65%, more preferably at least 70%, more preferably at least 75%, more preferably at least 80%, more preferably at least 85%, even more preferably at least 90%, most preferably at least 95% identity to the amino acid sequence of SEQ ID NO: 3, more preferred the parent xyloglucanase is selected from the group consisting of SEQ ID NO: 2, SEQ ID NO: 3, SEQ ID NO: 5 and SEQ ID NO: 7 and most preferred the parent xyloglucanases consists of SEQ ID NO: 3.

Polynucleotides

The present invention also relates to isolated polynucleotides that encode variants of a parent xyloglucanase according to the present invention. In particular polynucleotides that encode a xyloglucanase variant as described in the variant section above, is encompassed by the present invention. Polynucleotides of the invention will hybridize to a denatured double-stranded DNA probe comprising either the full variant sequence corresponding to positions 82-1653 of SEQ ID NO: 1 or position 97 to 1653 of SEQ ID NO: 1 with proper sequence alterations corresponding to actual amino acid alterations in the variant or any probe comprising a variant subsequence thereof having a length of at least about 100 base pairs under at least medium stringency conditions, but preferably at high stringency conditions. The variant polynucleotides of the present invention may also comprise silent mutations in addition to the mutations giving rise to the amino acid alterations described in the variant section above. Silent mutations are mutations in the three letter code which does not give rise to a change in the amino acid, e.g. GTT to GAT which both code for valine.

The polynucleotides encoding the xyloglucanase variants of the present invention include DNA and RNA. Methods for isolating DNA and RNA are well known in the art. DNA and RNA encoding genes of interest can be cloned in Gene Banks or DNA libraries by means of methods known in the art. Polynucleotides encoding polypeptides having xyloglucanase activity of the invention are then identified and isolated by, for example, hybridization or PCR.

Expression Vectors

The present invention also relates to expression vectors, in particular recombinant expression vectors, comprising a nucleic acid construct of the invention. Nucleic acid constructs of the invention comprise an isolated polynucleotide encoding a variant xyloglucanase of the present invention, preferably operably linked to one or more control sequences which direct the expression of the coding sequence in a suitable host cell under conditions compatible with the control sequences. In creating the expression vector, the coding sequence is located in the vector so that the coding sequence is operably linked with the appropriate control sequences for expression. The control sequences may either be provided by the vector or by the nucleic acid construct inserted into the vector.

The control sequence may be an appropriate promoter sequence, a nucleotide sequence which is recognized by a host cell for expression of a polynucleotide encoding a polypeptide of the present invention. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell. Such promoters are well known in the art. The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention, such terminators are well known in the art. The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention, such leader sequences are well known in the art. The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention. The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention. It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound.

An isolated polynucleotide encoding a variant xyloglucanase of the present invention may be manipulated in a variety of ways to provide for expression of the polypeptide. Manipulation of the polynucleotide sequence prior to insertion into a vector may be desirable or necessary depending on the expression vector. The techniques for modifying polynucleotide sequences utilizing recombinant DNA methods are well known in the art. Furthermore, tags which may aid purification or immobilization of the polypeptide may be added to the polypeptide. Such a tag may for example be a polyhistidine tag (His tag). Preferably, the tag located in the N-terminal or C-terminal of the polypeptide, and may be encoded by the vector. Alternatively, the tag may be located internally in the polypeptide, as long as it does not affect the functionality of the polypeptide.

The recombinant expression vector may be any vector (e.g., a plasmid, phagemid, phage or virus) that can be conveniently subjected to recombinant DNA procedures and can bring about the expression of the nucleotide sequence. The choice of the vector will typically depend on the compatibility of the vector with the host cell into which the vector is to be introduced.

The vectors may be linear or closed circular plasmids. The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers that permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers that confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention may contain an element(s) that permits stable integration of the vector into the host cell's genome or autonomous replication of the vector in the cell independent of the genome.

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

In one embodiment of the present invention the plasmid vector may contain the following elements:
i) a signal peptide coding region (e.g. obtained from the genes for *Bacillus* NCIB 11837 maltogenic amylase, *Bacillus stearothermophilus* alpha-amylase, *Bacillus licheniformis* subtilisin, *Bacillus licheniformis* alpha-amylase, *Bacillus stearothermophilus* neutral proteases (nprT, nprS, nprM), and *Bacillus subtilis* prsA), followed by a polynucleotide sequence encoding the mature xyloglucanase variant. This sequence may be preceded by and operably linked to:
ii) a DNA sequence comprising a mRNA stabilising segment (e.g. derived from the CryIIIa gene, as shown in WO 99/043835);
iii) a marker gene (e.g. a chloramphenicol resistance gene); and
iv) genomic DNA from *Bacillus subtilis* as 5' and 3' flanking segments upstream and downstream of the polynucleotide, respectively, to enable genomic integration by homologous recombination between the flanking segments and the *Bacillus* genome.

The vectors describe above may also be useful in the generation and screening of the variants using the previously described mutagenesis procedures Host Cells The present invention also relates to recombinant a host cell comprising a polynucleotide encoding a variant xyloglucanase of the invention, which are advantageously used in the recombinant production of the polypeptides. A vector comprising a polynucleotide sequence of the present invention is introduced into a host cell so that the vector is maintained as a chromosomal integrant or as a self-replicating extra-chromosomal vector as described earlier.

The host cell may be a prokaryote such as bacterial cells, an archaea or an eukaryote such as fungal cells, plant cells, insect cells, or mammalian cells.

Useful prokaryotes are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus halodurans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus*, *Bacillus licheniformis*, *Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., In, *Ainsworth and Bisby's Dictionary of The Fungi*, 8th edition, 1995, CAB International, University Press, Cambridge, UK, page 171) and all mitosporic fungi (Hawksworth et al., In, *Ainsworth and Bisby's Dictionary of The Fungi*, 8th edition, 1995, CAB International, University Press, Cambridge, UK). In a more preferred embodiment, the fungal host cell is a yeast cell. "Yeast as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, eds, *Soc. App. Bacteriol. Symposium Series* No. 9, 1980).

In an even more preferred embodiment, the yeast host cell is a *Candida*, *Hansenula*, *Kluyveromyces*, *Pichia*, *Saccharomyces*, *Schizosaccharomyces*, or *Yarrowia* cell. In a most preferred embodiment, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi include all filamentous forms of the subdivision Eumycota and Oomycota (as defined by Hawksworth et al., In, *Ainsworth and Bisby's Dictionary of The Fungi*, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium*, or *Trichoderma*. In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson and Simon, editors, Guide to Yeast Genetics and Molecular Biology, *Methods in Enzymology* 194: 182-187, Academic Press, Inc., New York; Ito et al., 1983, Journal of Bacteriology 153: 163; and Hinnen et al., 1978, *Proceedings of the National Academy of Sciences USA* 75: 1920.

A particular embodiment of the present invention is a recombinant host cell transformed with a polynucleotide encoding a variant xyloglucanase of the present invention. Preferably, such a host cell does not contain an inherent xyloglucanase encoding gene, or such a gene has been disrupted. Thereby the recombinant variant xyloglucanases is the only xyloglucanase produced by the recombinant host cell of the present invention.

Methods of Production

The present invention also relates to methods of producing a xyloglucanase variant, comprising: (a) cultivating a host cell of the present invention under conditions suitable for the expression of the variant; and (b) recovering the variant from the cultivation medium.

In the production methods of the present invention, the host cells are cultivated in a nutrient medium suitable for production of the xyloglucanase variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

One embodiment of the present invention is a method of producing a variant of a parent xyloglucanase, wherein said variant has xyloglucanase activity, said method comprising: a) culturing a cell under conditions suitable for expression of the variant, where said cell contains a polynucleotide sequence encoding a variant of a parent xyloglucanase in which said variant is altered in one or more (several) amino acid position(s) selected from the group consisting of positions: 68, 123, 156, 118, 200, 129, 137, 193, 92, 83, 149, 34, 340, 332, 9, 76, 331, 310, 324, 498, 395, 366, 1, 374, 7, 140, 8, 14, 21, 211, 37, 45, 13, 78, 87, 436, 101, 104, 111, 306, 117, 119, 414, 139, 268, 142, 159, 164, 102, 168, 176, 180, 482, 183, 202, 206, 217, 4, 222, 19, 224, 228, 232, 2, 240, 244, 5, 247, 249, 328, 252, 259, 406, 267, 269, 275, 179, 166, 278, 281, 288, 298, 301, 18, 302, 165, 80, 303, 316, 169, 322, 120, 146, 342, 348, 147, 353, 380, 468, 382, 383, 38, 384, 389, 391, 10, 392, 396, 177, 397, 399, 409, 237, 413, 253, 415, 418, 40, 443, 445, 148, 449, 225, 450, 454, 3, 455, 456, 299, 461, 470, 204, 476, 488, 347, and 507, and said polynucleotide sequence is prepared by mutagenesis of a parent polynucleotide sequence selected from the group consisting of SEQ ID NO: 1, SEQ ID NO: 4 and SEQ ID NO: 6, or a parent polynucleotide sequence having at least 65%, more preferably at least 70%, more preferably at least 75%, more preferably at least 80%, more preferably at least 85%, even more preferably at least 90%, most preferably at least 95% identity to the nucleotide sequence of SEQ ID NO: 1; and b) recovering the xyloglucanase variant from the cultivation medium.

In an alternative aspect, the xyloglucanase variant is not recovered, but rather a host cell of the present invention expressing a variant is used as a source of the variant.

The xyloglucanase variant may be detected using methods known in the art that are specific for the expressed polypeptides. These detection methods may include use of specific antibodies, formation of an enzyme product, or disappearance of an enzyme substrate. For example, an enzyme assay may be used to determine the activity of the variant xyloglucanase as described herein in the Examples.

The resulting xyloglucanase variant may be recovered by methods known in the art. For example, the polypeptide may be recovered from the nutrient medium by conventional procedures including, but not limited to, collection, centrifugation, filtration, extraction, spray-drying, evaporation, or precipitation.

A xyloglucanase variant of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure xyloglucanase variants.

Compositions

The present invention also relates to compositions comprising a variant xyloglucanase or a polypeptide having xyloglucanase activity of the present invention. Preferably, the compositions are enriched in such a variant or polypeptide. The term "enriched" indicates that the xyloglucanase activity of the composition has been increased, e.g., with an enrichment factor of 1.1 or more. Preferably, the compositions are formulated to provide desirable characteristics such as low color, low odor and acceptable storage stability.

The composition may comprise a variant or polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The polypeptide compositions may be prepared in accordance with methods known in the art and may be in the form of a liquid or a dry formulation. For instance, the polypeptide may be formulated in the form of a granulate or a microgranulate. The variant or polypeptide to be included in the composition may be stabilized in accordance with methods known in the art. In a preferred embodiment the variant xyloglucanase is formulated in a liquid composition.

Uses

The present invention is also directed to methods for using the xyloglucanase variants.

The variant xyloglucanases are preferably incorporated into and/or used together with detergent compositions, for example in laundry detergent compositions, for example household laundry detergent compositions, especially liquid laundry detergent compositions. The detergent composition typically comprises conventional detergent ingredients such as surfactants (anionic, cationic, nonionic, zwitterionic, amphoteric), builders, bleaches, polymers, other enzymes and other ingredients, e.g. as described in WO2007/130562 and WO2007/149806, which are hereby incorporated by reference in its entirety.

The detergent composition can be in any form, such as a solid, liquid, gel or any combination thereof, preferably the composition is in a liquid form, preferably a liquid laundry detergent composition.

An aspect of the invention is the use of a xyloglucanase variant or of a xyloglucanase variant composition of the invention together with a detergent composition in order to impart de-pilling and/or fabric-softness and/or colour clarification and/or soil removal and/or soil anti-redeposition and/or dye transfer inhibition benefits to a fabric or garment.

Furthermore, the invention relates to a process for laundering of fabrics comprising treating fabrics with a washing solution containing a detergent composition and a xyloglucanase variant or a xyloglucanase variant composition of the invention. The laundering treatment can for example be carried out in a machine washing process or in a manual washing process. The washing solution can for example be an aqueous washing solution containing the detergent composition and with a pH between 3 and 12.

During washing and use, the surface of fabrics or garment will conventionally become contaminated with broken or loosed fibre fragments which can give the fabric a faded and worn appearance. Removal of these surface fibers from the fabric will partly restore the original colours and looks of the fabric, resulting in colour clarification and enhanced appearance. A xyloglucanase variant or xyloglucanase variant composition of the invention may be used to provide colour clarification and/or enhanced appearance by use in single or in multiple (repeated) washing cycles.

Furthermore, microfibrils protruding from the surface of the textile can gather into little balls, so-called pills or fluffs that stick to the surface and disturb the appearance of the fabric. A xyloglucanase variant or xyloglucanase variant composition of the invention may be used to remove such pills, an effect that is termed de-pilling.

Colour-clarification and de-pilling can be assessed by visual inspection using a test group panel. The effects may also be measured by light reflection or by determination of cotton fluffs by means of optical measurements. These methods are generally known in the art and briefly described in *Enzymes in Detergency*, 1997, published by Marcel Dekker, page 139 to page 140.

Especially with an increasing number of wash cycles, deposits, which can include particulate soils, soluble soils, dyes and pigments and insoluble salts, build up on the textile fibre surfaces. This can leads to a visible deterioration of the perceived cleaning performance of the washing treatments for example leading to a greyish or yellowish appearance of the fabric. This may be prevented using a xyloglucanase variant or xyloglucanase variant composition of the invention in the wash cycles. This effect is termed anti-redeposition or dye transfer inhibition or soil removal and may be assessed by optical measurements.

Soil or insoluble salt particles trapped on the surface of the fabric and between the fibers can lead to stiffening of the fabric. By including a xyloglucanase variant or xyloglucanase variant composition of the invention in the wash cycles the fabric may be softened.

The fabrics subjected to the methods of the present invention may be conventional washable laundry, for example household laundry. Preferably, the major part of the laundry is garments and fabrics, including knits, wovens, denims, yarns, and towelling, made from cotton, cotton blends or natural or manmade cellulosics (e.g. originating from wood pulp) or blends thereof. Examples of blends are blends of cotton or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell).

It is recognized that the treatment of fabrics and/or garments with a detergent solution containing the xyloglucanase variant or xyloglucanase variant composition of the invention can be particularly relevant in connection with, for example, production of new fibers and/or fabrics and/or garments, and also during laundering of used fabrics and/or garments for example during household laundering processes or in institutional laundering processes.

The dosage of the xyloglucanase variant or the xyloglucanase variant composition of the present invention and other conditions, under which the composition is used, including the composition and concentration of the detergent solution, may be determined on the basis of methods known in the art.

The present invention is further described by the following examples that should not be construed as limiting the scope of the invention.

The xyloglucanases can be used in the compositions of the present invention to effect removal of soils containing derivatives of cellulose or hemicellulose, enhance anti-redeposition and improve soil release. The xyloglucanases can also be used in the compositions of the present invention to impart soil release benefits to cotton during a subsequent laundering process. The soil release benefit is observed on cotton fabric and on all types of fabric that comprise a significant amount of cotton, such as cotton-synthetic (e.g. polyester, polyamide such as Nylon™, and elastane) blends.

EXAMPLES

Example 1

Production and Purification of Xyloglucanase Variants

The xyloglucanase variants of the present invention were prepared by standard procedures, in brief: Introducing random and/or site-directed mutations into the gene, transforming Bacillus subtilis host cells with the mutated genes, fermenting the transformed host cells, and obtaining the xyloglucanase variant from the fermentation broth. The reference xyloglucanase (SEQ ID NO: 3) was produced recombinantly in Bacillus subtilis in a similar manner.

Fermentation was carried out in shake flask cultures at 37° C. for 4 days shaking of 100 ml PS-1 medium containing one CaCO3 tablet (0.5 g) in a baffled 500 ml Erlenmeyer flask. The PS-1 medium composition contains 100 g/L sucrose, 40 g/L Soymeal Meal, 10 g/L $Na_2HPO_4*12H_2O$, 0.1 ml/L Dowfax 63N10 and antibiotic in the form of 6 μg/ml chloramphenicol.

After fermentation the culture broth was harvested by centrifugation (26000×g, 20 min). A small volume of the supernatant was sterile filtered through a 0.45 μm filter, and stored frozen. The samples were allowed to thaw immediately before the stability assays described below were started.

In some cases the enzyme samples were purified before they were used for the stability test.

For enzyme purification the supernatants were filtered through a NALGENE 0.2 μm Filtration unit (cat. no. 569-0020) in order to remove the rest of the host cells. The pH of the 0.2 μm filtrate was adjusted to pH 5.0 with 20% $CH_3COOH$ and the filtrate was applied to an XpressLine ProA column (UpFront chromatography A/S) equilibrated in 50 mM succinic acid/NaOH, 1 mM $CaCl_2$, pH 5.0. After washing the XpressLine ProA column extensively with the equilibration buffer, the xyloglucanase was eluted by a step-elution with 50 mM Tris/HCl, pH 9.0. Fractions were collected during elution. Fractions from the column were analysed for xyloglucanase activity (Example 2) and fractions with activity were pooled. The pH of the pool was adjusted to pH 9.0 with 3M Tris base and the pool was diluted with demineralised water to the same (or lower) conductivity as 50 mM Tris/HCl, pH 9.0. The adjusted solution was applied to a SOURCE Q column (GE Healthcare) equilibrated in 50 mM Tris/HCl, pH 9.0. After washing the SOURCE Q column extensively with the equilibration buffer, the enzyme was eluted with a linear NaCl gradient (0→0.5M) in the same buffer over five column volumes. Fractions from the column were again analysed for xyloglucanase activity and active fractions were further analysed by SDS-PAGE. Fractions, where only one band was seen on the Coomassie stained SDS-PAGE gel, were pooled as the purified preparation.

Example 2

Xyloglucanase Assay

The xyloglucanase activity of enzyme samples, e.g. from purification, were measured in an AZCL-xyloglucan assay.

AZCL-xyloglucan (Megazyme) was incubated with the xyloglucanase and the liberated blue colour was measured at 650 nm. The xyloglucanase activity was calculated as the increase in blue colour during incubation after subtraction of the proper blank value.

AZCL-xyloglucan substrate: 4 mg/ml AZCL-xyloglucan (Megazyme) homogeneously suspended in 0.01% Triton X-100 by stirring.

Assay temperature: 37° C.

Assay buffer: 50 mM succinic acid/NaOH, 0.01% Triton X-100, pH 5.0.

500 μl AZCL-xyloglucan substrate suspension was placed on ice in an Eppendorf tube. 500 μl Assay buffer was added and the mixture was allowed to become ice-cold. 20 μl enzyme sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm). The incubation was stopped by transferring the tube back to the ice bath. When the tube had become ice-cold, the tube was centrifuged shortly in an ice-cold centrifuge to precipitate unreacted substrate. 200 μl supernatant was transferred to a microtiter plate and $A_{650}$ was read. A buffer blank (20 μl 0.01% Triton X-100 instead of enzyme) was included in the assay and the difference in $A_{650}$ between enzyme sample and buffer blank was a measure of the xyloglucanase activity.

Example 3

Stability of Xyloglucanase Variants

The detergent stability of the xyloglucanase variants of the present invention was assessed by measuring the activity of the variants after incubation in a liquid detergent.

The stability test was performed by adding an enzyme sample into the liquid detergent and storing it at elevated temperatures, e.g. 35° C. or 40° C. After the prescribed storage time the enzyme activity was determined and compared with the activity of an equivalent sample stored at approximately −18° C. for the same time period. The result of the stability test is the activity found in the sample stored at elevated temperature expressed as % of the activity found in the cold stored sample.

The results for the xyloglucanase variants were compared to the result for the parental xyloglucanase (SEQ ID NO:3), tested under the same conditions. The ratio between these two stability results is the Stability Improvement Factor (SIF).

Variants having a SIF>1 are more stable under the test conditions than the parental xyloglucanase. Preferred variants are those that have high SIF in this test.

Detergent

The liquid detergent used for the stability tests has the following composition

| | |
|---|---|
| alkylethoxy sulfate | 20.1% |
| alkylbenzene sulfonate | 2.7% |
| alkyl sulfate | 6.5% |
| alkyl ethoxylate | 0.8% |
| citric acid | 3.8% |
| fatty acid | 2.0% |
| Borax | 3.0% |
| Na & Ca formate | 0.2% |
| amine ethoxylate polymers | 3.4% |
| diethylenetriaminepentaacetic acid | 0.4% |
| Tinopal AMS-GX | 0.2% |
| Ethanol | 2.6% |
| Propylene glycol | 4.6% |
| Diethylene glycol | 3.0% |
| polyethylene glycol | 0.2% |
| Monoethanolamine | 2.7% |
| NaOH | to pH 8.3 |
| Minor ingredients (protease, amylase, perfume, dye) | 2.3% |
| Water | balance |

Storage Test

The enzyme samples prepared according to Example 1 were allowed to thaw immediately before starting the storage stability test.

The enzyme samples were diluted to a concentration of approximately 0.25 mg enzyme protein per ml.

The liquid detergent was dispensed into glass bottles with a volume of approximately 12 ml, providing 1.0±0.05 gram of detergent in each glass.

For each enzyme sample two duplicate bottles were prepared. 50 μl diluted enzyme and a small magnetic stirrer bar was added to the bottles and they were closed tightly (to prevent evaporation during storage). The contents were mixed with help of the magnetic stirrer bar for about 5 minutes. One bottle of the pair was placed in a freezer at approximately −18° C. The other bottle was placed in a suitable incubator oven at the prescribed elevated temperature, e.g. 35° C. or 40° C., to be tested. After the prescribed storage time the bottles in the incubator oven are transferred into the freezer.

Activity Assay

The activity of the enzyme samples after storage in detergent was measured using the following procedure.

Materials and Reagents:

1M Phosphate Buffer pH7:

Dissolve 138 grams of $NaH_2PO_4 \cdot H_2O$ in about 750 ml water. Add 4N NaOH to give pH 7.0. Then make the final volume to 1000 ml.

Assay Buffer (50 mM Phosphate pH7):

Mix 950 ml water, 50 ml 1M phosphate buffer pH7 and 5 ml of Berol 537 (nonionic surfactant supplied by Akzo Nobel). Adjust the final pH to 7.00±0.02.

Substrate:

Cellazyme C tablets, supplied by Megazyme International Ireland Ltd, catalogue number T-CCZ. The tablets contain cross-linked dyed HE cellulose.

Procedure

About 30 minutes prior to starting the assay the bottles were transferred from the freezer into a refrigerator at approximately 4° C. Immediately before starting the assay the bottles were taken out of the refrigerator and placed on the laboratory bench top and opened.

10 ml assay buffer (room temperature) was added to each open bottle. The bottles were then transferred into a 30° C. water bath equipped with a submerged multipoint magnetic stirrer. The contents were stirred gently for about 5 minutes.

One Cellazyme C tablet was added to each bottle. Stirring was continued using a stirrer speed which is just adequate to keep the substrate particles in movement and avoid sedimentation. The bottles were removed from the water bath 30 minutes after addition of the tablet and were then allowed to stand at room temperature with no stirring for 15 minutes.

With a pipette approximately 1 ml of the practically clear supernatant from the top of each bottle was transferred into a semi-micro spectrophotometer cuvette. Absorbance at 590 nm was then measured using a suitable spectrophotometer. All measurements were finished within 15 minutes.

Blank samples, i.e. equivalent detergent samples but containing no added xyloglucanase enzyme, were included in the assay.

Calculation

For each enzyme sample there are two Abs590 measurements:

A590f, which is the Abs590 value of the sample stored at −18° C.

A590w, which is the Abs590 value of the sample stored at elevated temperature.

Subtract the blank value (A590b) from both A590f (giving A590f−A590b) and from A590w (giving A590w−A590b).

The stability was calculated as:

$$\% \text{ Stability} = ((A590w - A590b)/(A590f - A590b)) \times 100\%.$$

For each enzyme the results for (A590f−A590b) must be in the range 0.1-1.2. If the value is outside this range the result for that enzyme must be regarded as being unreliable and the test should be repeated with a different dilution of the enzyme sample.

Finally the Stability Improvement Factor (SIF) for each enzyme variant is calculated as follows:

SIF=% stability of enzyme sample/% stability of parent enzyme    (SEQ ID NO: 3)

Results

Below are the stability results of xyloglucanase variants tested under different conditions.

TABLE 1

Sterile filtered enzyme samples stored for 18 hours at 40° C.

| Mutations | SIF |
|---|---|
| K8Q | 1.1 |
| K8A | 1.2 |
| K13A | 1.1 |
| K18R | 1.1 |
| K87Q | 1.1 |
| K129A | 1.7 |
| K169Q | 1.3 |
| K169R | 1.4 |
| K169A | 1.3 |
| N140F | 1.2 |
| G316I | 1.1 |
| F418I | 1.1 |
| L34I | 1.1 |
| L166I | 1.1 |
| L268I | 1.1 |
| L278I | 1.3 |
| V1* + V2* + H3* | 1.2 |
| *0aE + *0bV | 1.3 |
| F146L | 1.2 |
| Q137E | 1.6 |
| R156Y | 2.2 |
| R156Q | 1.5 |
| K8S | 1.2 |
| K21T | 1.4 |
| K176P | 1.1 |
| K445S | 1.4 |
| K470T | 1.2 |

TABLE 2

Purified enzyme samples stored for 18 hours at 40° C.

| Mutations | SIF |
|---|---|
| K87Q | 1.1 |
| K129A | 1.8 |
| K169A | 1.1 |
| A7T + G200P + A224P + G225K + R267K + L268K + S269A | 1.3 |
| H164N + V179I + G200A + R267K | 1.2 |
| H164N + V179I + G200A + R211K + G225D + F281L | 1.5 |
| H164N + G200A + G225N + R267K | 1.2 |

TABLE 3

Sterile filtered enzyme samples stored for 24 hours at 40° C.

| Mutations | SIF |
|---|---|
| K101R + L102I | 1.1 |
| K217A | 1.1 |
| L380F | 1.1 |
| N383Y | 1.2 |
| G78A | 1.2 |
| M310V | 1.2 |
| N399I | 1.1 |
| G498S | 1.1 |
| F146L | 1.1 |
| Q137E | 1.4 |
| R156Y | 2.0 |
| V1* + V2* + H3* + G4* + Q5* | 1.1 |
| N331F | 1.2 |
| K8S | 1.1 |
| T92V | 1.3 |
| K176P | 1.2 |
| G253A | 1.1 |
| K445S | 1.3 |
| K470T | 1.2 |

TABLE 4

Purified enzyme samples stored for 24 hours at 40° C.

| Mutations | SIF |
|---|---|
| T92V | 1.2 |
| Q137E | 1.5 |
| R156Y | 1.7 |
| R156Q | 1.2 |

TABLE 5

Sterile filtered enzyme samples stored for 30 hours at 40° C.

| Mutations | SIF |
|---|---|
| K118R | 1.1 |
| K118A | 1.7 |
| K129A + K169A | 1.6 |
| G200P | 1.5 |
| K129A + R156Y | 2.0 |
| K129A + Q137E + R156Y | 2.2 |
| K129A + R156Y + H164N | 2.1 |

TABLE 6

Purified enzyme samples stored for 30 hours at 40° C.

| Mutations | SIF |
|---|---|
| T92V | 1.3 |
| R156Y | 1.9 |
| K129A + R156Y | 2.1 |

TABLE 7

Sterile filtered enzyme samples stored for 48 hours at 40° C.

| Mutations | SIF |
|---|---|
| K118A | 3.0 |
| K252Q | 1.1 |
| K252R | 1.2 |
| K252A | 1.1 |
| K275Q | 1.1 |
| K275R | 1.2 |
| K275A | 1.1 |
| K306R | 1.1 |
| K306A | 1.1 |
| K347Q | 1.1 |
| K347R | 1.1 |
| K347A | 1.1 |
| K382A | 1.1 |
| K414A | 1.2 |
| K445R | 1.3 |
| K454R | 1.1 |
| K476Q | 1.1 |
| K482Q | 1.1 |
| K482A | 1.1 |
| K488Q | 1.1 |
| K488R | 1.1 |
| K488A | 1.1 |
| M40V | 1.4 |
| R156Y | 2.9 |
| G200P | 1.8 |
| K129A + R156Y | 3.5 |
| K129A + Q137E + R156Y + K470T | 3.7 |
| K406N | 1.1 |
| K445S | 1.2 |
| K488T | 1.2 |
| T92V + K129A + R156Y | 3.7 |
| K118A + K129A + R156Y | 3.8 |
| T92V + K118A + K129A + R156Y | 3.9 |
| K129A + R156Y + P507A | 3.2 |
| K129A + R156Y + S443D + K445S + L449I + V450I + S455N + M456Y | 3.8 |
| K129A + R156Y + H436Y | 3.9 |
| K129A + R156Y + K406N + N415G | 3.5 |
| K129A + R156Y + L380F + N383Y + D384G + N389T | 3.5 |
| K129A + R156Y + D366H + T374A | 3.4 |
| K129A + R156Y + A328G | 3.5 |
| K129A + R156Y + V259I + R267K + L268K + S269A | 3.5 |
| K129A + R156Y + T244D | 3.4 |
| K129A + R156Y + I222V + A224P + V228I + V232A | 2.0 |
| K129A + R156Y + G200P + G204T + R211K | 3.6 |
| K129A + R156Y + A177T + V179I + A183S | 2.9 |
| K129A + R156Y + V159M + H164N + F165Y | 2.8 |
| K129A + R156Y + I10V + V14I + D19E | 4.0 |
| T104A + P111Q + A117S + K129A + R156Y | 2.1 |
| S123T + K129A + R156Y | 3.8 |
| K129A + Q137E + V139K + N140F + Q147S + R156Y | 2.9 |
| K129A + R156Y + D324N | 3.4 |
| K129A + R156Y + K176P | 3.2 |
| K129A + R156Y + D249N | 3.2 |
| K129A + R156Y + D249G | 3.3 |
| K129A + R156Y + D249S | 3.1 |
| K129A + R156Y + D461N | 3.6 |
| K129A + R156Y + D461T | 3.9 |
| K129A + R156Y + D461Q | 4.0 |
| K129A + R156Y + R409T | 3.8 |
| K129A + R156Y + R409L | 3.6 |
| K129A + R156Y + D247G | 1.4 |
| K129A + R156Y + E288Q | 2.7 |
| D37G + K129A + R156Y | 3.9 |
| D37N + K129A + R156Y | 3.6 |
| K129A + R156Y + R267H | 3.8 |
| K129A + R156Y + D303I | 4.1 |
| K129A + R156Y + D303K | 3.7 |
| K129A + R156Y + K275T | 3.5 |
| K129A + R156Y + G200P | 3.9 |
| K129A + R156Y + N331F | 3.8 |
| R156Y + N331F | 3.2 |
| K118A + K129A + R156Y + K470T | 4.4 |
| K470R | 1.1 |
| K470P | 1.2 |
| G413A | 1.1 |

TABLE 7-continued

Sterile filtered enzyme samples stored for 48 hours at 40° C.

| Mutations | SIF |
|---|---|
| K118A + K129A + R156Y + A224P | 3.9 |
| D119L | 1.3 |
| K87V + K129A + K169A | 1.9 |
| K129A + K445S | 1.8 |
| K118A + K129A + R156Y + G200P | 3.8 |
| K118A + K129A + R156Y + G200P + N331F | 4.2 |
| G78A + K118A + K129A + R156Y | 3.8 |
| G78A + T92V + K118A + K129A + R156Y | 3.8 |
| T92V + K118A + K129A + R156Y | 3.7 |
| M310V + N399I | 1.7 |
| L34I + K129A | 1.9 |
| K101A + K129A | 1.8 |
| K13A + K129A | 2.0 |
| K129A + K470T | 1.8 |
| K129A + K176P | 1.9 |
| G78A + T92V + K118A + K129A + R156Y + K169A | 4.8 |
| K118A + K129A + R156Y + K169A + G200P + N331F | 4.7 |
| K118A + K129A + R156Y + G200P + M310V + N331F | 4.7 |
| K129A + R156Y + K454Q | 3.8 |
| G78A + K118A + K129A + R156Y + G200P + N331F | 4.2 |
| T92V + K118A + K129A + R156Y + G200P + N331F | 4.3 |
| K129A + R156Y + N302K + D303S | 2.9 |
| K129A + R156Y + N302K + D303L | 2.7 |
| S332P + V397I | 1.1 |
| K129A + R156Y + K322I + K454Q | 2.3 |
| Q68H + K118A + K129A + R156Y + G200P + N331F | 4.1 |
| Q68H + T92S + K118A + K129A + R156Y + G200P + N331F | 5.2 |
| Q68H + T92A + K118A + K129A + R156Y + G200P + N331F | 4.7 |
| Q68H + K118A + K129A + R156Y + G200P + N331F | 5.0 |
| Q68H + K118A + K129A + R156Y + G200P + N331F | 5.7 |
| Q68H + T92D + K118A + K129A + R156Y + G200P + N331F | 3.3 |
| Q68H + T92I + K118A + K129A + R156Y + G200P + N331F | 4.4 |
| Q68H + K118A + K129A + R156Y + G200P + N331F | 4.4 |
| Q68H + T92V + K118A + K129A + R156Y + G200P + N331F | 4.2 |
| K129S | 1.1 |
| K129A | 1.5 |
| R156M | 1.3 |
| R156F | 2.3 |
| R156W | 1.6 |
| R156L | 1.4 |
| R156V | 2.2 |
| G396P | 1.3 |
| G413S | 1.1 |
| A177T | 1.1 |
| E38I | 1.1 |
| E38V | 1.2 |
| G36V + D37A + E38* + N39* | 1.2 |
| T104A | 1.2 |
| L102A + T104V + *104P | 1.3 |
| Q68L | 1.3 |
| Q68H | 3.6 |
| N389A | 1.1 |
| G468Y | 1.1 |
| G237V | 1.1 |

TABLE 8

Purified enzyme samples stored for 48 hours at 40° C.

| Mutations | SIF |
|---|---|
| K118A | 2.3 |
| R156Y | 2.5 |
| K129A + K169A | 1.7 |
| G200P | 1.5 |
| K129A + R156Y | 1.7 |
| K129A + Q137E + R156Y | 3.7 |
| K129A + R156Y + H164N | 3.5 |
| K129A + Q137E + R156Y + K470T | 4.2 |
| T92V + K129A + R156Y | 4.5 |
| K118A + K129A + R156Y | 3.8 |
| K129A + R156Y + G200P | 4.8 |
| K129A + R156Y + N331F | 4.1 |

TABLE 8-continued

Purified enzyme samples stored for 48 hours at 40° C.

| Mutations | SIF |
|---|---|
| R156Y + N331F | 3.5 |
| K118A + K129A + R156Y + G200P, | 4.2 |
| K118A + K129A + R156Y + G200P + N331F | 4.5 |
| G78A + K118A, + K129A + R156Y | 4.0 |
| G78A + T92V + K118A + K129A + R156Y | 4.3 |
| Q68H | 3.7 |

TABLE 9

Sterile filtered enzyme samples stored for 72 hours at 40° C.

| Mutations | SIF |
|---|---|
| K13R | 1.3 |
| K206Q | 1.1 |
| K129A + R156Y | 5.1 |
| K129A + Q137E + R156Y + K470T | 6.4 |
| T92V + K129A + R156Y | 6.6 |
| K118A + K129A + R156Y | 7.2 |
| K129A + R156Y + G200P | 7.7 |
| K129A + R156Y + N331F | 5.9 |
| R156Y + N331F | 5.3 |

TABLE 10

Sterile filtered enzyme samples stored for one week at 35° C.

| Mutations | SIF |
|---|---|
| K8Q | 1.4 |
| K8A | 1.1 |
| K13Q | 1.1 |
| K18Q | 1.1 |
| K18A | 1.4 |
| K21Q | 1.4 |
| K21R | 1.4 |
| K21A | 1.4 |
| K87Q | 1.3 |
| K101R | 1.3 |
| K101A | 1.6 |
| K118R | 1.4 |
| K118A | 2.3 |
| K101R + L102I | 1.1 |
| K129A | 2.1 |
| K169Q | 1.4 |
| K169R | 1.5 |
| K169A | 1.5 |
| K220Q | 1.3 |
| K220A | 1.2 |
| K252Q | 1.1 |
| K252R | 1.1 |
| K275Q | 1.1 |
| K275R | 1.1 |
| K275A | 1.1 |
| K306R | 1.1 |
| K306A | 1.1 |
| K307Q | 1.2 |
| K307R | 1.1 |
| K454Q | 1.6 |
| K454R | 1.2 |
| K476Q | 1.3 |
| K476R | 1.3 |
| K476A | 1.2 |
| K482Q | 1.2 |
| K482A | 1.2 |
| K488Q | 1.2 |
| K488R | 1.2 |
| K488A | 1.1 |
| N140F | 1.7 |
| G78A | 1.2 |
| M310V | 1.3 |

TABLE 10-continued

Sterile filtered enzyme samples stored for one week at 35° C.

| Mutations | SIF |
|---|---|
| G316I | 1.1 |
| W391V | 1.1 |
| N399I | 1.4 |
| L34I | 1.3 |
| L268I | 1.1 |
| L278I | 1.2 |
| G498S | 1.2 |
| *0aE + *0bV | 1.4 |
| F146L | 2.3 |
| Q137E | 2.0 |
| R156Y | 3.2 |
| R156Q | 1.7 |
| N331F | 1.5 |
| K8S | 1.3 |
| K21T | 1.5 |
| K176P | 1.2 |
| G253A | 1.1 |
| K445S | 1.5 |
| K470T | 1.6 |
| F146C | 1.3 |
| K129A + K169A | 1.8 |
| G200P | 1.7 |
| A224P | 1.1 |
| K129A + R156Y | 2.6 |
| K129A + Q137E + R156Y | 2.6 |
| K129A + R156Y + H164N | 2.6 |
| K406N | 1.3 |
| K445S | 1.2 |
| K488T | 1.2 |
| K129R | 1.1 |
| R156F | 2.0 |

TABLE 11

Purified enzyme samples stored for one week at 35° C.

| Mutations | SIF |
|---|---|
| K101R | 1.1 |
| K101A | 1.1 |
| K118A | 2.3 |
| K129A | 1.8 |
| K169R | 1.2 |
| K169A | 1.1 |
| T92V | 2.0 |
| F418I | 1.1 |
| V1* + V2* + H3* + G4* + Q5*; | 1.2 |
| Q137E | 1.6 |
| R156Y | 2.5 |
| R156Q | 1.2 |
| K21T | 1.1 |
| G200P | 1.7 |
| K129A + R156Y | 2.7 |
| K129A + Q137E + R156Y | 3.0 |
| K129A + R156Y + H164N | 3.1 |
| A7T + G200P + A224P + G225K + R267K + L268K + S269A | 1.3 |
| H164N + V179I + G200A + R267K | 1.3 |
| H164N + V179I + G200A + R211K + G225D + F281L | 1.8 |
| H164N + G200A + G225N + R267K | 1.6 |

TABLE 12

Purified enzyme samples stored for 16 hours at 44° C.

| Mutation | SIF |
|---|---|
| Q68H | 5.8 |
| S123P | 4.4 |
| R156Y | 4.0 |
| K118A | 2.9 |
| G200P | 2.6 |

TABLE 12-continued

Purified enzyme samples stored for 16 hours at 44° C.

| Mutation | SIF |
|---|---|
| K129A | 2.4 |
| Q137E | 2.4 |
| H193T | 2.1 |
| T92V | 2.0 |
| S76W | 1.7 |

Example 4

Stability of Xyloglucanase Variants

The detergent stability of the xyloglucanase variants of the present example was assessed by measuring the activity of the variants after incubation in a liquid detergent.

The stability test was performed by adding an enzyme sample into the liquid detergent and storing it at elevated temperatures, e.g. 35° C. or 46° C. After the prescribed storage time the enzyme activity was determined and compared with the activity of an identical sample that had been stored cold at approximately +5° C. for the same time period. The result of the stability test is the activity found in the sample stored at elevated temperature (the stressed sample) expressed as % of the activity found in the equivalent cold-stored sample (the unstressed sample).

The results for the xyloglucanase variants were compared to the result for the parental xyloglucanase (SEQ ID NO:3), tested under the same conditions.

Detergent

The liquid detergent used for the stability tests has the following composition

| | |
|---|---|
| alkylethoxy sulfate | 20.1% |
| alkylbenzene sulfonate | 2.7% |
| alkyl sulfate | 6.5% |
| alkyl ethoxylate | 0.8% |
| citric acid | 3.8% |
| fatty acid | 2.0% |
| Borax | 3.0% |
| Na & Ca formate | 0.2% |
| amine ethoxylate polymers | 3.4% |
| diethylenetriaminepentaacetic acid | 0.4% |
| Tinopal AMS-GX | 0.2% |
| Ethanol | 2.6% |
| Propylene glycol | 4.6% |
| Diethylene glycol | 3.0% |
| polyethylene glycol | 0.2% |
| Monoethanolamine | 2.7% |
| NaOH | to pH 8.3 |
| Minor ingredients (protease, amylase, perfume, dye) | 2.3% |
| Water | balance |

Storage Test

The enzyme samples prepared according to Example 1 were allowed to thaw immediately before starting the storage stability test.

The enzyme samples were used without further dilution.

The liquid detergent was dispensed into a round-bottom polystyrene 96-well microtiter plate (Plate 1) providing 190 µl of detergent per well.

Ten µl enzyme sample and a small magnetic stirrer bar was added to each well and the plate was closed tightly (to prevent evaporation) using adhesive aluminium foil lids (Beckman Coulter). The contents were mixed with the magnetic stirrer bars for about 30 minutes.

From each well of Plate 1, 20 μl detergent-enzyme mixture was then transferred into a new empty identical plate (Plate 2). Both plates were then sealed.

The original plate (Plate 1) was placed in an incubator oven at the prescribed elevated temperature, e.g. 35° C. or 46° C., to be tested. The other plate (Plate 2) was placed in a refrigerator at approximately 5° C.

Following incubation for the prescribed period, the plates were removed from the refrigerator and the incubator oven. The plates were placed on the laboratory bench for at least half an hour to allow all wells to reach room-temperature.

Then 20 μl from each well of Plate 1 was transferred into a new empty round bottom 96-well plate (Plate 1a).

Plate 1a now contains 20 μl stressed samples and Plate 2 contains 20 μl unstressed samples.

Activity Assay

The activity of the enzyme samples after storage in detergent was measured using the following procedure at room temperature.

Assay Principle:

Para-nitrophenol-beta-D-cellotetraoside (pNP-beta-D-cellotetraoside) is a synthetic substrate that is hydrolysed by the catalytic action of certain xyloglucanase enzymes.

The substrate itself is colourless; however upon hydrolysis of the terminal reducing end glycoside bond, para-nitrophenol is released which is yellow in a pH8 buffer due to a strong absorbance at 405 nm.

pNP-beta-D-cellotetraoside itself is very stable under the given assay conditions. Thus increasing absorbance at 405 nm is an attribute of enzymatic activity.

We found that the parental xyloglucanase (SEQ ID NO:3) accepted pNP-beta-D-cellotetraoside as substrate, as evidenced by the strong absorbance increase at 405 nm.

Materials and Reagents:

Assay Buffer: 100 mM EPPS; 0.01% Tween 20; pH 8.0.

pNP-beta-D-cellotetraoside (CAS-#: 129411-62-7; Toronto Research Chemicals; Canada)

Substrate solution: 1 mM pNP-beta-D-cellotetraoside in assay buffer.

Procedure:

Plate 1a contains 20 μl stressed samples and Plate 2 contains 20 μl unstressed samples.

The samples were diluted by adding 50 μl assay buffer to all wells in Plate 1a and Plate 2, and mixed for one hour using a microtiter plate shaker. Then an additional 50 μl assay buffer was added to all wells and the shaking was continued for an additional 10 minutes.

20 μl of the factor 6 diluted samples were transferred to a transparent 384 well polystyrene microtiter plate, and 20 μl substrate solution was added to all wells. The samples were mixed by shaking the microtiter plate briefly. The kinetic measurement of enzymatic activity was initiated immediately by observing the rate of increasing absorbance at 405 nm using a 384-well spectrophotometric reader.

The initial velocity (Abs/min) of the reaction was determined. The initial velocity of the reaction was a measure of the enzymatic activity in the sample as verified by a linear standard curve within relevant enzyme concentrations.

Calculation:

% residual activity was calculated as enzymatic activity in the stressed sample divided by enzymatic activity in the identical unstressed sample.

% residual activity="Abs/min (stressed sample)"/ "Abs/min (not stressed sample)"*100%.

Results

Below are the stability results of xyloglucanase variants tested under different conditions.

TABLE 13

Sterile filtered enzyme samples stored for 16 hours at +44° C.

| Mutations | % Residual Activity |
| --- | --- |
| SEQ ID NO: 3 | 7 |
| K118A | 24 |
| R156Y | 36 |
| K129A + K169A | 19 |
| G200P | 26 |
| K129A + R156Y | 51 |
| K129A + Q137E + R156Y | 72 |
| K129A + R156Y + H164N | 63 |

TABLE 14

Sterile filtered enzyme samples stored for 16 hours at +47° C.

| Mutations | % Residual Activity |
| --- | --- |
| SEQ ID NO: 3 | <5 |
| Q68H + T92S + K118A + K129A + R156Y + G200P + N331F | 77 |
| Q68H + T92A + K118A + K129A + R156Y + G200P + N331F | 83 |
| Q68H + K118A + K129A + R156Y + G200P + N331F | 91 |
| Q68H + T92D + K118A + K129A + R156Y + G200P + N331F | 49 |
| Q68H + T92Y + K118A + K129A + R156Y + G200P + N331F | 78 |
| Q68H + T92I + K118A + K129A + R156Y + G200P + N331F | 89 |
| Q68H + T92V + K118A + K129A + R156Y + G200P + N331F | 95 |
| Q68H + T92S + K118A + K129A + R156Y + G200P + G274D + N331F | 67 |
| Q68H + T92N + D97N + K118A + K129A + R156Y + G200P + N331F | 81 |
| Q68H | 52 |
| K118A + K129A + R156Y | 52 |
| T92V + K118A + K129A + R156Y | 88 |
| K129A + R156Y + G200P + G204T + R211K | 68 |
| S123T + K129A + R156Y | 65 |
| K129A + R156Y + G200P | 73 |
| K118A + K129A + R156Y + G200P + N331F | 90 |
| G78A + K118A + K129A + R156Y + G200P + N331F | 98 |
| T92V + K118A + K129A + R156Y + G200P + N331F | 95 |

TABLE 15

Sterile filtered enzyme samples stored for 16 hours at +44° C.

| Mutations | % Residual Activity |
|---|---|
| SEQ ID NO: 3 | 22 |
| R156Y | 59 |
| K13R | 34 |
| K307Q | 31 |
| K414A | 34 |
| G253A | 33 |
| G498S | 31 |
| M310V | 38 |
| N399I | 30 |
| V1* + V2* + H3* + G4* + Q5* | 31 |
| F146L | 34 |
| K445S | 30 |
| K470T | 30 |

TABLE 16

Sterile filtered enzyme samples stored for 16 hours at +45° C.

| Mutations | % Residual Activity |
|---|---|
| SEQ ID NO: 3 | 6 |
| R156Y | 34 |
| K129A + R156Y | 55 |
| K101R + L102I | 12 |
| K118A + K129A + R156Y | 72 |
| K129A + R156Y + P507A | 57 |
| K129A + R156Y + D366H + T374A | 44 |
| K129A + R156Y + V259I + R267K + L268K + S269A | 40 |
| K129A + R156Y + G200P + G204T + R211K | 49 |
| K129A + R156Y + V159M + H164N + F165Y | 30 |
| T104A + P111Q + A117S + K129A + R156Y | 39 |
| S123T + K129A + R156Y | 70 |
| K129A + R156Y + D324N | 60 |
| K129A + R156Y + D461N | 59 |
| K129A + R156Y + D461T | 61 |
| K129A + R156Y + D461Q | 59 |
| D37G + K129A + R156Y | 60 |
| D37N + K129A + R156Y | 64 |
| K129A + R156Y + R267H | 64 |
| K129A + R156Y + D303I | 62 |
| K129A + R156Y + D303K | 65 |
| K129A + R156Y + K275T | 68 |
| K129A + R156Y + G200P | 92 |
| K118A + K129A + R156Y + K470T | 80 |
| H164N | <5 |
| K129A + R156Y + N302K + D303S | 66 |
| K129A + R156Y + N302K + D303L | 64 |

TABLE 17

Sterile filtered enzyme samples stored for 16 hours at +44° C.

| Mutations | % Residual Activity |
|---|---|
| SEQ ID NO: 3 | 26 |
| R156Y | 58 |
| K118A + R156Y + G200P | 84 |
| K118A + K129A + Q137E + R156Y + G200P + N331F | 92 |
| K445C + K470C | 32 |
| F281L | 32 |
| D366H | 35 |
| K392G | 26 |
| D395G | 35 |
| S76W | 47 |
| G498D | 32 |
| G498A | 36 |
| D324N | 39 |
| S123T | 36 |
| Q68Y | 6 |
| Q68C | 13 |
| K129A + R156Y | 89 |
| K118A + K129A + R156Y + G200P + N331F | 100 |

TABLE 18

Sterile filtered enzyme samples stored for 16 hours at +44° C.

| Mutations | % Residual Activity |
|---|---|
| SEQ ID NO: 3 | 34 |
| R156Y | 66 |
| R156M | 39 |
| R156F | 63 |
| R156W | 44 |
| R156L | 34 |
| R156P | <5 |
| R156V | 50 |
| R156T | 35 |
| R156S | 27 |
| R156A | 36 |
| R156D | 34 |
| R156K | 52 |
| R156N | 29 |
| R156I | 50 |
| T92I | 39 |
| R156Q | 34 |

TABLE 19

Sterile filtered enzyme samples stored for 16 hours at +44° C.

| Mutations | % Residual Activity |
|---|---|
| SEQ ID NO: 3 | 25 |
| R156Y | 70 |
| R156E | 66 |
| R156F | 65 |
| T92V | 43 |
| R156P | <5 |
| R156V | 53 |
| R156K | 38 |
| R156I | 31 |

TABLE 20

Sterile filtered enzyme samples stored for 16 hours at +44° C.

| Mutations | % Residual Activity |
|---|---|
| SEQ ID NO: 3 | 31 |
| R156Y | 65 |
| N415S | 34 |
| S443E | 33 |
| S443K | 32 |
| S443Q | 35 |
| K129T | 46 |
| K129A | 50 |
| G468Y | 32 |
| G237A | 34 |
| G237S | 34 |
| G237V | 25 |
| G468S | 32 |

TABLE 21

Sterile filtered enzyme samples stored for 16 hours at +44° C.

| Mutations | % Residual Activity |
|---|---|
| SEQ ID NO: 3 | 21 |
| R156Y | 45 |
| S332P | 41 |
| K129A + R156Y + K176S | 73 |
| K129A + R156Y + D303V | 77 |
| K129A + R156Y + D303S | 81 |
| R197L | 20 |
| R340N | 41 |
| R340T | 43 |
| H193S | 51 |
| H193D | 49 |
| H193T | 66 |
| L34F | 43 |
| Q137D | 24 |
| Q149E | 48 |
| T9D | 40 |
| A83E | 49 |
| S214E | 25 |
| K129A + R156Y | 98 |
| T92V | 49 |
| T92I | 36 |

TABLE 22

Sterile filtered enzyme samples stored for 16 hours at +47° C.

| Mutations | % Residual Activity |
|---|---|
| SEQ ID NO: 3 | <5 |
| R156Y | 29 |
| Q68H + R156V + G200P + N331F | 93 |
| Q68H + R156F + G200P + N331F | Approx. 100 |
| Q68H + G200P + N331F | Approx. 100 |
| Q68H + T92V + R156V + G200P + M310V | 86 |
| Q68H + T92V + R156Y + G200P + M310V | 86 |
| Q68H + T92V + R156F + G200P + M310V | 91 |
| Q68H + T92V + R156F + G200P + M310V + S484C | 82 |
| Q68H + T92V + G200P + M310V | 82 |
| Q68H + T92V + R156V + G200P + M310V + N331F | Approx. 100 |
| Q68H + T92V + R156Y + G200P + M310V + N331F | Approx. 100 |
| Q68H + T92V + R156F + G200P + M310V + N331F | 86 |
| Q68H + T92V + G200P + M310V + N331F | 80 |
| D366H | <5 |
| K118A + K129A + R156Y + G200P + N331F | 81 |
| Q68H + K118A + K129A + R156Y + G200P + N331F | 87 |
| Q68H + T92V + K118A + K129A + R156Y + G200P + N331F | 80 |
| M40L + A41T + Q67M + N72S + S76D + G78A + Q82K + Q137E + N153K + H164N + D249N + V272A + I337L + M356L + V397A + N415S + T421I + S424N + N441D + V450I + E489A + A490V + T517A + S522* | 41 |
| I10V + F17S + D33E + M40L + Q67M + N72S + S76D + G78A + Q82K + T92A + L102Q + Q137E + I222V + V228I + D249N + V272A + I337L + M356L + T374A + V397A + S416A + T421I + S424N + N441D + D444Y + V450I + A469E + K470T + I473G + T517A + S522P + P523V + V524E | 52 |
| Q32H + M40L + R49G + D65E + Q67M + N72S + S76D + G78A + Q82K + 92A + L102Q + T104A + Q137E + H164N + K202E + I222V + V228I + D249N + M356L + T374A | 41 |
| I10V + F17S + Y53H + Q67M + N72S + S76D + G78A + Q82K + T92A + L102Q + Q137E + T172V + A177T + I222V + V228I + D249N + S269N + I337L + M356LV397A + S416A + T421I + S424H + N441D + D444Y + A469E + K470T + I473G + T517A + S522* | 26 |

TABLE 23

Sterile filtered enzyme samples stored for 64 hours at +46° C.

| Mutations | % Residual Activity |
|---|---|
| SEQ ID NO: 3 | <5 |
| R156Y | <5 |
| Q68H + R156V + G200P + N331F | 80 |
| Q68H + R156F + G200P + N331F | 84 |
| Q68H + G200P + N331F | 63 |
| Q68H + T92V + R156V + G200P + M310V | 52 |
| Q68H + T92V + R156Y + G200P + M310V | 67 |
| Q68H + T92V + R156F + G200P + M310V | 63 |
| Q68H + T92V + R156F + G200P + M310V + S484C | 68 |
| Q68H + T92V + G200P + M310V | 48 |
| Q68H + T92V + R156V + G200P + M310V + N331F | 93 |
| Q68H + T92V + R156Y + G200P + M310V + N331F | 100 |
| Q68H + T92V + R156F + G200P + M310V + N331F | 91 |
| Q68H + T92V + G200P + M310V + N331F | 80 |
| K118A + K129A + R156Y + G200P + N331F | 56 |
| Q68H + K118A + K129A + R156Y + G200P + N331F | 86 |
| Q68H + T92V + K118A + K129A + R156Y + G200P + N331F | 88 |

TABLE 24

Sterile filtered enzyme samples stored for 16 hours at +44° C.

| Mutations | % Residual Activity |
|---|---|
| SEQ ID NO: 3 | 16 |
| R156Y | 52 |
| T374A | 27 |
| F146L + K322I | 24 |

TABLE 24-continued

Sterile filtered enzyme samples stored for 16 hours at +44° C.

| Mutations | % Residual Activity |
|---|---|
| K129A + Q137E + R156Y + G200P | 87 |
| Q68S | 14 |
| Q68T | <5 |
| K129A + R156Y | 71 |
| F146L | 26 |
| K129A + R156Y + G200P | 82 |
| Q68H | 77 |

TABLE 25

Sterile filtered enzyme samples stored for 16 hours at +44° C.

| Mutations | % Residual Activity |
|---|---|
| SEQ ID NO: 3 | 19 |
| R156Y | 53 |
| K101A + K129A | 47 |
| K129A + K470T | 46 |
| S332P | 29 |
| G413A | 30 |
| K118A + K129A + R156Y + A224P | 81 |
| K129A + K176P | 50 |
| K118A + K129A + R156Y + K169A + G200P + N331F | 89 |
| K118A + K129A + R156Y + G200P + M310V + N331F | 86 |
| K129A + R156Y + K454Q | 86 |
| K13A + K129A | 49 |
| G78A + T92V + K118A + K129A + R156Y + K169A | 93 |
| K129A + R156Y + K322I + K454Q | 76 |
| K129A | 47 |
| K129A + R156Y | 74 |
| K118A + K129A + R156Y | 77 |
| K118A + K129A + R156Y + G200P + N331F | Approx. 100 |
| G78A + T92V + K118A + K129A + R156Y | 93 |

TABLE 26

Sterile filtered enzyme samples stored for 6 days at +46° C.

| Mutations | % Residual Activity |
|---|---|
| SEQ ID NO: 3 | <5 |
| R156Y | <5 |
| Q68H + R156V + G200P + N331F | 50 |
| Q68H + R156Y + G200P + N331F | 60 |
| Q68H + R156F + G200P + N331F | 64 |
| Q68H + G200P + N331F | 40 |
| Q68H + T92V + R156V + G200P + M310V | 32 |
| Q68H + T92V + R156Y + G200P + M310V | 42 |
| Q68H + T92V + R156F + G200P + M310V | 43 |
| Q68H + T92V + R156F + G200P + M310V + S484C | 34 |
| Q68H + T92V + G200P + M310V | 27 |
| Q68H + T92V + R156F + G200P + M310V + N331F | 93 |
| Q68H + T92V + G200P + M310V + N331F | 58 |
| K118A + K129A + R156Y + G200P + N331F | 27 |
| Q68H + K118A + K129A + R156Y + G200P + N331F | 75 |
| Q68H + T92V + K118A + K129A + R156Y + G200P + N331F | 70 |

TABLE 27

Sterile filtered enzyme samples stored for 64 hours at +44° C.

| Mutations | % Residual Activity |
|---|---|
| SEQ ID NO: 3 | <5 |
| R156Y | 9 |
| K101A + K129A | 6 |
| K129A + K470T | 4 |
| S332P | <5 |
| G413A | <5 |
| K118A + K129A + R156Y + A224P | 51 |
| K129A + K176P | 6 |
| K118A + K129A + R156Y + K169A + G200P + N331F | 67 |
| K118A + K129A + R156Y + G200P + M310V + N331F | 63 |
| K129A + R156Y + K454Q | 52 |
| K13A + K129A | 5 |
| G78A + T92V + K118A + K129A + R156Y + K169A | 72 |
| K129A | 5 |
| K129A + R156Y | 32 |
| K118A + K129A + R156Y | 30 |
| K118A + K129A + R156Y + G200P + N331F | 63 |
| G78A + T92V + K118A + K129A + R156Y | 72 |

TABLE 28

Sterile filtered enzyme samples stored for 64 hours at +46° C.

| Mutations | % Residual Activity |
|---|---|
| SEQ ID NO: 3 | <5 |
| R156Y | 4 |
| G78A + T92V + K118A + K129A + R156Y + G200P + N331F | 71 |
| K118A + K129A + R156Y + G200P + N331F + N399I | 59 |
| K118A + K129A + F146L + R156Y + G200P + N331F | 62 |
| T92V + K118A + K129A + Q137E + R156Y + G200P + N331F | 74 |
| T92V + K118A + K129A + R156Y + H164N + G200P + N331F | 70 |
| Q68H + T92V + K118A + K129A + Q137E + R156Y + G200P + N331F | 87 |
| Q68H + T92V + K118A + S123T + K129A + Q137E + R156Y + G200P + N331F | 90 |
| T92V + K118A + K129A + R156Y + G200P + N331F | 66 |
| K118A + K129A + R156Y + G200P + N331F | 68 |
| Q68H T92V K118A K129A R156Y G200P N331F | 83 |

TABLE 29

Sterile filtered enzyme samples stored for 16 hours at +44° C.

| Mutations | % Residual Activity |
|---|---|
| SEQ ID NO: 3 | 19 |
| R156Y | 51 |
| S123P | 69 |
| V159M | 21 |
| V345I | 34 |
| G225S | 30 |
| V232A | <10 |

TABLE 30

Sterile filtered enzyme samples stored for 10 days at +46° C.

| Mutations | % Residual Activity |
|---|---|
| SEQ ID NO: 3 | <5 |
| R156Y | <5 |
| G78A + T92V + K118A + K129A + R156Y + G200P + N331F | 32 |
| K118A + K129A + R156Y + G200P + N331F + N399I | 16 |
| K118A + K129A + F146L + R156Y + G200P + N331F | 23 |
| T92V + K118A + K129A + Q137E + R156Y + G200P + N331F | 34 |
| T92V + K118A + K129A + R156Y + H164N + G200P + N331F | 31 |
| Q68H + T92V + K118A + K129A + Q137E + R156Y + G200P + N331F | 67 |
| Q68H + T92V + K118A + S123T + K129A + Q137E + R156Y + G200P + N331F | 81 |
| T92V + K118A + K129A + R156Y + G200P + N331F | 23 |
| K118A + K129A + R156Y + G200P + N331F | 25 |
| Q68H T92V K118A K129A R156Y G200P N331F | 61 |

TABLE 31

Sterile filtered enzyme samples stored for 16 hours at +44° C.

| Mutations | % Residual Activity |
|---|---|
| SEQ ID NO: 3 | 15 |
| R156Y | 51 |
| Q68F | <5 |
| Q68N | 69 |
| Q68Y | <5 |
| Q68D | <10 |
| Q68C | <10 |

TABLE 31-continued

Sterile filtered enzyme samples stored for 16 hours at +44° C.

| Mutations | % Residual Activity |
|---|---|
| Q68G | <10 |
| Q68S | <10 |
| Q68E | <5 |
| Q68A | <5 |
| Q68M | 27 |
| Q68W | <10 |
| Q68H | 82 |

TABLE 32

Sterile filtered enzyme samples stored for 7 days at +46° C.

| Mutations | % Residual Activity |
|---|---|
| SEQ ID NO: 3 | <5 |
| R156Y | <5 |
| Q68H + T92V + K118A + K129A + Q137E + R156Y + G200P + A224P + N331F | 81 |
| Q68H + T92V + K118A + Q137E + R156Y + G200P + N331F | 74 |
| Q68H + T92V + Q137E + R156Y + G200P + N331F | 80 |
| Q68H + T92V + K118A + Q137E + G200P + N331F | 65 |
| Q68H + T92V + K118A + Q137E + R156Y + N331F | 80 |
| Q68H + T92V + K118A + Q137E + R156Y + G200P | 67 |
| G78A + K118A + K129A + R156Y + K169A | 14 |
| Q68H + T92V + K118A + K129A + Q137E + R156Y + G200P + N331F | 73 |
| K129A + R156Y | <5 |
| G78A + K118A + K129A + R156Y | 7 |

TABLE 33

Sterile filtered enzyme samples stored for 48 hours at +46° C.

| Mutations | % Residual Activity |
|---|---|
| SEQ ID NO: 3 | <5 |
| R156Y | 9 |
| K118A + K129A + R156Y + G200P + N331F | 67 |
| Q68H + K118A + K129A + R156Y + G200P + N331F | 79 |
| Q68H + T92V + K118A + K129A + R156Y + G200P + N331F | 85 |
| Q68H + T92V + K118A + K129A + R156Y + H193T + D366H | 73 |
| Q68H + T92V + K118A + K129A + Q137E + R156Y + H193T + D366H | 72 |
| Q68H + T92V + R156Y + H193T + D366H | 78 |
| Q68H + T92V + R156F + H193T + D366H | 78 |
| Q68H + R156Y + H193T + D366H | 68 |
| Q68H + T92V + K118A + K129A + R156Y + H193T | 67 |
| Q68H + T92V + K118A + K129A + Q137E + R156Y + H193T | 80 |
| Q68H + T92V + R156Y + H193T | 84 |
| Q68H + T92V + R156F + H193T | 66 |
| Q68H + R156Y + H193T | 66 |
| Q68H + R156Y + H193T + G200P + M310V | 93 |
| Q68H + T92V + R156F + H193T + G200P + M310V | 82 |
| Q68H + T92V + K118A + K129A + Q137E + R156Y + H193T + G200P + M310V + E446K | 76 |
| Q68H + T92V + R156Y + H193T + G200P + M310V | 73 |
| Q68H + T92V + K118A + K129A + R156Y + H193T + G200P + M310V | 89 |
| Q68H + K129T + R156K + G200P + N331F | 95 |
| Q68H + K129A + R156K + G200P + N331F | 86 |
| Q68H + K118A + R156V + G200P + N331F | 81 |
| Q68H + K118S + R156F + G200P + G274D + N331F | 68 |

TABLE 34

Sterile filtered enzyme samples stored for 16 hours at +44° C.

| Mutations | % Residual Activity |
| --- | --- |
| SEQ ID NO: 3 | 22 |
| R156Y | 61 |
| S123T + K129A + R156Y | 83 |
| H193T | 44 |
| G78A + T92V + K118A + K129A + R156Y | 91 |
| S123T | 55 |
| S123P | 73 |
| V232A | <10 |
| K129A + R156Y | 64 |
| K118A + K129A + R156Y | 68 |

TABLE 35

Sterile filtered enzyme samples stored for 16 hours at +44° C.

| Mutations | % Residual Activity |
| --- | --- |
| SEQ ID NO: 3 | 17 |
| R156Y | 60 |
| N140F | 25 |
| H164A | 7 |
| H193A | 23 |
| R500T | 30 |
| R500A | 33 |
| R500V | 29 |
| H199A | <10 |
| H3A | 26 |
| H436A | 26 |
| H448A | <10 |
| H512A | 25 |
| H96A | 14 |
| H3A + H436A | 27 |

TABLE 36

Sterile filtered enzyme samples stored for 16 hours at +44° C.

| Mutations | % Residual Activity |
| --- | --- |
| SEQ ID NO: 3 | 27 |
| R156Y | 66 |
| N399I | 33 |
| L34F | 35 |
| Q149E | 35 |
| S332P | 36 |
| K129A | 50 |
| K21Q + K129A | 54 |
| K129A + K275Q | 56 |
| Q68F | 6 |
| T9D + L34F + A83E + Q149E + H193T + S332P + R340T | 53 |

TABLE 37

Sterile filtered enzyme samples stored for 12 days at +37° C.

| Mutations | % Residual Activity |
| --- | --- |
| SEQ ID NO: 3 | <5 |
| R156Y | 8 |
| K118A + K129A + R156Y + G200P + N331F | 52 |
| Q68H + K118A + K129A + R156Y + G200P + N331F | 47 |
| Q68H + T92V + K118A + K129A + R156Y + G200P + N331F | 67 |
| Q68H + R156Y + G200P + N331F | 47 |
| Q68H + R156F + G200P + N331F | 66 |

TABLE 37-continued

Sterile filtered enzyme samples stored for 12 days at +37° C.

| Mutations | % Residual Activity |
| --- | --- |
| Q68H + T92V + R156Y + G200P + M310V | 41 |
| Q68H + T92V + K118A + K129A + R156Y + H193T + D366H | 54 |
| Q68H + T92V + K118A + K129A + Q137E + R156Y + H193T + D366H | 44 |
| Q68H + T92V + R156Y + H193T + D366H | 44 |
| Q68H + T92V + R156F + H193T + D366H | 37 |
| Q68H + R156Y + H193T + D366H | 36 |
| Q68H + T92V + K118A + K129A + R156Y + H193T | 50 |
| Q68H + T92V + K118A + K129A + Q137E + R156Y + H193T | 56 |
| Q68H + T92V + R156Y + H193T | 37 |
| Q68H + T92V + R156F + H193T | 37 |
| Q68H + R156Y + H193T | 44 |
| Q68H + R156Y + H193T + G200P + M310V | 34 |
| Q68H + T92V + R156F + H193T + G200P + M310V | 28 |
| Q68H + T92V + K118A + K129A + Q137E + R156Y + H193T + G200P + M310V + E446K | 47 |
| Q68H + T92V + R156Y + H193T + G200P + M310V | 47 |
| Q68H + T92V + K118A + K129A + R156Y + H193T + G200P + M310V | 56 |

TABLE 38

Sterile filtered enzyme samples stored for 16 hours at +44° C.

| Mutations | % Residual Activity |
| --- | --- |
| SEQ ID NO: 3 | 19 |
| R156Y | 49 |
| G200S | 28 |
| G200D | 25 |
| G200Y | 12 |
| G200L | <5 |
| G200P | 37 |
| G200W | <5 |
| G200I | <5 |
| G200N | 9 |
| G200F | <5 |
| G200V | 9 |
| G200H | 12 |
| G200Q | 19 |
| G200C | 17 |
| G200A | 24 |
| G200M | 6 |
| G200K | 11 |
| G200E | 48 |
| G200R | <5 |
| G200T | 5 |

TABLE 39

Sterile filtered enzyme samples stored for 16 hours at +44° C.

| Mutations | % Residual Activity |
| --- | --- |
| SEQ ID NO: 3 | 13 |
| R156Y | 45 |
| K21Q + K129A | 34 |
| K129A + K275Q | 39 |
| T9D + L34F + A83E + Q149E + H193T + S332P + R340T | 43 |
| N399I | 24 |
| L34F | 22 |
| Q149E | 23 |
| S332P | 24 |
| K129A | 58 |
| G518D | 19 |

TABLE 39-continued

Sterile filtered enzyme samples stored for 16 hours at +44° C.

| Mutations | % Residual Activity |
|---|---|
| K118A + K129A | 73 |
| K118A | 48 |
| K129A + K169A | 40 |

TABLE 40

Purified enzyme samples stored for 5 days at +46° C.

| Mutations | % Residual Activity |
|---|---|
| SEQ ID NO: 3 | <5 |
| R156Y | <5 |
| Q68H + T92V + K118A + K129A + Q137E + R156Y + H193T + D366H | 73 |
| Q68H + R156Y + H193T | 63 |
| Q68H | 13 |
| Q68H + T92V + K118A + Q137E + R156Y + N331F | 70 |
| G78A + T92V + K118A + K129A + R156Y | 44 |
| K118A + K129A + R156Y + G200P + N331F | 46 |
| Q68H + T92V + K118A + K129A + R156Y + G200P + N331F | 83 |
| Q68H + K129T + R156K + G200P + N331F | 77 |
| Q68H + T92V + K118A + K129A + R156Y + H193T + D366H | 85 |

TABLE 41

Sterile filtered enzyme samples stored for 5 days at +46° C.

| Mutations | % Residual Activity |
|---|---|
| SEQ ID NO: 3 | <5 |
| R156Y | <5 |
| Q68H + T92V + K118A + K129A + Q137E + R156Y + H193T + N331K | 70 |
| Q68H + T92V + K118A + K129A + Q137E + R156Y + H193T + N331H | 42 |
| Q68H + T92V + K118A + K129A + Q137E + R156Y + H193T + N331Q | 24 |
| Q68H + T92V + K118A + K129A + Q137E + R156Y + H193T | 33 |
| Q68H + K118A + Q137E + R156Y + G200P + N331F | 74 |
| Q68H + S76W + T92V + K118A + Q137E + R156Y + G200P + N331F | 87 |
| K13A + Q68H + T92V + K118A + Q137E + R156Y + G200P | 54 |
| Q68H + T92V + K118A + Q137E + R156Y + G200P + D324N | 53 |
| Q68H + T92V + K118A + Q137E + R156Y + G200P + K470T | 69 |
| Q68H + T92V + K118A + Q137E + R156Y + G200P + N331F | 75 |
| Q68H + T92V + K118A + Q137E + R156Y + G200P | 52 |

TABLE 42

Sterile filtered enzyme samples stored for 16 hours at +44° C.

| Mutations | % Residual Activity |
|---|---|
| SEQ ID NO: 3 | 13 |
| R156Y | 43 |
| S76M | 21 |
| S76I | 36 |
| S76E | 19 |
| S76R | 26 |

TABLE 42-continued

Sterile filtered enzyme samples stored for 16 hours at +44° C.

| Mutations | % Residual Activity |
|---|---|
| S76K | 27 |
| S76V | 39 |
| S76R | 24 |

TABLE 43

Sterile filtered enzyme samples stored for 16 hours at +44° C.

| Mutations | % Residual Activity |
|---|---|
| SEQ ID NO: 3 | 20 |
| R156Y | 51 |
| K118A + R156Y | 62 |
| R197A | <5 |
| R20A | 26 |
| R267A | 26 |
| R295A | 23 |
| R314A | <10 |
| R340A | 23 |
| A221K | 25 |
| M290R | 23 |
| M373Q | 25 |
| V397S | 25 |
| T417K | 27 |
| N441G + A442E + S443D | 30 |
| S467R + G468S + A469T | 29 |
| I473T | 24 |
| A490R | 32 |
| T517A + G518D | 31 |
| V431E | 29 |
| S76W + G200P + A224P | 58 |
| S76W + G200P | 59 |
| G200P + A224P | 56 |
| S76T | 42 |
| M310V | 31 |
| G200P | 47 |
| G200E | 59 |
| M310V + N399I | <10 |
| Q68W | <5 |

TABLE 44

Sterile filtered enzyme samples stored for 16 hours at +46° C.

| Mutations | % Residual Activity |
|---|---|
| SEQ ID NO: 3 | 8 |
| R156Y | 40 |
| Q68H + T92V + K118A + Q137E + N140F + R156Y + G200P + K470T | 89 |
| Q68H + T92V + K118A + S123P + K129A + Q137E + R156Y + G200P + N331F | 88 |
| T92V + K118A + Q137E + R156Y + G200P + N331F | 88 |
| S76W + G200P + A224P | 44 |
| S76W + G200P | 45 |
| G200P + A224P | 48 |
| S76T | 26 |
| Q68H + T92V + K118A + Q137E + R156Y + G200P + M310L | 91 |
| Q68H + T92V + K118A + K129A + Q137E + R156Y + G200P + N331F | 95 |
| G200P | 39 |

TABLE 45

Sterile filtered enzyme samples stored for 9 days at +46° C.

| Mutations | % Residual Activity |
|---|---|
| SEQ ID NO: 3 | <5 |
| R156Y | <5 |
| Q68H + T92V + K118A + K129A + Q137E + R156Y + H193T + N331K | 46 |
| Q68H + T92V + K118A + K129A + Q137E + R156Y + H193T + N331H | 19 |
| Q68H + T92V + K118A + K129A + Q137E + R156Y + H193T + N331Q | 9 |
| Q68H + T92V + K118A + K129A + Q137E + R156Y + H193T | 17 |
| Q68H + K118A + Q137E + R156Y + G200P + N331F | 48 |
| Q68H + S76W + T92V + K118A + Q137E + R156Y + G200P + N331F | 65 |
| K13A + Q68H + T92V + K118A + Q137E + R156Y + G200P | 31 |
| Q68H + T92V + K118A + Q137E + R156Y + G200P + D324N | 30 |
| Q68H + T92V + K118A + Q137E + R156Y + G200P + K470T | 41 |
| Q68H + T92V + K118A + Q137E + R156Y + G200P + N331F | 50 |
| Q68H + T92V + K118A + Q137E + R156Y + G200P | 30 |

TABLE 46

Purified enzyme samples stored for 9 days at +46° C.

| Mutations | % Residual Activity |
|---|---|
| SEQ ID NO: 3 | <5 |
| R156Y | <5 |
| Q68H + T92V + K118A + K129A + Q137E + R156Y + H193T + D366H | 52 |
| Q68H + R156Y + H193T | 34 |
| Q68H + T92V + K118A + Q137E + R156Y + N331F | 45 |
| G78A + T92V + K118A + K129A + R156Y | 14 |
| K118A + K129A + R156Y + G200P + N331F | 18 |
| Q68H + T92V + K118A + K129A + R156Y + G200P + N331F | 56 |
| Q68H + K129T + R156K + G200P + N331F | 47 |
| Q68H + T92V + K118A + K129A + R156Y + H193T + D366H | 52 |
| Q68H + R156Y + H193T | 31 |

TABLE 47

Sterile filtered enzyme samples stored for 30 days at +37° C.

| Mutations | % Residual Activity |
|---|---|
| SEQ ID NO: 3 | <5 |
| R156Y | <5 |
| K118A + K129A + R156Y + G200P + N331F | 33 |
| Q68H + K118A + K129A + R156Y + G200P + N331F | 42 |
| Q68H + T92V + K118A + K129A + R156Y + G200P + N331W | 52 |
| Q68H + R156Y + G200P + N331F | 41 |
| Q68H + R156F + G200P + N331F | 58 |
| Q68H + T92V + R156Y + G200P + M310V | 41 |
| Q68H + T92V + R156F + G200P + M310V | 42 |
| Q68H + T92V + K118A + K129A + R156Y + H193T + D366H | 50 |
| Q68H + T92V + K118A + K129A + Q137E + R156Y + H193T + D366H | 32 |
| Q68H + T92V + R156Y + H193T + D366H | 33 |
| Q68H + T92V + R156F + H193T + D366H | 28 |
| Q68H + R156Y + H193T + D366H | 25 |
| Q68H + T92V + K118A + K129A + R156Y + H193T | 41 |
| Q68H + T92V + K118A + K129A + Q137E + R156Y + H193T | 43 |
| Q68H + T92V + R156Y + H193T | 27 |
| Q68H + T92V + R156F + H193T | 23 |
| Q68H + R156Y + H193T | 33 |
| Q68H + R156Y + H193T + G200P + M310V | 28 |
| Q68H + T92V + R156F + H193T + G200P + M310V | 21 |
| Q68H + T92V + K118A + K129A + Q137E + R156Y + H193T + G200P + M310V + E446K | 35 |
| Q68H + T92V + R156Y + H193T + G200P + M310V | 35 |
| Q68H + T92V + K118A + K129A + R156Y + H193T + G200P + M310V | 46 |

TABLE 48

Sterile filtered enzyme samples stored for 16 hours at +44° C.

| Mutations | % Residual Activity |
|---|---|
| SEQ ID NO: 3 | 15 |
| R156Y | 49 |
| A83S | 15 |
| A83N | 9 |
| A83Y | 10 |
| A83H | 14 |
| A83I | 8 |
| A83L | 10 |
| A83R | 16 |
| A83D | 17 |
| A83T | 12 |
| A83E | 31 |
| L34V | 22 |
| L34M | 19 |
| L34I | 24 |
| M310I | 21 |
| M310V | 20 |
| M310L | 18 |

TABLE 49

Sterile filtered enzyme samples stored for 3 days at +35° C.

| Mutations | % Residual Activity |
|---|---|
| SEQ ID NO: 3 | 61 |
| R156Y | 89 |
| N331K | 57 |
| N331R | 54 |
| N331L | 39 |
| N331H | 62 |
| N331G | 59 |
| N331M | 70 |
| N331W | 55 |
| N331S | 58 |
| N331V | 57 |
| N331T | 46 |
| N331Y | 55 |
| N331I | 47 |
| N331A | 87 |
| N331Q | 82 |
| N331C | 70 |
| N331E | 58 |
| N331D | 63 |
| N331P | 26 |
| N331F | 51 |

TABLE 50

Sterile filtered enzyme samples stored for 16 hours at +44° C.

| Mutations | % Residual Activity |
|---|---|
| SEQ ID NO: 3 | 20 |
| R156Y | 58 |
| I10V + F17S + Q67M + N72S + S76D + G78A + Q82K + T104A + Q137E + N153K + R156Q + V219A + I222V + V228I + D249N + S269N + V272A + E333A + I337L + M356L + V397A + N415S + D420G + T421I + S424H + N441D + D444Y + V450I + A469E + K470T + I473G + T517A + S522* | 72 |
| I10V + D33E + M40L + A41T + Q67M + Y73F + S76D + G78A + Q82K + T92A + L102Q + Q137E + I222V + V228I + D249N + S269N + V272A + E333A + I337L + M356L + T374A + S416A + D444Y + A469E + K470T + I473G + T517A + S522* | 71 |
| I10V + F17S + D33E + M40L + Q67M + N72S + S76D + G78A + Q82K + T92A + L102Q + Q137E + H164N + N168K + T172A + V219A + I222V + V228I + D249N + S269N + V272A + E333A + I337L + M356L + N415S + T421I + S424H + N441D + D444Y + S522P + P523V + V524E | 78 |
| I10V + F17S + D33E + Q67M + N72S + S76D + G78A + Q82K + T92A + L102Q + Q137E + N168K + T172A + I222V + V228I + D249N + V272A + E333A + I337L + M356L + V397A + S416A + T421I + S424H + N441D + D444Y + A469E + K470T + I473S + V477I + E489A + A490V + T517A + S522* | 74 |
| I10V + F17S + M40L + Q67M + N72S + S76D + G78A + Q82K + T92A + L102Q + Q137E + I222V + V228I + D249N + S269N + V272A + T320A + I337L + M356L + T374A + V397A + N415S + T421I + S424H + N441D + D444Y + A469E + K470T + I473S + V477I + T517A + S522P + P523V + V524E | 73 |
| I10V + F17S + D33E + M40L + A41T + Q67M + N72S + S76D + G78A + Q82K + Q137E + V219A + D249N + V272A + I337L + M356L + V397A + S416A + T421I + S424N + N441D + D444Y + V450I + K470T + I473S + V477I | 64 |
| I10V + F17S + Q67M + N72S + S76D + G78A + Q82K + T92A + T104A + Q137E + R156Q + V159A + H164N + N168K + T172A + I222V + V228I + D249N + V272A | 66 |
| K118A + K129A + R156Y + G200P + N331F | 98 |
| Q68H + T92V + K118A + K129A + R156Y + G200P + N331F | Approx 100 |

TABLE 51

Sterile filtered enzyme samples stored for 2 days at +44° C.

| Mutations | % Residual Activity |
|---|---|
| SEQ ID NO: 3 | <5 |
| R156Y | 20 |
| Q68H + R156Y | 61 |
| Q68H + T92V + K118A + R156Y | 66 |
| Q68H + T92V + R156Y | 68 |
| Q68H + K118A + R156Y + H193T + D366H | 74 |
| Q68H + T92V + K118R + R156Y + H193T + D366H | 65 |
| Q68H + T92V + K118R + R156F | 63 |
| Q68H + K118R + R156Y | 68 |
| Q68H + T92V + R156Y + H193T + D366H | 69 |
| Q68H + K118R + R156Y + G200P | 74 |
| Q68H + K118R + R156F | 66 |
| K118A + K129A + R156Y + G200P + N331F | 79 |
| Q68H + T92V + K118A + K129A + R156Y + G200P + N331F | 91 |
| Q68H | 55 |
| D33V + Q68H + N168H + V450I | 70 |
| S123T | 10 |
| K129A | 10 |

The invention claimed is:

1. A non-naturally occurring variant of a parent xyloglucanase, which comprises a substitution at a position corresponding to position 68 of SEQ ID NO: 3 with H, L, M, or N, wherein
(a) the variant has at least 95% identity to the amino acid sequence of SEQ ID NO: 3;
(b) the parent xyloglucanase is a family 44 xyloglucanase; and
(c) the variant has xyloglucanase activity.

2. The variant of claim 1, wherein the variant has two alterations.

3. The variant of claim 1, which comprises one or more of the following combinations of alterations:
K13A+Q68H+T92V+K118A+Q137E+R156Y+G200P;
D33V+Q68H+N168H+V450I;
Q68H+S76W+T92V+K118A+Q137E+R156Y+G200P+ N331F;
Q68H+T92A,D,I,S,V,Y+K118A+K129A+R156Y+ G200P+N331F;
Q68H+T92N+D97N+K118A+K129A+R156Y+G200P+ N331F;
Q68H+T92S+K118A+K129A+R156Y+G200P+G274D+ N331F;
Q68H+T92V+K118A+S123P,T+K129A+Q137E+ R156Y+G200P+N331F;
Q68H+T92V+K118A+K129A+Q137E+R156Y+H193T;
Q68H+T92V+K118A+K129A+Q137E+R156Y+ H193T+G200P+M310V+E446K;
Q68H+T92V+K118A+K129A+Q137E+R156Y+ H193T+N331H, K, Q;
Q68H+T92V+K118A+K129A+Q137E+R156Y+ H193T+D366H;
Q68H+T92V+K118A+K129A+Q137E+R156Y+ G200P+A224P+N331F;
Q68H+T92V+K118A+K129A+Q137E+R156Y+ G200P+N331F;
Q68H+T92V+K118A+K129A+R156Y+H193T;
Q68H+T92V+K118A+K129A+R156Y+H193T+ G200P+M310V;
Q68H+T92V+K118A+K129A+R156Y+H193T+D366H;
Q68H+T92V+K118A+K129A+R156Y+G200P+N331F;
Q68H+T92V+K118A+Q137E+N140F+R156Y+G200P+ K470T;
Q68H+T92V+K118A+Q137E+R156Y+G200P+M311F;
Q68H+T92V+K118A+Q137E+R156Y+G200P+D324N;
Q68H+T92V+K118A+Q137E+R156Y+G200P+N331F;
Q68H+T92V+K118A+Q137E+R156Y+G200P+K470T;
Q68H+T92V+K118A,R+R156Y,F;
Q68H+T92V+K118R+R156Y+H193T+D366H;
Q68H+T92V+Q137E+R156Y+G200P+N331F;
Q68H+T92V+R156F+G200P+M310V+S484C;
Q68H+T92V+R156F,V,Y+G200P+M311F;
Q68H+T92V+R156F,V,Y+G200P+M310V+N331F;
Q68H+T92V+R156F,Y+H193T;
Q68H+T92V+R156F,Y+H193T+G200P+M310V;
Q68H+T92V+R156F,Y+H193T+D366H;
Q68H+T92V+R156Y;
Q68H+T92V+G200P+M310V;
Q68H+T92V+G200P+M310V+N331F;
Q68H+K118A+K129A+R156Y+G200P+N331F;
Q68H+K118A+R156V+G200P+N331F;
Q68H+K118A+R156Y+H193T+D366H;
Q68H+K118R+R156F,Y;
Q68H+K118R+R156Y+G200P;
Q68H+K118S+R156F+G200P+G274D+N331F;
Q68H+K129A,T+R156K+G200P+N331F;
Q68H+R156F,V,Y+G200P+N331F;
Q68H+R156Y;
Q68H+R156Y+H193T;
Q68H+R156Y+H193T+G200P+M310V;
Q68H+R156Y+H193T+D366H; or
Q68H+G200P+N331F.

4. The variant of claim 1, which further comprises one or more substitutions at one or more additional positions selected from the group consisting of 123, 156, 118, 200, 129, 137, 193, 92, 83, 149, 34, 340, 332, 9, 76, 331, 310, 324, 498, 395 and 366.

5. The variant of claim 4, wherein the variant comprises one or more substitutions selected from the group consisting of: S123P,T; R156Y,F,V,I,K,W,L,M; K118A,R; G200P,E,S, D; K129T,A,S; Q137E; H193T,S,D; T92V,I,A,S; A83E; Q149E; L34F,I,V; R340T,N; S332P; T9D; S76W,V,I,K,R,T; N331F,C; M310I,V,L; D324N; G498A,D; D395G and D366H.

6. The variant of claim 5, wherein the variant comprises one or more substitutions selected from the group consisting of: S123P; R156Y,F; K118A; G200P,E; K129T,A; Q137E; H193T; T92V and N331F.

7. The variant of claim 1, wherein the variant has improved chemical stability compared to the parent xyloglucanase.

8. The variant of claim 7, wherein the improved chemical stability results in improved detergent stability.

9. A formulation comprising the variant of claim 1.

10. The formulation of claim 9, wherein the formulation is a liquid formulation.

* * * * *

UNITED STATES PATENT AND TRADEMARK OFFICE
CERTIFICATE OF CORRECTION

PATENT NO. : 8,709,777 B2  
APPLICATION NO. : 12/995706  
DATED : April 29, 2014  
INVENTOR(S) : Werner Besenmatter et al.

Page 1 of 1

It is certified that error appears in the above-identified patent and that said Letters Patent is hereby corrected as shown below:

In the Claims

In Claim 3, line 33 at column 113, line 62, delete "M311F" and insert --M310L--.

In Claim 3, line 41 at column 114, line 21, delete "M311F" and insert --M310V--.

Signed and Sealed this  
Ninth Day of September, 2014

Michelle K. Lee  
*Deputy Director of the United States Patent and Trademark Office*